(12) United States Patent
Kleefeld et al.

(10) Patent No.: US 9,593,140 B2
(45) Date of Patent: Mar. 14, 2017

(54) ANTIBACTERIAL TYLOSIN DERIVATIVES AND METHODS FOR THEIR PREPARATION

(71) Applicants: Bayer Intellectual Property GmbH, Monheim (DE); The Kitasako Institute, Tokyo (JP)

(72) Inventors: Gerd Kleefeld, Neuss (DE); Robrecht Froyman, Monheim (DE); Julia Charlotte Dörner, Meerbusch (DE); Carolin Ludwig, Meerbusch (DE); Omura Satoshi, Tokyo (JP); Sunazuka Toshiaki, Chiba (JP); Hirose Tomoyasu, Kanagawa (JP); Sugawara Akihiro, Tokyo (JP); Shiomi Kazuro, Tokyo (JP)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/360,713

(22) PCT Filed: Nov. 21, 2012

(86) PCT No.: PCT/EP2012/073277
§ 371 (c)(1),
(2) Date: May 27, 2014

(87) PCT Pub. No.: WO2013/076169
PCT Pub. Date: May 30, 2013

(65) Prior Publication Data
US 2014/0349954 A1    Nov. 27, 2014

(30) Foreign Application Priority Data
Nov. 25, 2011    (EP) ..................................... 11190748

(51) Int. Cl.
*C07H 17/08* (2006.01)
*C07H 1/00* (2006.01)

(52) U.S. Cl.
CPC .............. *C07H 17/08* (2013.01); *C07H 1/00* (2013.01)

(58) Field of Classification Search
CPC .................................. C07H 17/08; C07H 1/00
See application file for complete search history.

(56) References Cited

U.S. PATENT DOCUMENTS

| 5,545,624 A | 8/1996 | Hecker et al. |
| 2006/0014707 A1 | 1/2006 | Fu et al. |

FOREIGN PATENT DOCUMENTS

| EP | 0 201 166 | 11/1986 |
| EP | 0 240 264 A2 | 3/1987 |
| EP | 0 606 747 A1 | 7/1994 |
| EP | 2 019 112 A1 | 1/2009 |
| EP | 2 124 216 A2 | 11/2009 |
| WO | 96/09312 A1 | 3/1996 |
| WO | 03/039558 A1 | 5/2003 |
| WO | 03/043642 A1 | 5/2003 |
| WO | 03/089446 A2 | 10/2003 |
| WO | 03/089447 A1 | 10/2003 |
| WO | 2005/085266 A2 | 9/2005 |
| WO | 2005/118610 A2 | 12/2005 |
| WO | WO 2005/118610 A2 * | 12/2005 |
| WO | 2007/025089 A2 | 3/2007 |
| WO | 2007/071370 A1 | 6/2007 |
| WO | 2008/012343 | 1/2008 |
| WO | 2009/064953 A1 | 5/2009 |

OTHER PUBLICATIONS

Tornoe et al., "Peptidotriazoles on Solid Phase: [1,2,3]-Triazoles by Regiospecific Copper(I)-Catalyzed 1,3-Dipolar Dycloadditions of Terminal Alkynes to Azides," Journal of Organic Chemistry, 2002, 67(9):3057-3064.
Valette et al., "Decomposition Pathways and in Vitro HIV Inhibitory Effects of IsoddA Pronucleotides: Toward a Rational Approach for Intracellular Delivery of Nucleoside 5'-Monophosphates," Journal of Medicinal Chemistry,1996, 39(10):1981-1990.
Wada et al., "Studies on Selectin Blockers. 2. Novel Selectin Blocker as Potential Therapeutics for Inflammatory Disorders," Journal of Medicinal Chemistry, 1996, 39(10):2055-2059.
Wang et al., "Antitumor Agents. 166. Synthesis and Biological Evaluation of 5,6,7,8-Substituted-2-phenylthiochromen-4-ones," Journal of Medicinal Chemistry,1996, 39(10):1975-1980.
Wang et al., "Discovery of Novel, Non-Peptide HIV-1 Protease Inhibitors by Pharmacophore Searching," Journal of Medicinal Chemistry, 1996, 39(10):2047-2054.

(Continued)

*Primary Examiner* — Layla Berry
(74) *Attorney, Agent, or Firm* — McBee Moore Woodward & Vanik IP, LLC

(57) ABSTRACT

The present invention relates to new macrolide derivatives, in particular new tylosin derivatives of the formula (I); a pharmaceutical or veterinary composition comprising the derivatives; a method for preparation thereof; a method for treating and/or preventing bacterial infections in an animal, wherein the method comprises administering the derivatives or the composition; and a use of the derivatives for the manufacture of medicaments for treating and/or preventing bacterial infections in an animal.

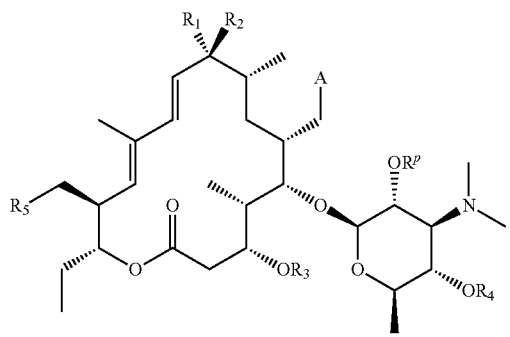

14 Claims, No Drawings

(56) References Cited

OTHER PUBLICATIONS

Woodward, R. B., Struktur and Biogenese der Makrolide Eine neue Klasse von Naturstoffen, Angewandte Chemie International Edition, 1957, 69(112):50-58.
Yamada et al., "(Aminoalkyl)indole Isothiocyanates as Potential Electrophilic Affinity Ligands for the Brain Cannabinoid Receptor," Journal of Medicinal Chemistry, 1996, 39(10):1967-1974.
Giencke et al., "Total Synthesis of the Azoxy Antibiotic Jietacin A," Liebigs Annalen der Chemie Journal, 1989, 671-676.
Burg et al., "Avermectins, New Family of Potent Anthelmintic Agents: Producing Organism and Fermentation," Antimicrobial Agents and Chemotherapy, Mar. 1979, 15(3):361-367.
Imamura et al., Structures of Jietacines: Unique α,β-Unsaturated Azoxy Antibiotics, The Journal of Antibiotics, Jan. 1989, 142(1):156-158.
Nam et al., "Synthesis and Anti-Tumor Activity of Novel Combretastatins: Combretocyclopentenones and Related Analogues," Bioorganic & Medicinal Chemistry Letters, 2002, 12:1955-1958.
Thakkalapally et al., "Synthesis, structural studies and desilylation reactions of some N-2-(trimethylsilyl)ethyl-Nnitrosocarbamates," Tetrahedron, 2005, 61:4939-4948.
Ahammed et al., "Hydrogenation of Azides over Copper Nanoparticle Surface Using Ammonium Formate in Water," the Journal of Organic Chemistry, 2011, 76:7235-7239.
Andreadou et al., "Synthesis of Novel Se-Substituted Selenocysteine Derivatives as Potential Kidney Selective Prodrugs of Biologically Active Selenol Compounds: Evaluation of Kinetics of â-Elimination Reactions in Rat Renal Cytosol;" Journal of Medicinal Chemistry, 1996, 39(10)2040-2046.
Bertha et al., "Probes for Narcotic Receptor-Mediated Phenomena. 21. Novel Derivatives of 3-(1,2,3,4,5,11-Hexahydro-3-methyl-2,6-methano-6H-azocino[4,5-b]indo1-6-yl)-phenols with Improved δ Opioid Receptor Selectivity," Journal of Medicinal Chemistry, 1996, 39(10):2081-2086.
Boyfield et al., "Design and Synthesis of 2-Naphthoate Esters as Selective Dopamine D4 Antagonists," Journal of Medicinal Chemistry, 1996, 39(10):1946-4948.
Brockmann et al., Naturwissenschaften, 1950, 138-139.
Chan et al., Polytriazoles as Copper(I)-Stabilizing Ligands in Catalysis, Organic Letters, 2004, 6(17):2853-2855.
Chen et al., "Aminodiol HIV Protease Inhibitors. Synthesis and Structure-Activity Relationships of P1/P1' Compounds: Correlation between Lipophilicity and Cytotoxicity," Journal of Medicinal Chemistry, 1996, 39 :10):1991-2007.
National Agricultural Statistics Service (NASS), US Department of Agriculture (USDA), "Cattle Death Loss," May 5, 2006, 1-15.
Coutts et al., "Structure-Activity Relationships of Boronic Acid Inhibitors of Dipeptidyl Peptidase IV. 1. Variation of the P2 Position of Xaa-boroPro Dipeptides," Journal of Medicinal Chemistry, 1996, 39(10):2087-2094.
Debono et al., "Synthesis and Antimicrobial Evaluation of 20-Deoxo-20-(3,5-Dimethylpiperidin-1-YL)Desmycocin (Tilmicosin, EL-870) and Related Cyclic Amino Derivatives," The Journal of Antibiotics, Aug. 1989, 62(8)1253-1267.
Ducruix et al., "Crystal and Molecular Structure of Diacetyl-3,6-bicyclo-leuconolide A3," Journal of the Chemical Society, Chemical Communications, 1997, 947-948.
Fleisher et al., "Improved oral drug delivery: solubility limitations overcome by the use of prodrugs," Advanced Drug Delivery Reviews, 1996, 19:115-130.
Galli et al., "Identification of a sirtuin 3 inhibitor that displays selectivity over sirtuin 1 and 2," European Journal of Viedicinal Chemistry, 2012, 55:58-66.
Gao et al., "Screening Derivatized Peptide Libraries for Tight Binding Inhibitors to Carbonic Anhydrase II by Electrospray Ionization-Mass Spectrometry," Journal of Medicinal Chemistry, 1996, 39:1949-1955.

Greenwald et al., "Drug Delivery Systems. 2. Camptothecin 20-O-Poly(ethylene glycol) Ester Transport Forms," Journal of Medicinal Chemistry, 1996, 39(10):1938-1940.
Gruet et al., "Bovine mastitis and intramammary drug delivery: review and perspectives," Advanced Drug Delivery Reviews, 2001, 50:245-259.
Guichard et al., "Partially Modified Retro-Inverso Pseudopeptides as Non-natural Ligands for the Human Class I Histocompatibility Molecule HLA-A2," Journal of Medicinal Chemistry, 2996, 39:2030-2039.
Hansen et al., "The Structures of Four Macrolide Antibiotics Bound to the Large Ribosomal Subunit," Molecular Cell, Jul. 2002, 10:117-128.
Harper et al., "Pasteurella multocida pathogenesis:125 years after Pasteur," FEMS Microbiology Letters, 2006, 265:1-10.
Hirose et al., "Rapid 'Sar' Via Click Chemistry: An Alkyne-Bearing Spiramycin Is Fused With Diverse Azides to Yield New Triazole-Antibacterial Candidates," Heterocycles, 2006, 69:55-61.
Huisgen, R., et al., "Kinetics and reaction mechanisms: selected examples from the experience of forty years," 1989, Pure & Applied Chemistry 61(4):613-628.
Kirst et al., "Synthesis and Evaluation of Tylosin-Related Macrolides Modified at the Aldehyde Function: A New Series of Orally Effective Antibiotics," Journal of Medicinal Chemistry, 1988, 31(8):1631-1641.
Kirst et al., "Synthesis, Antimicrobial Evaluation and Structure-Activity Relationships within 23-Modified Derivatives of 5-0-Mycaminosyltylonolide" The Journal of Antibiotics, Jun. 1987, 40(6)-823-842.
Kolb et al. "Click Chemistry: Diverse Chemical Function from a Few Good Reactions," Angewandte Chemie International Edition, 2001, 40:2004-2021.
Kulagowski et al, "3[[4-(4-Chlorophenyl)piperazin-1-yl]-methy]-1H-pyrrolo[2,3-b]pyridine: An Antagonist with High Affinity and Selectivity for the Human Dopamine D4 Receptor," Journal of Medicinal Chemistry, 1996, 39:1941-1942.
Lehr et al., "Inhibitors of Human Immunodeficiency Virus Type 1 Protease Containing 2-Aminobenzyl-Substituted 4-Amino-3-hydroxy-5-phenylpentanoic Acid: Synthesis, Activity, and Oral Bioavailability," Journal of Medicinal Chemistry, 1996, 39:2060-2067.
Lima-Neto et al., "Synthesis of 1,2,3-Triazole Derivatives and in Vitro Antifungal Evaluation on Candida Strains," Molecules, 2012, 17:5882-5892.
Lombardi et al., "Rational Design of True Hirudin Mimetics: Synthesis and Characterization of Multisite-Directed a-Thrombin Inhibitors1," Journal of Medicinal Chemistry, 1996, 39(10):2008-2017.
Ma et al., "Novel Erythromycin Derivatives with Aryl Groups Tethered to the C-6 Position Are Potent Protein Synthesis Inhibitors and Active against Multidrug-Resistant Respiratory Pathogens," Journal of Medicinal Chemistry, 2001, 44 (24):4137-4156.
Mamidyala et al., "Probing the reactivity of o-phthalaldehydic acid/methyl ester: synthesis of N-isoindolinones and 3-arylaminophthalides," Chemical Communications—Royal Society of Chemistry, 2013, 49:8407-8409.
Marshall et al., "Proposed MIC Quality Control Guidelines for National Committee for Clinical Laboratory Standards Susceptibility Tests Using Seven Veterinary Antimicrobial Agents: Ceftiofur, Enrofloxacin, Florfenicol, Penicillin G-Novobiocin, Pirlimycin, Premafloxacin, and Spectinomycin," Journal of Clinical Microbiology, Aug. 1996, 34 (8):2027-2029.
McCARTHY et al., "11-Ketotigogenin Cellobioside (Pamaqueside): A Potent Cholesterol Absorption Inhibitor in the Hamster1," Journal of Medicinal Chemistry, 1996, 39(10):1935-1937.
McGuire et al., "Tylosin, a New Antibiotic: I. Microbiological Studies," Journal M. Antibiot. Chemotherapy, 1961, 11:320-327.
Mereu et al., "Design, synthesis and in vivo activity of 9-(S)-dihydroerythromycin derivatives as potent anti-inflammatory agents," Bioorganic & Medicinal Chemistry Letters, 2006, 16:5801-5804.

(56) References Cited

OTHER PUBLICATIONS

Mi et al., "Advances in triazole antimicrobial agents," Chinese Journal of Antibiotics, 2007, 32(10):587-592.

Morin et al., "The Structure of Tylosin 1, 2," Tetrahedron Letters, 1970, 54:4737-4740.

Omura et al., "Carbon-13 Nuclear Magnetic Resonance Spectral Analysis of 16-Membered Macrolide Antibiotics1," Journal of the American Chemical Society, Jul. 9, 1975, 97(14):4001-4009.

Omura, S., "Microbial metabolites: 45 years of wandering, wondering and discovering," Tetrahedron, 2011, 67:6420-6459.

Pinnert-Sindico et al., "A New Antibiotic-Spiramycin," Antibiotics Annual, 1955, 2:1954-1955.

Pokhodylo et al., "Methyl 3-Cyclopropyl-3-oxopropanoat 2010, in the Synthesis of Heterocycles Having a Cyclopropyl Substituent," Russian Journal of Organic Chemistry, 2010, 46(6):894-897.

Rault et al, "Novel Selective and Partial Agonists of 5-HT3 Receptors. Part 1. Synthesis and Biological Evaluation of Piperazinopyrrolothienopyrazines," Journal of Medicinal Chemistry, 1996, 39(10):2068-2080.

Rostovtsev et al., "A Stepwise Huisgen Cycloaddition Process: Copper(I)-Catalyzed Regioselective Ligation of Azides and Terminal Alkynes," Angewandte Chemie International Edition, 2002, 41(14):2596-2599.

Rowley et al., "5-(4-Chlorophenyl)-4-methyl-3-(1-(2-phenylethyl)piperidin-4-yl)isoxazole: A Potent, Selective Antagonist at Human Cloned Dopamine D4 Receptors," Journal of Medicinal Chemistry, 1996, 39(10):1943-1945.

Sashida et al., "Studies on Diazepines. XXIX.1) Syntheses of 3H- and 5H-1,4-Benzodiazepines from 3-Azidoquinolines," Chemical and Pharmaceutical Bulletin, 1987, 35(10):4110-4116.

Schultz et al., "Asymmetric Syntheses, Opioid Receptor Affinities, and Antinociceptive Effects of 8-Amino-5,9-methanobenzocyclooctenes, a New Class of Structural Analogues of the Morphine Alkaloids," Journal of Medicinal Chemistry, 1996, 39(10):1956-1966.

Shen et al., "Oxidation Chemistry of (-)-Norepinephrine in the Presence of L-Cysteine," Journal of Medicinal Chemistry, 1996, 39(10):2018-2029.

Shpigel et al., "Anti-inflammatory ketoprofen in the treatment of field cases of bovine mastitis," Research in Veterinary Science, 1994, 56:62-68.

Smith, R. A., "Impact of Disease on Feedlot Performance: A Review1," Journal of Animal Science, 1998, 76:272-274.

Sugawara et al., "Design and synthesis via click chemistry of 8,9-anhydroerythromycin a 6,9-hemiketal analogues with anti-MRSA and -VRE activity," Bioorganic & Medicinal Chemistry Letters, 2007, 17:6340-6344.

Thurieau et al., "Design and Synthesis of New Linear and Cyclic Bradykinin Antagonists1," Journal of Medicinal Chemistry, 1996, 39(10):2095-2101.

Brouillette E. et al., Veterinary Microbiology 101 (2004) pp. 253-262.

Fu, H. et al., Bioorganic & Medicinal Chemistry Letters 16(5) (2006) pp. 1259-1266.

* cited by examiner

ANTIBACTERIAL TYLOSIN DERIVATIVES AND METHODS FOR THEIR PREPARATION

BACKGROUND OF THE INVENTION

The present invention relates to new macrolide derivatives, in particular new tylosin derivatives; a pharmaceutical or veterinary composition comprising any of the derivatives; a method for preparation thereof; a method for treating and/or preventing bacterial infections in an animal, wherein the method comprises administering any of the derivatives or the composition; and a use of the derivatives for the manufacture of medicaments for treating and/or preventing bacterial infections in an animal.

Macrolides in generally have a chemical structure of 12-, 14- or 16-membered macrocyclic group (aglycone) substituted with 1 to 3 substituents such as neutral sugars, deoxy sugars or amino sugars. Macrolides have a wide spectrum of antibacterial activities against for example *Pneumococcus* spp, *Streptococcus* spp, *Hemophilus influenzae*, *Staphylococcus aureus*, *Actinobacillus* spp, *Pasteurella* spp and atypical pathogen such as *Mycoplasma, Legionella* or *Chlamydia* that is resistant to other drugs. Consequently, macrolides have been used for the treatment of among others a variety of respiratory tract infections. A variety of macrolides have been discovered or synthesized until now, typically including tylosin represented by the following formula:

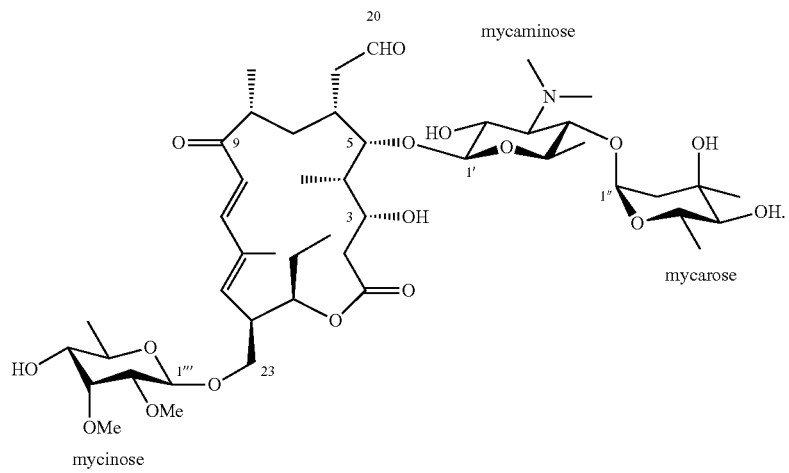

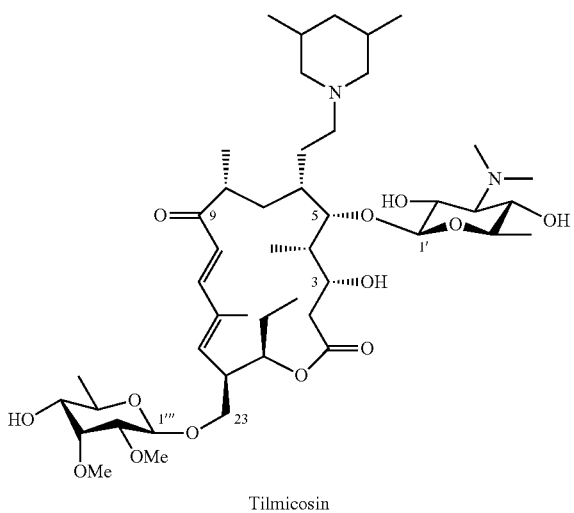

Tilmicosin

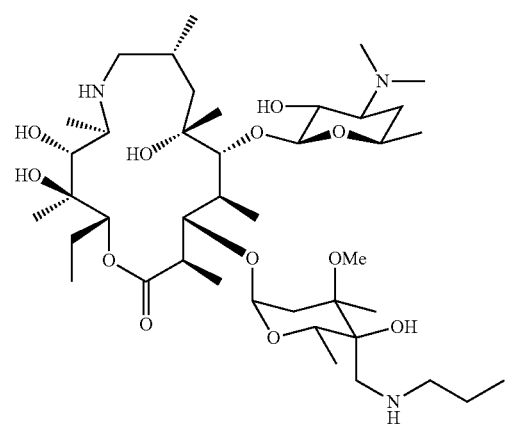

Tulathromycin

Tylosin has been used for the treatment of infections of Gram-positive bacterium and *Mycoplasma* in farm animals.

In order to further expand the spectrum of tylosin and to improve its oral bioavailability, a number of tylosin derivatives have been tested. Examples of such tylosin derivatives typically include among others tilmicosin and tulathromycin (tulathromycin belongs to a different class of compounds) represented by the following formulae, respectively:

Tilmicosin and tulathromycin are useful for the treatment of pasteurellosis caused by Gram negative *bacillus* such as *Pasteurella* or *Mannheimia*. They are the most commonly used and important antibiotics in farm animals.

However, new antibiotics are inextricably associated with the emergence of resistant bacteria. Accordingly, there is still a need to provide new antibiotics.

The backgrounds may be reflected in the following Patent and Non-patent References:

PATENT REFERENCES

WO 2009-064953
WO 2005-118610
WO 2003-089447
WO 2003-089446
WO 2003-039558
WO 2007-071370
WO 2005-118610
WO 2003-043642
WO 2003-039558
WO 1996-009312
EP 606747
EP 240264
EP 124216

NON-PATENT REFERENCES

Woodward, R. B. *Angew. Chem.* 1957, 69, 50-58.
Brockmann, H.; Henkel, W. *Naturwissenshaften.* 1950, 37, 138.
Pinnert-Sindico, S.; Ninet, L.; Preud'homme, J.; Cosar, C. Rhone-Poulenc Research Labs., Paris, *Antibiotics Ann.* 1955, 2, 1954-1955.
Hansen, J. L.; Ippolito, J. A.; Ban, N.; Nissen, P.; Moore, P. B.; Steitz, T. A. *Molecular Cell.* 2002, 10, 117.
Ducruix, A.; Pascard, C.; Nakagawa, A.; Omura, S. *J. Chem. Soc. Chem. Commun.* 1976, 947.
Morin, R. B.; Gorman, M.; Hamill, R. L. *Tetrahedron Lett.* 1970, 11, 4737-4740.
Omura, S.; Nakagawa, A.; Neszmelyi, A.; Gero, S. D.; Sepulcre, A. M.; Piriou, F.; Lukacs, G. *J. Am. Chem. Soc.* 1975, 97, 4001-4009.
McGuire, J. M. *Antibiot. Chemother.* 1961, 11, 320-327.
Debono, M.; Kirst, H. A.; Omura, S. *J. Antibiot.* 1989, 42, 1253-1267.
Shokichi Nakajima Resistant to the drugs—fight against infections—, Maruzen, Tokyo (2000)
Cattle death loss: the National Statistics Service (NASS). *United State department of Agriculture*, May, 5 (2006)
Rogert A. Smith: Impact of disease on feedlot performance: A review. *J. Anim. Sci.* 1998, 76, 276-274.
Maina, H.; John, D. B.; Ben A. *FEMS Microbiol. Lett.* 2006, 256, 1-10.
Yasutomo Arashima: Misunderstanding of "pasteurellosis" in Japan.
Kolb, H. C.; Finn, M. G.; Sharpless, K. B. *Angew. Chem., Int. Ed.* 2001, 40, 2004-2021.
Rostovtsev, V. V.; Green, L. G.; Fokin, V. V.; Sharpless, K. B. *Angew. Chem., Int. Ed.* 2002, 41, 2596-2599.
a) Huisgen, R. *Pure Apple Chem.* 1989, 61, 613-628. b) Huisgen, R. *In 1,3-Dipolar Cycloaddition Chemistry*; Padwa, A., Ed.; Wiley: New York, 1984, 1, 1-176.
a) Rostovtsev, V. V.; Green, L. G.; Fokin, V. V.; Sharpless, K. B. *Angew. Chem., Int. Ed.* 2002, 41, 2596-2599.
*Macrolide antibiotics. Chemistry, biology, and practice.* Edited by Omura, S. Academical Press, Inc., Orlando, Fla. 32887. 1984.
Hirose, T.; Sunazuka, T.; Noguchi, Y.; Yamaguchi, Y.; Hanaki, H.; Sharpless, K. B.; Omura, S. *Heterocycles,* 2006, 69, 55-61.
Kirst, H. A.; Toth, J. E.; Debono, M.; Willard, K. E.; Truedell, B. A.; Ott, J. L.; Counter, F. T.; Felty-Duckworth, A. M.; Pekarek, R. S. *J. Med. Chem.* 1988, 31, 1631-1641.
Mereu, A.; Moriggi, E.; Napoletano, M.; Regazzoni, C.; Manfredini, S.; Mercurio, T. P.; Pellacini, F. *Bioorg. Med. Chem. Lett.* 2006, 16, 5801-5804.
Rostovtsev, V. V.; Green, L. G.; Forkin, V. V.; Sharpless, K. B. *Angew. Chem., Int. Ed.* 2002, 41, 2597.
Chan, T. R.; Hilgraf, R.; Sharpless, K. B.; Fokin, V. V. *Org. Lett.* 2004, 6, 2853-2855.
Noboru Kagei: Journal of preventive medicine, 1985, 199, 32-33.
Yoshio Ueno, Satoshi Omura: "Microbial Chemistry, 2nd. edition", Nankodo (1986).
Tsuyoshi Yamada: "Fight between bacterium and human", Ishiyaku Publishers, Inc.
Satoshi Omura, Ruiko Oiwa: Chemistry and Biology, 1982, 20, 10-12.
Cassinelli, G.; Cotta, G.; D'Amico, G.; Della, B. C.; Grein, A.; Mazzoleni, R.; Ricciardi, M. L.; Tintinelli, R. *Arch. Mikrobiol.* 1970, 70, 197-210.
Bruna, D. C.; Ricciardi, M. L.; Sanfilippo, A. *Antimicrob. Agents. Chemother.* 1973, 3, 708-710.
Hamill, R. L.; Hoehn, M. M. *J. Antibiot.* 1964, 17, 100-103.
Probst, G. W.; Hoehn, M. M.; Woods, B. L. *Antimicrob. Agents. Chemother.* 1966, 789-795.
Haneisi, T.; Arai, M.; Kitano, N.; Yamamoto, S. *J. Antibiot.* 1974, 27, 339-342.
Masatoshi Inukai, Hiroshi Mishima: Current Chemistry special 9 "Advanced antibiotics", Tokyo Kagakudojin, 1987, 37-43.
a) Omura, S.; Otoguro, K.; Imamura, N.; Huga, H.; Takahashi, Y.; Masuma, R., Tanaka, Y.; Tanaka, H.; Xue-hui, S.; En-tai, Y. *J. Antibio,* 1987, 40, 623-629. b) Imamura, N.; Kuga, H.; Otoguro, K.; Tanaka, H.; Omura, S. *J. Antibio.* 1989, 42, 156-158.
Giencke, W.; Ort, O.; Stark, H. *Liebigs. Ann. Chem.* 1989. 671-676.
Moss, R. A.; Landon, M. J.; Luchter, K. M.; Mamantov, A. *J. Am. Chem. Soc.* 1972, 94, 4392-4394.
Tsuzuki, K.; Yan, F.; Otoguro, K.; Omura, S. *J. Antibiot.* 1991, 44, 774-784.
Kar, A.; Argade, N. P. *Tetrahedron,* 2003, 59, 2991.
Nam, N. H.; Kim, Y.; You, Y. J.; Hong, D. H.; Kim, H. M.; Ahn, B. Z. *Bioorg. Med. Chem. Lett.* 2002, 12, 1955-1958.
Naora, H.; Ohnuki, T.; Nakamura, A. *Bull. Chem. Soc. Jpn.* 1988, 61, 993-994.
Thakkalapally, A.; Benin, V. *Tetrahedron.* 2005, 61, 4939-4948.

SUMMARY OF THE INVENTION

The object of the present invention is to provide new chemical entities effective in the treatment or prevention of infections in animals caused by bacteria such as: *Staphylococcus* spp, *Streptococcus* spp, *Enterococcus* spp, *Neisseria* spp, *Moraxella* spp, *Corynebacterium* spp, *Lactobacillus* spp, *Bacillus* spp, *Listeria* spp, *Erysipelothrix* spp, *Arcanobacterium* spp, *Vibrio* spp *Aeromonas* spp, *Escherichia* spp, *Klebsiella* spp, *Proteus* spp, *Salmonella* spp, *Shigella* spp, *Morganella* spp, *Citrobacter* spp, *Enterobacter* spp, *Serratia* spp, *Erwinia* spp, *Yersinia* spp, *Pseudomonas* spp, *Alcaligenes* spp, *Burkholderia* spp, *Phyllobacterium* spp, *Acinetobacter* spp, *Stenotrophomonas* spp, *Haemophilus* spp, *Actinobacillus* spp, *Bordetella* spp, *Pasteurella* spp, *Brucella* spp, *Campylobacter* spp, *Capnylophaga* spp, *Francisella* spp, *Ureaplasma* spp, *Bartonella* spp, *Chlamydia* spp, *Coxiella* spp, *Ehrlichia* spp, *Rickettsia* spp, *Borrelia* spp, *Leptospira* spp, *Treponema* spp, *Brachyspira* spp, *Veillo-* nella spp, *Peptostreptococcus* spp, *Peptococcus* spp, *Bacteroides* spp, *Porphyromonas* spp, *Prevotella* spp, *Fusobacterium* spp, *Clostridium* spp, *Actinomyces* spp, *Propionibacterium* spp, *Eubacterium* spp, *Lactobacillus* spp, *Bifidobacterium* spp.

More specifically the present compounds can be used in the treatment or prevention of bacterial infections caused by gram-positive bacteria such as staphylococcal, streptococcal, *Lactobacillus acidophilus*, *Corynebacterium diphtheriae*, *Propionibacterium acnes*, *Actinomyces bovis*, *Mycobacterium tuberculosis*, *Mycobacterium leprae*, *Bacillus* or *Clostridium* and gram-negative bacteria such as *Pasteurella*, *Mannheimia* or *Mycoplasma* in animals.

In one embodiment, the present invention provides compounds represented by the formula (I):

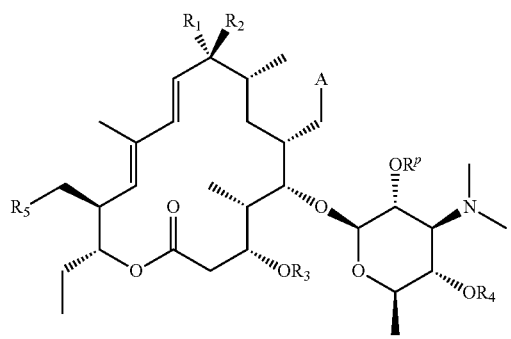

or a pharmaceutically acceptable salt, ester, prodrug or solvate thereof;
wherein, A is selected from the group consisting of:
(1) —CHO or a protected aldehyde;
(2) $CH_2$—X, wherein X is selected from the group consisting of:
a. hydroxy or protected hydroxy;
b. halogen; and
c. —$N_3$
(3) —CN;
(4) —CH=N—NR7R8, wherein R7 and R8 are each independently selected from hydrogen, C1-C6-alkyl, optionally substituted with one or more substituents selected from the group consisting of halogen, aryl, substituted aryl, heterocyclic and substituted heterocyclic, C2-C6-alkenyl, optionally substituted with one or more substituents selected from the group consisting of halogen, aryl, substituted aryl, heterocyclic and substituted heterocyclic, C2-C6-alkynyl, optionally substituted with one or more substituents selected from the group consisting of halogen, aryl, substituted aryl, heterocyclic and substituted heterocyclic or R7 and R8 taken with the nitrogen atom to which they are connected form a 3- to 7-membered ring which may optionally contain a hetero function selected from the group consisting of —O—, —NH—, —N(C1-C6-alkyl)-, —N(aryl)-, —N (heteroaryl)-, —S—, —S(O)— and —S(O)$_2$—;
(5) —CH=N—OR7, wherein R7 is as previously defined;
(6) C3-C14-cycloalkyl;
(7) substituted C3-C14-cycloalkyl;
(8) aryl;
(9) substituted aryl;
(10) heterocyclic;
(11) substituted heterocyclic; and
(12) $CH_2$—R';

R1 and R2 are each independently selected from the group consisting of:
(1) hydrogen;
(2) hydroxy;
(3) protected hydroxy;
(4) —OC(O)—C1-C12-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(5) —O—R7, where R7 is as previously defined;
(6) halogen;
(7) —NR7R8, where R7 and R8 are as previously defined;
(8) R1 and R2 taken together are oxo; and
(9) R1 and R2 taken together are =N—O—C0-C3-alkyl-R';
R3 is selected from the group consisting of:
(1) hydrogen;
(2) a hydroxy protecting group;
(3) —C(O)—C1-C12-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(4) C1-C6-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(5) C2-C6-alkenyl, optionally substituted with one or more substituents selected from the group consisting of halogen, aryl, substituted aryl, heterocyclic, substituted heterocyclic, —O—R7 and —NR7R8 where R7 and R8 are as previously defined; and
(6) C2-C6-alkynyl, optionally substituted with one or more substitutents selected from the group consisting of halogen, aryl, substituted aryl, heterocyclic, substituted heterocyclic, —O—R7 and —NR7R8 where R7 and R8 are as previously defined;
R4 is -M-Y, where M is:
(1) absent,
(2) —C(O)—,
(3) —C(O)N(R7)-, where R7 is as previously defined,
(4) —C1-C6-alkyl-N(R7)-, where R7 is as previously defined,
(5) —C2-C6-allcenyl-N(R7)-, where R7 is as previously defined, or
(6) —C2-C6-alkynyl-N(R7)-, where R7 is as previously defined; and where Y is:
(1) hydrogen,
(2) hydroxy protecting group,
(3) C1-C6-alkyl, optionally substituted with one or more substituents selected from the group consisting of halogen, aryl, substituted aryl, heterocyclic and substituted heterocyclic, —OR7 where R7 is as previously defined,
(4) C2-C6-alkenyl, optionally substituted with one or more substituents selected from the group consisting of halogen, aryl, substituted aryl, heterocyclic and substituted hetreocyclic, —OR7 where R7 is as previously defined,
(5) C2-C6-alkynyl, optionally substituted with one or more substituents selected from the group consisting of halogen, aryl, substituted aryl, heterocyclic and substituted heterocyclic, —OR7 where R7 is as previously defined,
(6) aryl,
(7) substituted aryl,
(8) heterocyclic, or
(9) substituted heterocyclic;

R5 is selected from the group consisting of:
(1) hydrogen;
(2) hydroxy;
(3) protected hydroxy;
(4) halogen;
(5) —O—R7, where R7 is as previously defined;
(6) —N₃ or R';
$R^P$ is hydrogen or a hydroxy protecting group;
and each R' is independently [1,4]-epi-[1,2,3]-triazoro-R;
and where each R is independently selected from the group consisting of:
(1) C1-C9-alkyl, optionally substituted with one or more substituents selected from the group consisting of halogen, aryl, substituted aryl, heterocyclic and substituted heterocyclic, —OR7 where R7 is as previously defined;
(2) C2-C9-alkenyl, optionally substituted with one or more substituents selected from the group consisting of halogen, aryl, substituted aryl, heterocyclic and substituted heterocyclic, —OR7 where R7 is as previously defined;
(3) C2-C9-alkynyl, optionally substituted with one or more substituents selected from the group consisting of halogen, aryl, substituted aryl, heterocyclic and substituted heterocyclic, —OR7 where R7 is as previously defined;
(4) C3-C14-cycloalkyl;
(5) substituted C3-C14-cycloalkyl;
(6) aryl;
(7) substituted aryl;
(8) heterocyclic;
(9) substituted heterocyclic; and
(10) —COOR7, where R7 is as previously defined;
provided that at least one of A, R1 and R2 and R5 comprise R'.

In one preferred embodiment, the present invention provides compounds of said formula (I), wherein;
A is selected from halogen, CH₂—N₃, hydroxy, CHO, hydroxyC₁₋₆alkyl, haloC₁₋₆alkyl, methyl(3,5-di(C1-C3-alkyl)-piperidino) and CH₂—R';
R1 and R2 taken together are oxo or =N—O—C0-C3-alkyl-R';
R3 is H;
R4 is H;
R5 is selected from hydroxy, N₃, halogen, 6-deoxy-2,3-di-O-methyl-b-d-allo-hexapyranosyloxy and R'; and
R' is as defined above;
provided that at least one of A, R1 and R2 and R5 comprises R';
or a pharmaceutically acceptable salt, ester, prodrug or solvate thereof.

In further preferred embodiment of the present invention, there are provided compounds of said formula (I), wherein;
A is CH₂—R';
R1 and R2 taken together are oxo;
R3 is H;
R4 is H; and
R5 is 6-deoxy-2,3-di-O-methyl-b-d-allo-hexapyranosyloxy.

In another preferred embodiment of the present invention, there are provided compounds of said formula (I), wherein;
A is CHO or methyl(3,5-dimethylpiperidino);
R1 and R2 taken together are oxo;
R3 is H;
R4 is H; and
R5 is R'.

In another preferred embodiment of the present invention, there are provided compounds of said formula (I), wherein;
A is CHO or methyl(3,5-dimethylpiperidino);
R1 and R2 taken together are =N—O—C0-C3-alkyl-R'; and
R3 is H;
R4 is H; and
R5 is 6-deoxy-2,3-di-O-methyl-b-d-allo-hexapyranosyloxy.

In the present invention, R is preferably selected from the group consisting of

-continued

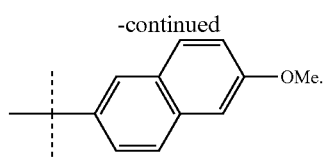

In another embodiment, the present invention provides a method for preparing a compound of the formula (I):

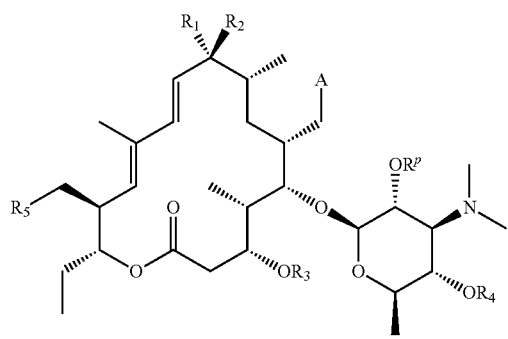

(I)

wherein A is CH$_2$—R' and R1, R2, R3, R4, R5, R' and R$^p$ are as defined above;
which method comprises following steps:
(i) reacting a compound of the formula (II):

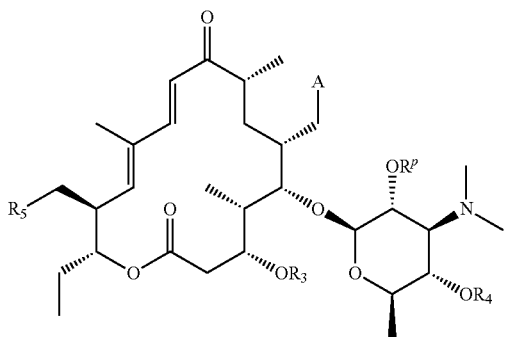

(II)

wherein,
A is CH$_2$-hydroxy; and
the other variable groups are as defined in the formula (I), with an azide selected from diphenylphosphoryl azide (DPPA) or sodium azide (NaN$_3$) to form a compound of said formula (II) wherein A is CH$_2$—N$_3$ and the other variable groups are as defined in the formula (I); and
(ii) reacting the resulting compound of the formula (II) wherein A is CH$_2$—N$_3$ and the other variable groups are as defined in the formula (I) with an R—C≡CH, wherein R is as defined in the formula (I) above, in the presence of a copper catalyst to form a compound of the formula (II), wherein A is CH$_2$—R' and R3, R4, R5, R' and R$^p$ are as defined above.

In another embodiment, the present invention provides a method for preparing a compound of the formula (I):

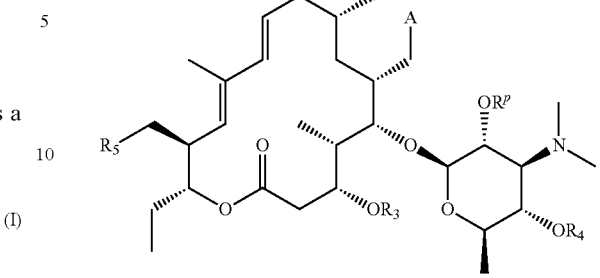

(I)

wherein R5 is R' and A, R1, R2, R3, R4, R' and R$^p$ are as defined above; which method comprises following steps:
(i) reacting a compound of the formula (II):

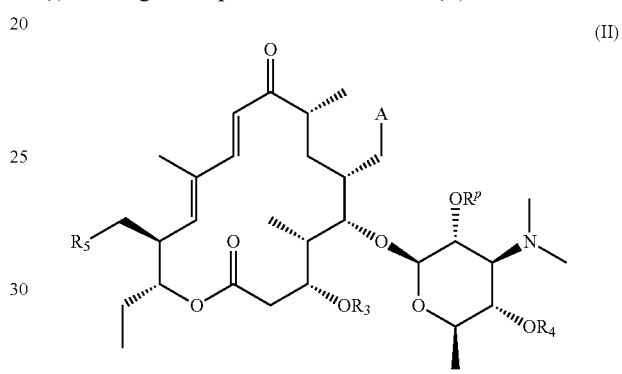

(II)

wherein,
R5 is hydroxy; and
the other variable groups are as defined in the formula (I), with an azide selected from diphenylphosphoryl azide (DPPA) or sodium azide (NaN$_3$) to form a compound of said formula (II) wherein R5 is —N$_3$ and the other variable groups are as defined in the formula (I); and
(ii) reacting the resulting compound of the formula (II) wherein R5 is —N$_3$ and the other variable groups are as defined in the formula (I) with an R—C≡CH, wherein R is as defined in the formula (I) above, in the presence of a copper catalyst to form a compound of the formula (II), wherein R5 is R' and A, R3, R4, R' and R$^p$ are as defined above.

In still another embodiment, the present invention provides a method for preparing a compound of the formula (I):

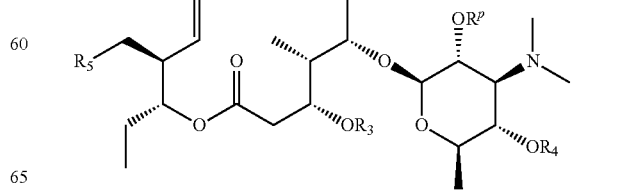

(I)

wherein R1 and R2 taken together are =N—O—C0-C3-alkyl-R' and A, R3, R4, R5, R' and R$^p$ are as defined above; which method comprises following steps:
(i) reacting a compound of the formula (II):

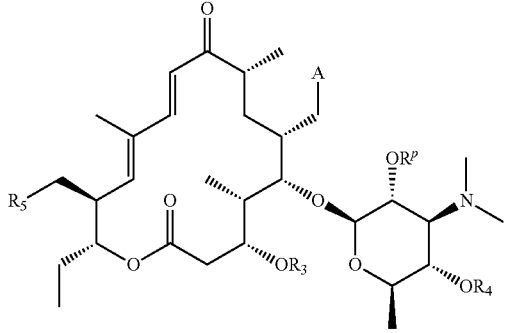

(II)

wherein,
the variable groups are as defined in the formula (I), but A is not —CHO, with a CH≡C—(CH$_2$)$_n$—O—NH$_2$.HCl wherein n is an integer from 1 to 3 to form a compound of the formula (III):

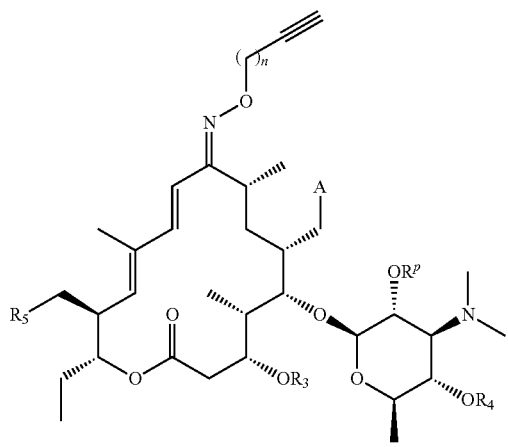

(III)

wherein n is an integer from 1 to 3 and A, R3, R4, R5 and R$^p$ are as defined in formula (I), but A is not —CHO; and
(ii) reacting the compound of the formula (III) resulting from step (i) or (ii) with an R—N$_3$, wherein R is as defined in formula (I) above, in the presence of a copper catalyst to form a compound of the formula (I):

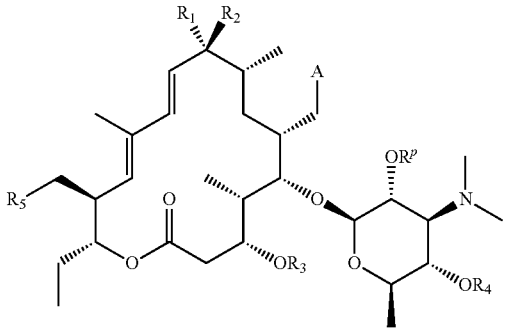

(I)

wherein R1 and R2 taken together are =N—O—C0-C3-alkyl-R' and A, R3, R4, R5, R' and R$^p$ are as defined above.

In further embodiment, the present invention provides a pharmaceutical or veterinary composition comprising the compound of the present invention. Such composition may be used for the treatment or the prevention of bacterial infections or disorders associated with bacterial infections in animals, which include among others mammal, fish or birds. The pharmaceutical or veterinary composition may include or may be used simultaneously, sequentially or contiguously with one or more other antibiotics.

In further embodiment, the present invention provides use of the compound of the present invention for manufacturing a medicament for treatment or prevention of bacterial infections or disorders associated with bacterial infections in animals.

The compounds of the present invention has different chemical structure from tylosin or tilmicosin, while the present compounds may have antibacterial activities similar to or greater than those of tylosin or tilmicosin. Therefore, the compounds of the present invention may be used as a substitute for tylosin or tilmicosin, particularly to treat infections or related disorders caused by tylosin- or tilmicosin-resistant bacteria. Accordingly, the compound of the present invention is useful in the treatment or prevention of bacterial infections or disorders associated with bacterial infections in animals.

DETAILED DESCRIPTION OF THE PREFERRED EMBODIMENTS

The terms as used herein have the meaning as defined below or as understood by an artisan of ordinary skill in fields of organic chemistry, biochemistry, medical sciences, pharmaceutical sciences, bacteriology and the like.

The terms "C1-C3-alkyl", "C1-C6-alkyl", "C1-C12-alkyl" or the like, as used herein, refer to saturated, straight- or branched-chain hydrocarbon radicals containing between one and three, one and six or one and twelve carbon atoms, respectively. The term "C0-C3-alkyl" means a bond or C1-C3-alkyl. Examples of C1-C3-alkyl radicals include methyl, ethyl, propyl and isopropyl, and examples of C1-C6-alkyl radicals include, but are not limited to, methyl, ethyl, propyl, isopropyl, n-butyl, tert-butyl, neopentyl and n-hexyl, and examples of C1-C12-alkyl radicals include, but are not limited to, methyl, ethyl, propyl, isopropyl, n-butyl, tert-butyl, neopentyl, n-hexyl, n-octyl, n-decyl and n-dodecyl.

The term "C2-C6-alkenyl" or the like, as used herein, refers to straight- or branched-chain hydrocarbon radicals containing between two and six carbon atoms with one or more double bonds in the chain. Examples of C2-C6-alkenyl include, but are not limited to, propenyl, isobutenyl, 1,3-hexadienyl, n-hexenyl and 3-pentenyl.

The term "C2-C6-alkynyl" or the like, as used herein, refers to straight- or branched-chain hydrocarbon radicals containing between two and six carbon atoms with one or more triple bonds in the chain optionally containing one or more double bond. Examples of C2-C6-alkynyl include, but are not limited to, propynyl, isopentynyl, 1,3-hexadiynyl, n-hexynyl, 3-pentynyl, and 1-hexen-3-ynyl.

The term "aryl", as used herein, refers to unsubstituted carbocyclic mono-, di- or tri-cyclic aromatic groups including, but not limited to, phenyl, 1- or 2-naphthyl, anthracene, phenanthrene and the like.

The term, "C3-C14-cycloalkyl", as used herein refer to unsubstituted mono-, di- or tri-cyclic groups where each carbocyclic ring consisting cycloalkyl comprises 3 to 7 carbon atoms, respectively, such as for example, cyclopropyl, cyclobutyl, cyclopentyl, cyclohexyl, and cycloheptyl.

The terms "halo" and "halogen", as used herein, refer to an atom selected from fluorine, chlorine, bromine and iodine.

The term "heteroaryl", as used herein, refers to a mono-, di- or tri-cyclic aromatic radical having from five to fourteen ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl", as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to one or two benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic", as used herein, refers to heterocycloalkyl and heteroaryl.

The term "substituted heterocyclic", as used herein, refers to substituted heterocycloalkyl and substituted heteroaryl.

The term "substituted aryl", as used herein refers to an aryl group, as defined herein, substituted by independent replacement of one or more of the hydrogen atoms therein with, for example, but not limited to, F, Cl, Br, I, OH, $NO_2$, CN, C(O)—C1-C6-alkyl, C(O)-aryl, C(O)-heteroaryl, $CO_2$-alkyl, $CO_2$-aryl, $CO_2$-heteroaryl, $CONH_2$, CONH—C1-C6-alkyl, CONH-aryl, CONH-heteroaryl, OC(O)—C1-C6-alkyl, OC(O)-aryl, OC(O)-heteroaryl, $OCO_2$-alkyl, $OCO_2$-aryl, $OCO_2$-heteroaryl, $OCONH_2$, OCONH—C1-C6-alkyl, OCONH-aryl, OCONH-heteroaryl, NHC(O)—C1-C6-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—C1-C6-alkyl, NHCONH-aryl, NHCONH-heteroaryl, $SO_2$—C1-C6-alkyl, $SO_2$-aryl, $SO_2$-heteroaryl, $SO_2NH_2$, $SO_2NH$—C1-C6-alkyl, $SO_2NH$-aryl, $SO_2NH$-heteroaryl, C1-C6-alkyl, C3-C7-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, substituted aryl, heteroaryl, substituted heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted heteroaryl", as used herein refers to a heteroaryl group as defined herein substituted by independent replacement of one or more of the hydrogen atoms therein with, for example, but not limited to, F, Cl, Br, I, OH, $NO_2$, CN, C(O)—C1-C6-alkyl, C(O)-aryl, C(O)-heteroaryl, $CO_2$-alkyl, $CO_2$-aryl, $CO_2$-heteroaryl, $CONH_2$, CONH—C1-C6-alkyl, CONH-aryl, CONH-heteroaryl, OC(O)—C1-C6-alkyl, OC(O)-aryl, OC(O)-heteroaryl, $OCO_2$-alkyl, $OCO_2$-aryl, $OCO_2$-heteroaryl, $OCONH_2$, OCONH—C1-C6-alkyl, OCONH-aryl, OCONH-heteroaryl, NHC(O)—C1-C6-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—C1-C6-alkyl, NHCONH-aryl, NHCONH-heteroaryl, $SO_2$—C1-C6-alkyl, $SO_2$-aryl, $SO_2$-heteroaryl, $SO_2NH_2$, $SO_2NH$—C1-C6-alkyl, $SO_2NH$-aryl, $SO_2NH$-heteroaryl, C1-C6-alkyl, C3-C7-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted heterocycloalkyl", as used herein, refers to a heterocycloalkyl group, as defined above, substituted by independent replacement of one or more of the hydrogen atoms therein with, for example, but not limited to, F, Cl, Br, I, OH, $NO_2$, CN, C(O)—C1-C6-alkyl, C(O)-aryl, C(O)-heteroaryl, $CO_2$-alkyl, $CO_2$-aryl, $CO_2$-heteroaryl, $CONH_2$, CONH—C1-C6-alkyl, CONH-aryl, CONH-heteroaryl, OC(O)—C1-C6-alkyl, OC(O)-aryl, OC(O)-heteroaryl, $OCO_2$-alkyl, $OCO_2$-aryl, $OCO_2$-heteroaryl, $OCONH_2$, OCONH—C1-C6-alkyl, OCONH-aryl, OCONH-heteroaryl, NHC(O)—C1-C6-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—C1-C6-alkyl, NHCONH-aryl, NHCONH-heteroaryl, $SO_2$—C1-C6-alkyl, $SO_2$-aryl, $SO_2$-heteroaryl, $SO_2NH_2$, $SO_2NH$—C1-C6-alkyl, $SO_2NH$-aryl, $SO_2NH$-heteroaryl, C1-C6-alkyl, C3-C7-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted cycloalkyl", as used herein, refers to a cycloalkyl group, as defined above, substituted by independent replacement of one or more of the hydrogen atoms therein with, for example, but not limited to, F, Cl, Br, I, OH, $NO_2$, CN, C(O)—C1-C6-alkyl, C(O)-aryl, C(O)-heteroaryl, $CO_2$-alkyl, $CO_2$-aryl, $CO_2$-heteroaryl, $CONH_2$, CONH—C1-C6-alkyl, CONH-aryl, CONH-heteroaryl, OC(O)—C1-C6-alkyl, OC(O)-aryl, OC(O)-heteroaryl, $OCO_2$-alkyl, $OCO_2$-aryl, $OCO_2$-heteroaryl, $OCONH_2$, OCONH—C1-C6-alkyl, OCONH-aryl, OCONH-heteroaryl, NHC(O)—C1-C6-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—C1-C6-alkyl, NHCONH-aryl, NHCONH-heteroaryl, $SO_2$—C1-C6-alkyl, $SO_2$-aryl, $SO_2$-heteroaryl, $SO_2NH_2$, $SO_2NH$—C1-C6-alkyl, $SO_2NH$-aryl, $SO_2NH$-heteroaryl, C1-C6-alkyl, C3-C7-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "amino" includes a group represented by —$NH_2$. The term "substituted amino" indicates amino groups having one or two substituents in place of one or two hydrogen atoms attached to nitrogen atom of the amino group. The term "azide" means a group represented by —$N_3$, which may comprise —N—N≡N or —N=N=N.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, Protective Groups in Organic Synthesis, 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy", refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group", as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G, M, Wuts, Protective Groups in Organic Synthesis, op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, dimethoxy methyl, 1,3-dioxolane, 1,3-dioxane and the like.

The compound of the present invention can be prepared, but is not limited to, by any conventional method known to an artisan of ordinary skill, for example according to any one of the methods described below, typically analogous to the method detailed in Examples of the present specification.

The preparation of the present compound can be performed typically by using cycloaddition reaction between azide and acetylene derivative, what is called click chemistry (see, for example Kolb, H. C.; Finn, M. G.; Sharpless, K. B., Angew. Chem., Int. Ed. 2001, 40, 2004-2021 and Rostovtsev, V. V.; Green, L. G.; Fokin, V. V.; Sharpless, K. B., Angew. Chem., Int. Ed. 2002, 41, 2596-2599). The mechanism of the reaction is represented by the following scheme A:

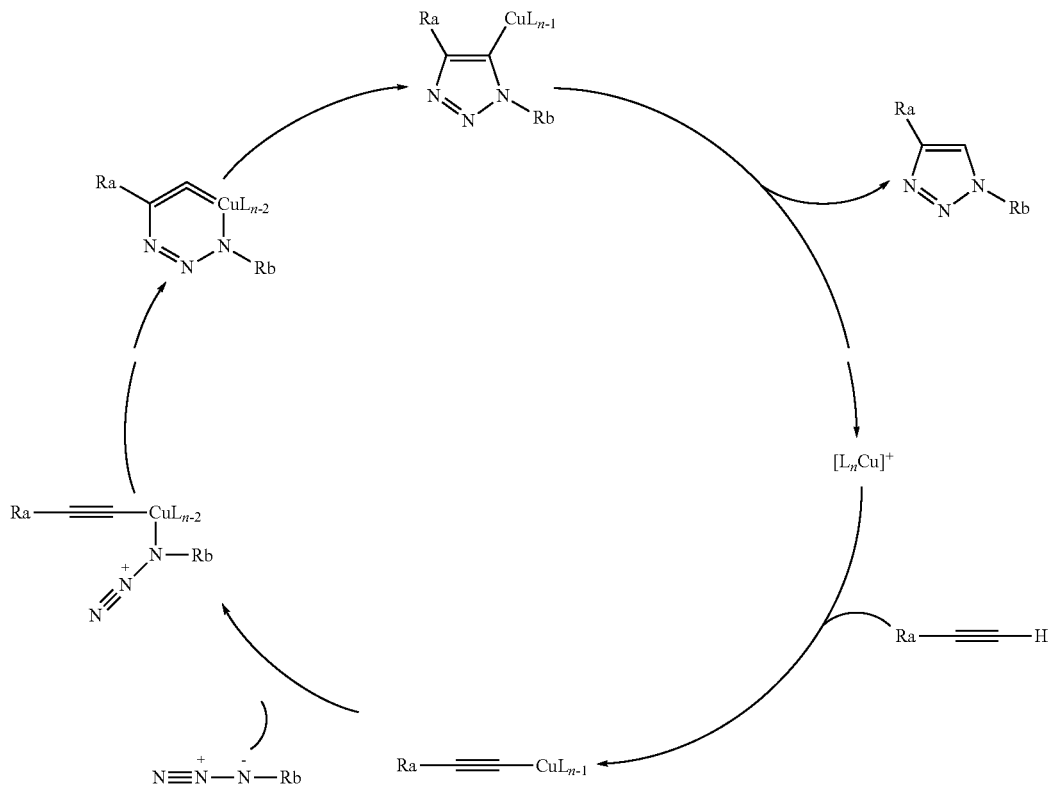

wherein Ra and Rb indicate any functional groups and LnCu indicates copper catalysis. The click chemistry may be typically characterized by sophisticated functional group selectivity and regio selectivity, mild reaction condition, high yield, and applicability for a wide variety of substituents.

In one embodiment, the present invention provides a method for preparing a compound of the formula (I):

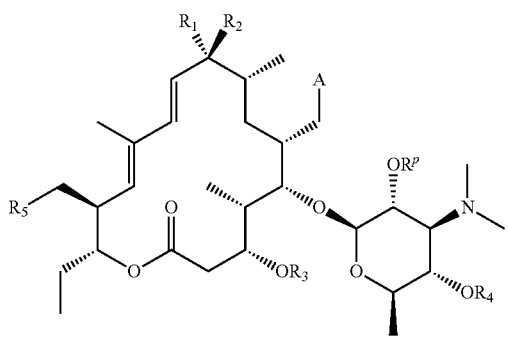
(I)

wherein A is CH$_2$—R' and R1, R2, R3, R4, R5, R' and R$^P$ are as defined above;
which method comprises following steps:
(i) reacting a compound of the formula (II):

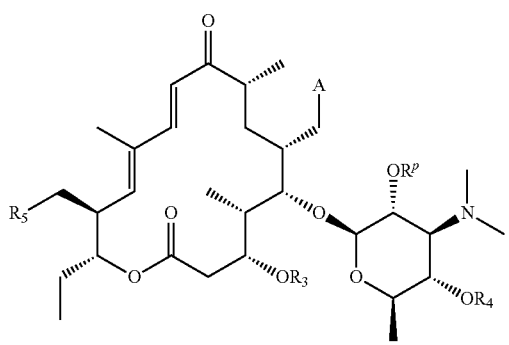
(II)

wherein,
A is CH$_2$-hydroxy; and
the other variable groups are as defined in the formula (I), with an azide selected from diphenylphosphoryl azide (DPPA) or sodium azide (NaN$_3$) to form a compound of said formula (II) wherein A is CH$_2$—N$_3$ and the other variable groups are as defined in the formula (I); and
(ii) reacting the resulting compound of the formula (II) wherein A is CH$_2$—N$_3$ and the other variable groups are as defined in the formula (I) with an R—C≡CH, wherein R is as defined in the formula (I) above, in the presence of a copper catalyst to form a compound of the formula (II), wherein A is CH$_2$—R' and R3, R4, R5, R' and R$^P$ are as defined above.

In another embodiment, the present invention provides a method for preparing a compound of the formula (I):

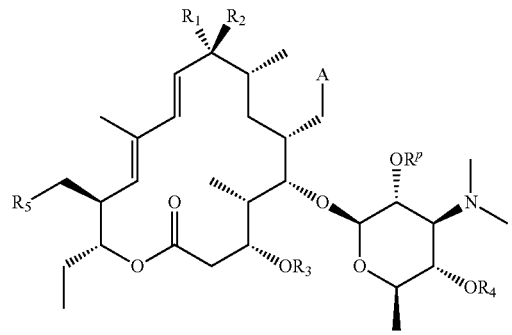
(I)

wherein R5 is R' and A, R1, R2, R3, R4, R' and R$^P$ are as defined above;
which method comprises following steps:
(i) reacting a compound of the formula (II):

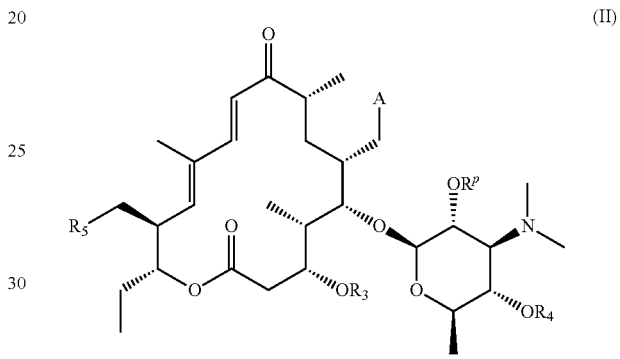
(II)

wherein,
R5 is hydroxy; and
the other variable groups are as defined in the formula (I), with an azide selected from diphenylphosphoryl azide (DPPA) or sodium azide (NaN$_3$) to form a compound of said formula (II) wherein R5 is —N$_3$ and the other variable groups are as defined in the formula (I); and
(ii) reacting the resulting compound of the formula (II) wherein R5 is —N$_3$ and the other variable groups are as defined in the formula (I) with an R—C≡CH, wherein R is as defined in the formula (I) above, in the presence of a copper catalyst to form a compound of the formula (II), wherein R5 is R' and A, R3, R4, R' and R$^P$ are as defined above.

In the step (i) of those methods for preparing the present compound of formula (I), the starting materials are commercially available or can be easily prepared a compound commercially available according to any know method. For example, the starting compound of the formula:

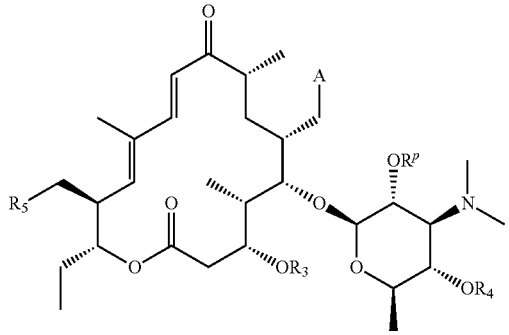
(II)

wherein,
A is $CH_2$-hydroxy; and
the other variable groups are as defined in the formula (I),
can be prepared by performing following sub-steps:
(a) deglycosylation of tylosin under acidic condition, for example in the presence of HCl aq.;
(b) reducing aldehyde group at 20-position in the presence of a reducing agent, such as $NaBH_4$; and
(c) optionally converting the remaining functional groups to desired substituents according to any conventional process.

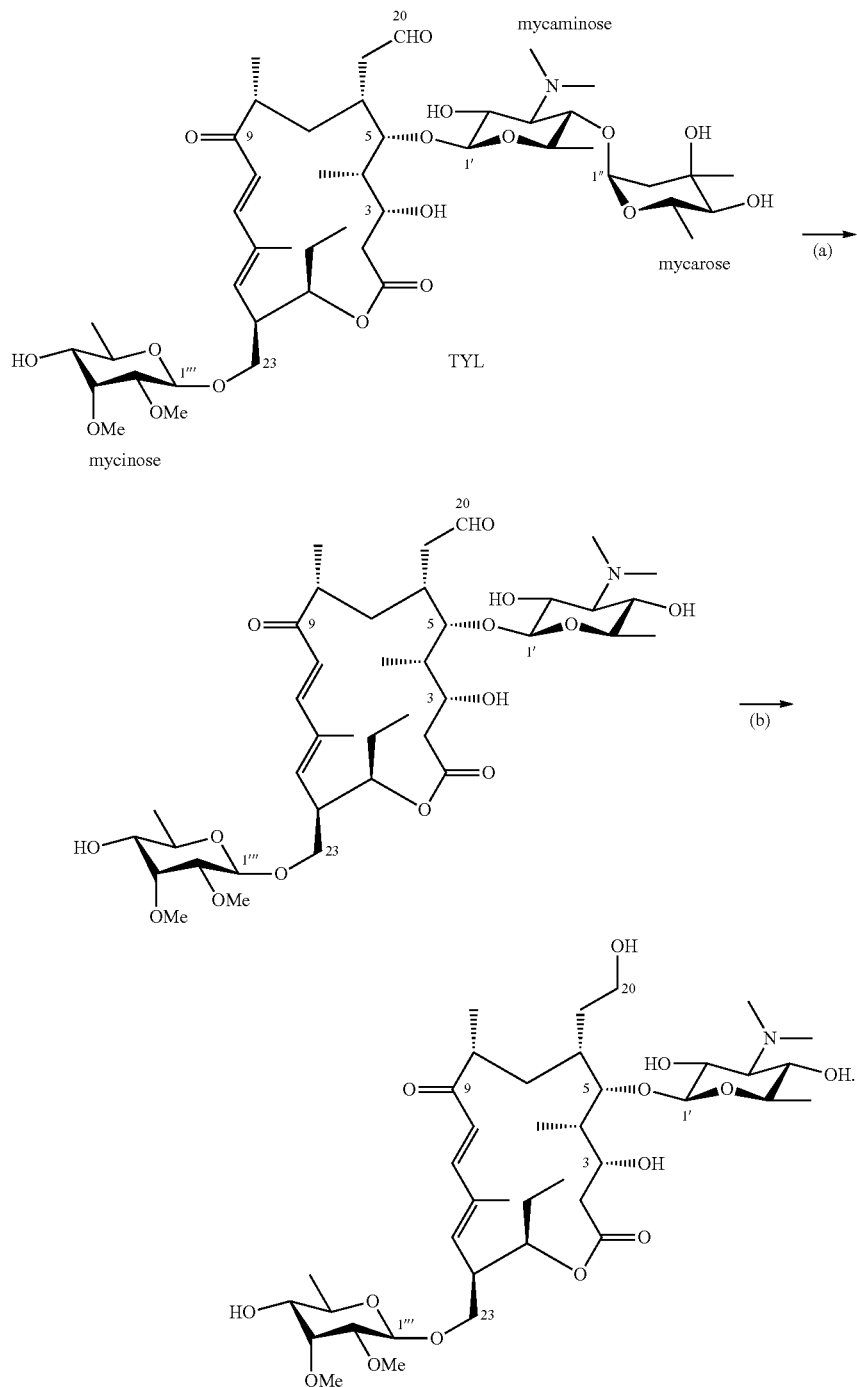

The starting compound of the formula:

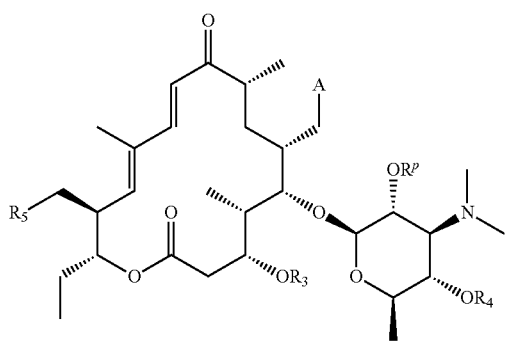

(II)

wherein,
R5 is hydroxy; and
the other variable groups are as defined in the formula (I), can be prepared by performing, for example following sub-steps:
(a) deglycosylation of tylosin under acidic condition, for example in the presence of TFA aq. or HBr; and
(b) optionally converting the remaining functional groups to desired substituents according to any conventional process.

desired, be halogenized, for example with a halogenating agent such as $I_2$ or $CCl_4$ in the presence of $PPh_3$ in a solvent such as pyridine and/or dichloromethyl at −27 to 40° C., preferably 0° C. to rt, so that a compound of formula (II) wherein A is $CH_2$-halo or R5 is halogen is formed.

By using a compound of formula (II) wherein either A is $CH_2$—R' or R5 is R', which compound may be obtained from any of the preparing methods described above as a starting material, 20,23-bistriazole tylosin derivative, that is a compound of the formula (I) wherein A is $CH_2$—R' and R5 is R' may be prepared by carrying out the other preparing method as described above.

In a detailed embodiment, the azidation of step (i) in the preparing methods above can be carried out by reacting azide such as diphenylphosphoryl azide (DPPA) or sodium azide ($NaN_3$) with the starting material in the presence of solvent such as THF or DMSO at −27 to 100° C., preferably at 0 to 80° C.

The reaction of step (ii) in the preparing methods above can be carried out in a solvent for example water, tert-butyl alcohol, methanol or acetonitrile or combination thereof, preferably in acetonitrile, preferably in the presence of tris[(1-benzyl-1H-1,2,3-triazol-4-yl)methyl]amine (TBTA), in the presence of a copper catalysis for example $CuSO_4.5H_2O$, $CuOTf.C_6H_6$, $[Cu(NCCH_3)_4][PF_6]$ or CuI, preferably CuI at 0 to 100° C., preferably 10 to 40° C., more preferably rt.

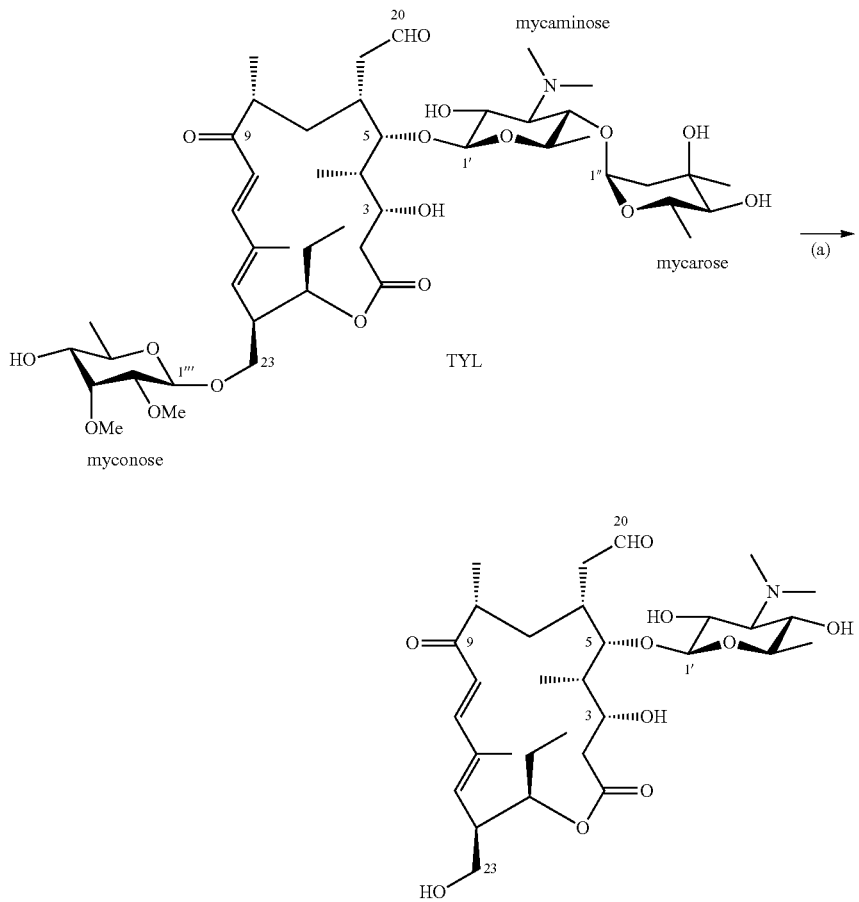

To enhance the reactivity of the 20- or 23-hydroxyl functional group, the starting compounds of formula (II) may, if In still another embodiment, the present invention provides a method for preparing a compound of the formula (I):

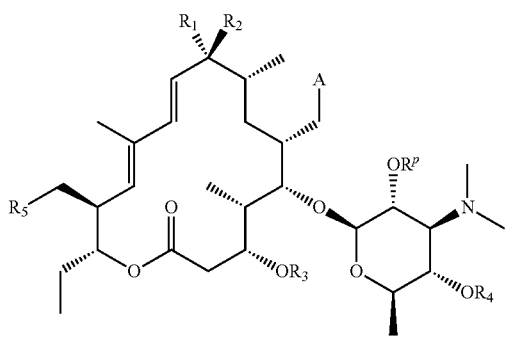

(I)

wherein R1 and R2 taken together are =N—O—C0-C3-alkyl-R' and A, R3, R4, R5, R' and $R^p$ are as defined above; which method comprises following steps:
(i) reacting a compound of the formula (II):

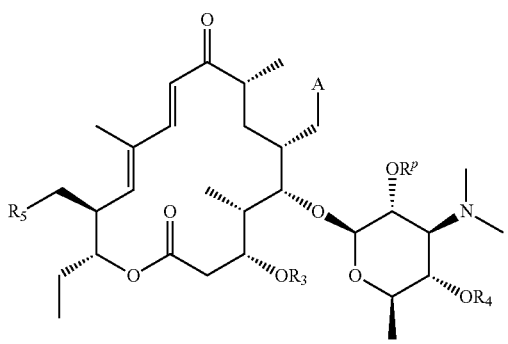

(II)

wherein,
the variable groups are as defined in the formula (I), but A is not —CHO, with a CH≡C—(CH$_2$)$_n$—O—NH$_2$.HCl wherein n is an integer from 1 to 3 to form a compound of the formula (III):

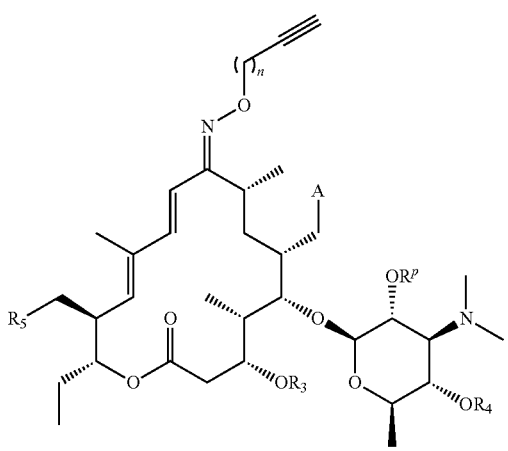

(III)

wherein n is an integer from 1 to 3 and A, R3, R4, R5 and $R^p$ are as defined in formula (I), provided that A is not —CHO; and (ii) reacting the compound of the formula (III) resulting from step (i) or (ii) with an R—N$_3$, wherein R is as defined in formula (I) above, in the presence of a copper catalyst to form a compound of the formula (I):

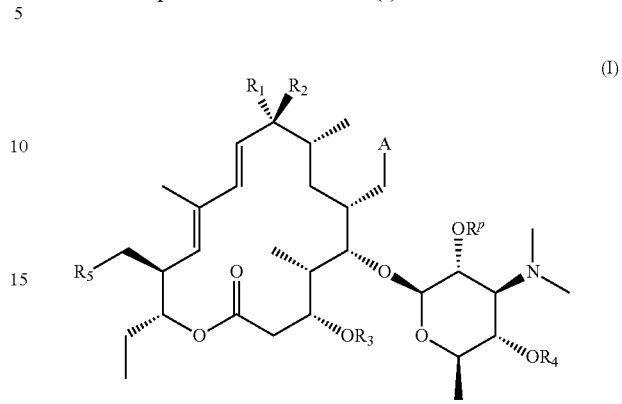

(I)

wherein R1 and R2 taken together are =N—O—C0-C3-alkyl-R' and A, R3, R4, R5, R' and $R^p$ are as defined above.
The starting compound of the formula (II):

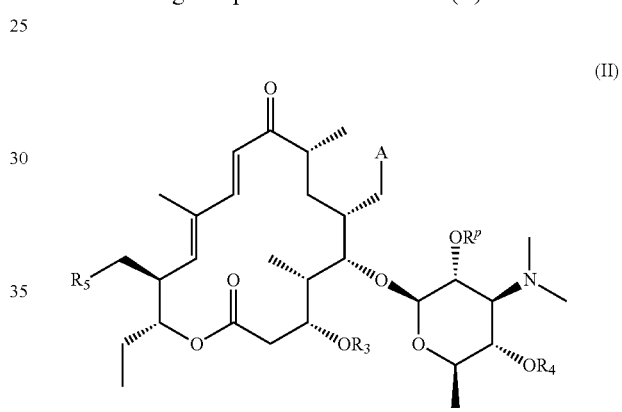

(II)

wherein,
the variable groups are as defined in the formula (I), but A is not —CHO can be readily available or prepared according to any conventional process known to the skilled person.

In a detailed embodiment, the introduction of an acetylene moiety of step (i) can be carried out by reacting a CH≡C—(CH$_2$)n-O—NH$_2$.HCl (wherein n is as defined above) with the starting material in a solvent such as pyridine or methanol or combination thereof, preferably in the combination of pyridine and methanol, at 0 to 80° C., preferably rt to 65° C. If desired, an oxo or hydroxyl group which is desired not to participate in the introduction of an acetylene moiety can be protected by any conventional process.

In a detailed embodiment, the reaction of step (ii) can be carried out in solvent, for example water, tert-butyl alcohol, methanol or acetonitrile or combination thereof, preferably in acetonitrile, preferably in the presence of tris[(1-benzyl-1H-1,2,3-triazol-4-yl)methyl]amine (TBTA), in the presence of copper catalyst, for example CuSO$_4$.5H$_2$O, CuOTf.C$_6$H$_6$, [Cu(NCCH$_3$)$_4$][PF$_6$] or CuI, preferably CuI at 0 to 100° C., preferably 10 to 40° C., more preferably rt.

The compounds represented by R—N$_3$ and R—C≡CH are commercially available or can be easily prepared by any conventional procedure known to a skilled person.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the iso electric point, e.g., with weak bases, or by treatment with ion exchangers.

Intermediates and final products can be worked up and/or purified according to standard methods, e.g., using chromatographic methods, distribution methods, (re-) crystallization, and the like. The compounds, including their salts, may also be obtained in the form of solvates, in particular hydrates. In the context of the invention, solvates refer to those forms of the compounds according to the invention which, in the solid or liquid state, form a complex by coordination with solvent molecules. Hydrates are a specific form of the solvates in which the coordination is with water. Crystals of the present compounds may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

This invention also encompasses pharmaceutical or veterinary compositions containing, and methods of treating bacterial infections through administering, pharmaceutically acceptable prodrugs of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently bound through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demo sine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

The compound of the present invention has valuable pharmacological properties and thus it can be used for the treatment of diseases. In one embodiment, the compound of the present invention may be used for the treatment or prevention of bacterial infections or disorders associated with bacterial infections in animals, for example mammals, fish or birds.

The term "animal", "patient" or "subject" as used herein is used interchangeably. The term animal typically includes, but is not limited to animals suffering from, at risk of suffering from, or potentially capable of suffering from a bacterial infection, for example humans, cattle, horses, chickens, pigs, sheep, goats, dogs, apes, cats, mice, rabbits, rats, etc.; especially farm animals such as cattle, pigs and poultry.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. The compounds of the present invention are useful for treating infections caused by bacteria such as: *Staphylococcus* spp, *Streptococcus* spp, *Enterococcus* spp, *Neisseria* spp, *Moraxella* spp, *Corynebacterium* spp, *Lactobacillus* spp, *Bacillus* spp, *Listeria* spp, *Erysipelothrix* spp, *Arcanobacterium* spp, *Vibrio* spp *Aeromonas* spp, *Escherichia* spp, *Klebsiella* spp, *Proteus* spp, *Salmonella* spp, *Shigella* spp, *Morganella* spp, *Citrobacter* spp, *Enterobacter* spp, *Serratia* spp, *Erwinia* spp, *Yersinia* spp, *Pseudomonas* spp, *Alcaligenes* spp, *Burkholderia* spp, *Phyllobacterium* spp, *Acinetobacter* spp, *Stenotrophomonas* spp, *Haemophilus* spp, *Actinobacillus* spp, *Bordetella* spp, *Pasteurella* spp, *Brucella* spp, *Campylobacter* spp, *Capnylophaga* spp, *Francisella* spp, *Helicobacter* spp, *Legionella* spp, *Mycoplasma* spp, *Ureaplasma* spp, *Bartonella* spp, *Chlamydia* spp, *Coxiella* spp, *Ehrlichia* spp, *Rickettsia* spp, *Borrelia* spp, *Leptospira* spp, *Treponema* spp, *Brachyspira* spp, *Veillonella* spp, *Peptostreptococcus* spp, *Peptococcus* spp, *Bacteroides* spp, *Porphyromonas* spp, *Prevotella* spp, *Fusobacterium* spp, *Clostridium* spp, *Actinomyces* spp, *Propionibacterium* spp, *Eubacterium* spp, *Lactobacillus* spp, *Bifidobacterium* spp.

More specifically the present compounds can be used in the treatment or prevention of bacterial infections caused by gram-positive bacteria such as staphylococcal, streptococcal, *Lactobacillus acidophilus*, *Corynebacterium diphtheriae*, *Propionibacterium acnes*, *Actinomyces bovis*, *Mycobacterium tuberculosis*, *Mycobacterium leprae*, *Bacillus* or *Clostridium* or gram-negative bacteria such as *Pasteurella*, *Mannheimia* or *Mycoplasma* infections in animals.

Such bacterial infections and disorders related to such infections include, but are not limited to, the following: acne, rosacea, skin infection, pneumonia, otitis media, sinusitus, bronchitis, tonsillitis, and mastoiditis related to infection by *Streptococcus pneumoniae*, *Haemophilus influenzae*, *Moraxella catarrhalis*, *Staphylococcus aureus*, *Peptostreptococcus* spp. or *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae*, *Legionella pneumophila*, *Streptococcus pneumoniae*, *Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis*, *S. hemolyticus*, etc.), *S. pyogenes*, *S. agalactiae*, Streptococcal groups C—F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; sexually transmitted diseases related to infection by *Chlamydia trachomatis*, *Haemophilus ducreyi*, *Treponema pallidum*, *Ureaplasma urealyticum*, or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis*, *N. gonorrhoeae*, *S. aureus*, *S. pneumoniae*, *S. pyogenes*, *H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp., odontogenic infection related to infection by viridans streptococci; persistent cough related to infection by *Bordetella pertussis*; gas gangrene related to infection by *Clostridium perfringens* or *Bacteroides* spp.; Skin infection by *S. aureus*, *Propionibacterium* acne; atherosclerosis related to infection by *Helicobacter pylori* or *Chlamydia pneumoniae*; or the like.

Further bacterial infections and disorders related to such infections that may be treated or prevented in animals include, but are not limited to, the following: bovine respiratory disease related to infection by *P. haemolytica.*, *P. multocida*, *Mycoplasma bovis*, or *Bordetella* spp.; cow enteric disease related to infection by *E. coli* or protozoa (i.e., coccidia, cryptosporidia, etc.), dairy cow mastitis related to infection by *S. aureus*, *S. uberis*, *S. agalactiae*, *S. dysgalactiae*, *Klebsiella* spp., *Corynebacterium*, or *Enterococcus* spp.; swine respiratory disease related to infection by *A. pleuropneumoniae*, *P. multocida*, or *Mycoplasma* spp.; swine enteric disease related to infection by *E. coli*, *Lawsonia intracellularis*, *Salmonella* spp., or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*, cow premature abortion related to infection by protozoa (i.e., neosporium); urinary tract infection in dogs and cats related to infection by *E. coli*; skin and soft tissue infections in dogs and cats related to infection by *S. epidermidis*, *S. intermedius*, coagulase neg. *Staphylococcus* or *P. multocida*; dental or mouth infections in dogs and goats related to infection by *Alcaligenes* spp., *Bacteroides* spp., *Clostridium* spp., *Enterobacter* spp., *Eubacterium* spp., *Pep-* tostreptococcus spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., *Trichomonas* spp. or *Prevotella* spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996). The compounds of the present invention is especially effective to respiratory diseases such as pasteurellosis caused by Gram negative *bacillus* such as *Pasteurella* or *Mannheimia* in farm animals such as cows.

Accordingly, in a certain embodiment, the present invention provides a pharmaceutical or veterinary composition comprising any of the compound of the present invention. The composition may comprise therapeutically effective amount of the compound of the present invention, and if desired one or more pharmaceutically acceptable excipients or carriers.

The language "therapeutically effective amount" of the compound is that amount necessary or sufficient to treat or prevent a bacterial infection, e.g. prevent the various morphological and somatic symptoms of a bacterial infection, and/or a disease or condition described herein. In an example, an effective amount of the compound of the invention is the amount sufficient to treat a bacterial infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical or veterinary compositions for use in the treatment of these diseases. Methods of use of compounds of the present invention in the treatment of these diseases, or pharmaceutical or veterinary preparations comprising compounds of the present invention for the treatment of these diseases are also included in embodiments of the present invention.

The language "pharmaceutical or veterinary composition" includes preparations suitable for administration to mammals, e.g., farm animals such as cows. When the compounds of the present invention are administered as pharmaceuticals to mammals, e.g., cows, they can be given per se or as a pharmaceutical or veterinary composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

Formulations of the present invention include those known in the art. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Methods of preparing these formulations or compositions are also known in the art.

The term "treat," "treated," "treating" or "treatment" includes the diminishment or alleviation of at least one symptom associated or caused by the state, disorder or disease being treated. In certain embodiments, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

These compounds may be administered to humans and other animals for therapy by any suitable route of administration.

Regardless of the route of administration selected, the compounds of the present invention, which may be used in a suitable hydrated form, and/or the pharmaceutical or veterinary compositions of the present invention, are formulated into pharmaceutically acceptable dosage forms by conventional methods known to those of skill in the art.

Actual dosage levels of the active ingredients in the pharmaceutical or veterinary compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical or veterinary composition required. For example, the physician or veterinarian could start doses of the compounds of the invention employed in the pharmaceutical or veterinary composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical or veterinary composition.

The antibacterial activity by the compounds of the present invention may be measured using a number of assays available in the art. An example of such an assay is the standard minimum inhibitory concentration (MIC) test conducted according to CSLI guidelines or paper disc test conducted according to Examples below.

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

EXAMPLES

All starting materials, building blocks, reagents, acids, bases, solvents, and catalysts, etc. utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21).

Analytical Methods

Infrared (IR) absorption spectra were determined by using Horiba FT-210 spectrometer.

$^1$H NMR spectra were determined by using JEOL JNM-EX270 MHz), VALIAN-400 NMR System (400 MHz). $^{13}$C NMR spectra were determined by using JEOL JNM-EX270 (67.5 MHz), VARIAN-400 NMR system (100 MHz). Chemical shifts are indicated in δ (ppm) and coupling patterns are indicated by using following abbreviations: s: singlet; d: double; dd: double doublet; t: triplet; q: quartet; m: multiplet; br.d: broad doublet; br.dd: broad double doublet; br.dt: broad double triplet.

Low-resolution mass spectra (LC-MS) were determined by using JEOL JMS-DX300 Mass Spectrometer. High-resolution mass spectra (HRMS) were determined by using JEOL JMS-700 V Mass Spectrometer.

A thin-layer chromatography (TLC) was performed by using silica gel 60 $F_{254}$ (Merck) and compounds were detected by using UV irradiation (254 nm) or color development of phosphomolybden.

Column chromatography was performed by flash chromatography on silica gel 60 (Art. 1.09385) (Mark).

Thirty % of ammonium purchased from Kanto Chemical Co. Ltd. was used as NH$_4$OH Preparation of 20-triazole-20-deoxodesmycosins (1) Preparation of Desmycosin (YT6)

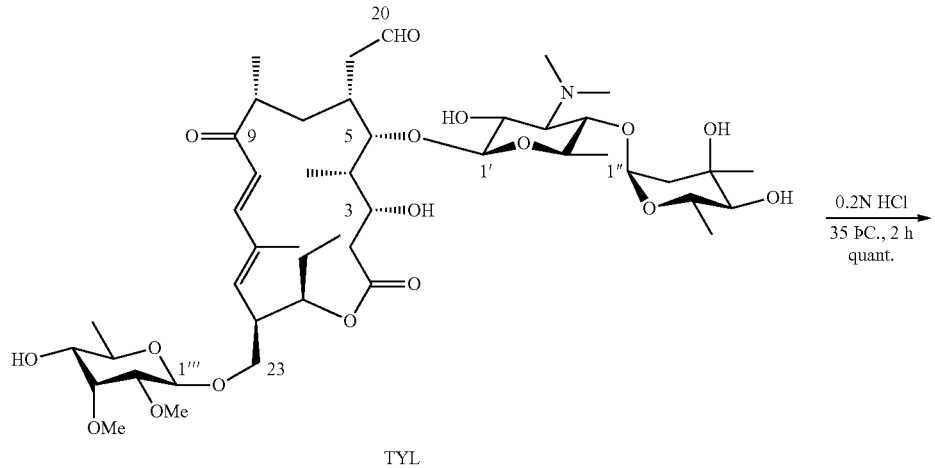

TYL

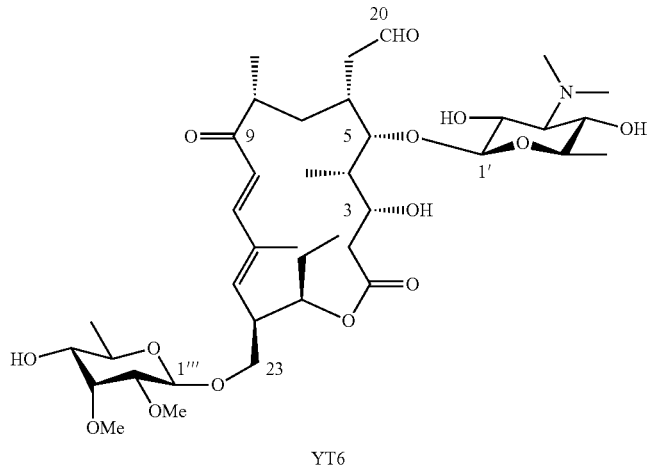

YT6

Tylosin (20.0 g, 21.8 mmol) was dissolved in 0.2N HCl aq. (340 mL) and then the mixture was stirred at 35° C. for 2 hours. After confirming complete consumption of the starting material, the reaction mixture was neutralized by adding 1N NaOH aq., extracted with CHCl$_3$ and dried over Na$_2$SO$_4$. The solvent was removed under reduced-pressure to obtain quantitative amount of desmycosin (YT6).

Rf: 0.53 (CHCl$_3$:MeOH:NH$_4$OH=5:1:0.005).

HRFABMS: calcd. for C$_{39}$H$_{66}$O$_{14}$N: 772.4483 [M+H]. found m/z: 772.4424 [M+H]$^+$.

IR (KBr)vcm$^{-1}$: 3450 (—OH), 2933 (C—H), 1720 (C═O).

$^1$H NMR (270 MHz, CDCl$_3$) δ (ppm): 9.67 (s, 1H, H-20), 7.27 (d, J=15.5 Hz, 1H, H-11), 6.23 (d, J=15.5 Hz, 1H, H-10), 5.87 (d, J=10.2 Hz, 1H, H-13), 4.94 (br. dt, J=9.4 Hz, 1H, H-15), 4.52 (d, J=7.6 Hz, 1H, H-1'''), 4.22 (d, J=7.3 Hz, 1H, H-1'), 3.96 (dd, J=9.4, 3.5 Hz, 1H, H-23), 3.80 (d, J=10.3 Hz, 1H, H-3), 3.71-3.67 (m, 2H, H-5, H-3'''), 3.58 (s, 3H, 3'''-OCH$_3$), 3.53-3.48 (m, 3H, H-23, H-2', H-5'''), 3.45 (s, 3H, 2'''-OCH$_3$), 3.24 (m, 1H, H-5'), 3.14 (dd, J=9.9, 3.0 Hz, 1H, H-4'''), 3.07-2.85 (m, 4H, H-14, H-19, H-4', H-2'''), 2.50 (m, 1H, H-8), 2.49 (s, 6H, 3'-N(CH$_3$)$_2$), 2.41-2.33 (m, 4H, H-2, H-19, H-3'), 2.13 (m, 1H, H-6), 1.94-1.80 (m, 2H, H-2, H-16), 1.76 (s, 3H, H-22), 1.60-1.40 (m, 4H, H-4, H-7, H-16), 1.23-1.21 (m, 6H, H-6', H-6'''), 1.17 (d, J=6.6 Hz, 3H, H-21), 0.97 (d, J=6.6 Hz, 3H, H-18), 0.90 (t, J=6.7 Hz, 3H, H-17).

$^{13}$C NMR (67.5 MHz, CDCl$_3$) δ (ppm): 203.1 (C-9), 202.9 (C-20), 173.8 (C-1), 148.0 (C-11), 142.2 (C-13), 134.8 (C-12), 118.5 (C-10), 104.0 (C-1'), 101.0 (C-1'''), 81.9 (C-2'''), 81.2 (C-5), 79.8 (C-3'''), 75.1 (C-15), 73.3 (C-5'), 72.6 (C-4'''), 71.0 (C-5'''), 70.7 (C-4'), 70.6 (C-2'), 70.1 (C-3'), 69.2 (C-23), 67.4 (C-3), 61.7 (C-8'''), 59.7 (C-7'''), 45.0 (C-14), 44.6 (C-8), 43.8 (C-19), 41.7 (2C, C-7', 8'), 40.3 (C-4), 39.4 (C-2), 32.8 (C-7), 31.9 (C-6), 25.4 (C-16), 17.8 (C-6'''), 17.7 (C-6'), 17.4 (C-21), 12.9 (C-22), 9.6 (C-17), 8.9 (C-18).

(2) Preparation of 20-dihydrodesmycosin (YT7)

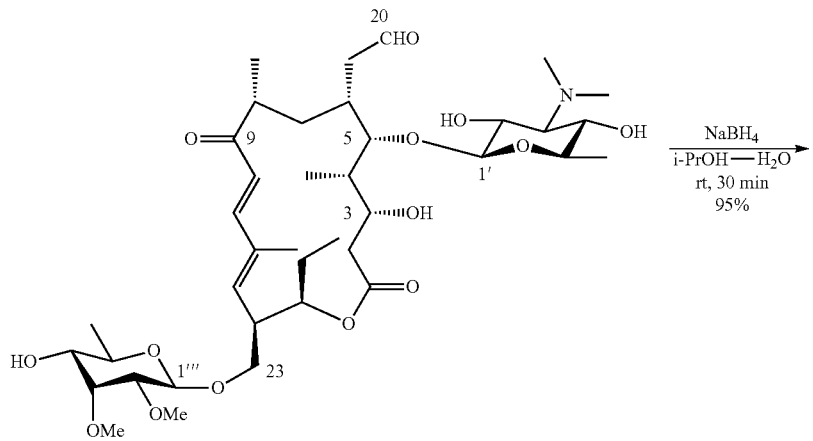

YT6

-continued

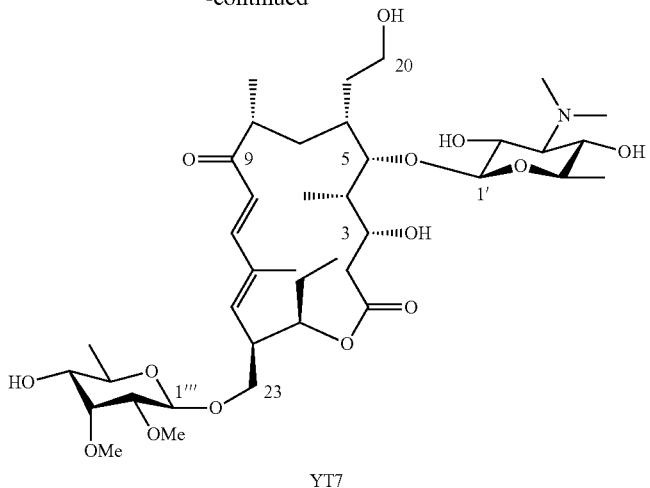

YT7

To a solution of Desmycosin (16.8 g, 21.8 mmol) in i-PrOH:H₂O=3:2 (300 mL) was added NaBH₄ (0.206 g, 5.45 mmol) and then the mixture was stirred at rt for 30 minutes. The reaction mixture was concentrated, neutralized by adding sat. NaHCO₃ aq., extracted with CHCl₃ and dried over Na₂SO₄. The solvent was removed under reduced pressure to obtain YT7 (Yield: 95%).

Rf: 0.50 (CHCl₃:MeOH:NH₄OH=5:1:0.005)

HRFABMS: calcd. for $C_{39}H_{68}O_{14}N$: 774.4640 [M+H]. found m/z: 774.4657 [M+H]⁺.

IR (KBr)νcm⁻¹: 3446 (—OH), 2935 (C—H), 1724 (C=O)

¹H NMR (270 MHz, CDCl₃) δ (ppm): 7.27 (d, J=15.5 Hz, 1H, H-11), 6.23 (br. d, 1H, H-10), 5.85 (br. d, 1H, H-13), 4.97 (br. dt, J=9.7 Hz, 1H, H-15), 4.54 (d, J=7.6 Hz, 1H, H-1'''), 4.31 (d, J=7.0 Hz, 1H, H-1'), 3.97 (dd, J=9.6, 3.6 Hz, 1H, H-23), 3.78-3.73 (m, 5H, H-3, H-5, H-20, H-3'''), 3.60 (s, 3H, 3'''-OC$\underline{H}_3$), 3.55-3.49 (m, 3H, H-23, H-2', H-5'''), 3.47 (s, 3H, 2'''-OC$\underline{H}_3$), 3.33 (m, 1H, H-5'), 3.17 (dd, J=9.5, 3.1 Hz, 1H, H-4'''), 3.08-2.99 (m, 2H, H-4', H-2'''), 2.95 (m, 1H, H-14), 2.74 (m, 1H, H-8), 2.49 (s, 6H, 3'-N(C$\underline{H}_3$)₂), 2.47-2.33 (m, 2H, H-2, H-3'), 1.95 (d, 1H, H-2), 1.89-1.80 (m, 2H, H-6, H-16), 1.77 (s, 3H, H-22), 1.65-1.54 (m, 5H, H-4, H-7, H-19, H-16), 1.25-1.23 (m, 6H, H-6', H-6'''), 1.17 (d, J=6.6 Hz, 3H, H-21), 1.00 (d, J=6.2 Hz, 3H, H-18), 0.91 (t, J=7.3 Hz, 3H, H-17).

¹³C NMR (67.5 MHz, CDCl₃) δ (ppm): 204.2 (C-9), 174.2 (C-1), 148.0 (C-11), 142.6 (C-13), 135.4 (C-12), 118.5 (C-10), 104.4 (C-1'), 101.0 (C-1'''), 82.1 (C-2'''), 80.5 (C-5), 80.1 (C-3'''), 75.5 (C-15), 73.3 (C-5'), 72.6 (C-4'''), 70.3 (4C, C-2', C-3', C-4', C-5'''), 69.3 (C-23), 67.4 (C-3), 62.1 (C-20), 60.6 (C-8'''), 59.8 (C-7'''), 45.0 (2C, C-8, C-14), 42.0 (2C, C-7', 8'), 41.0 (C-4), 39.4 (C-2), 32.8 (C-7), 32.4 (C-6), 31.5 (C-19), 25.4 (C-16), 17.5 (3C, C-21, C-6', C-6'''), 13.1 (C-22), 10.0 (2C, C-17, C-18).

(3) Preparation of 20-chloro-20-deoxodesmycosin (YT8)

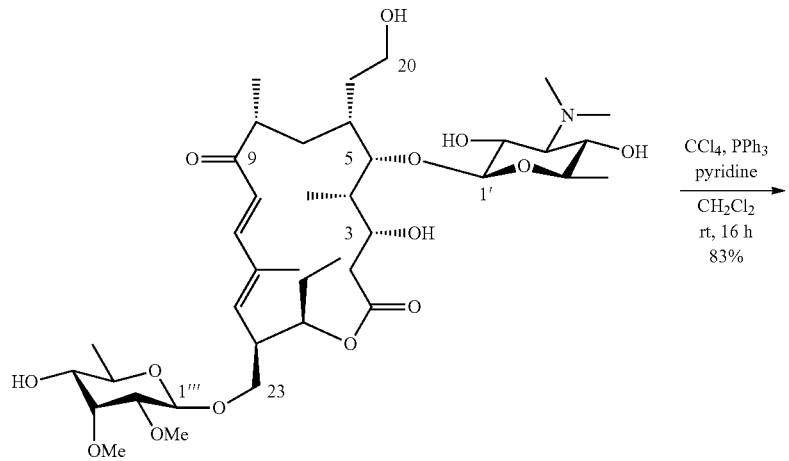

YT7

-continued

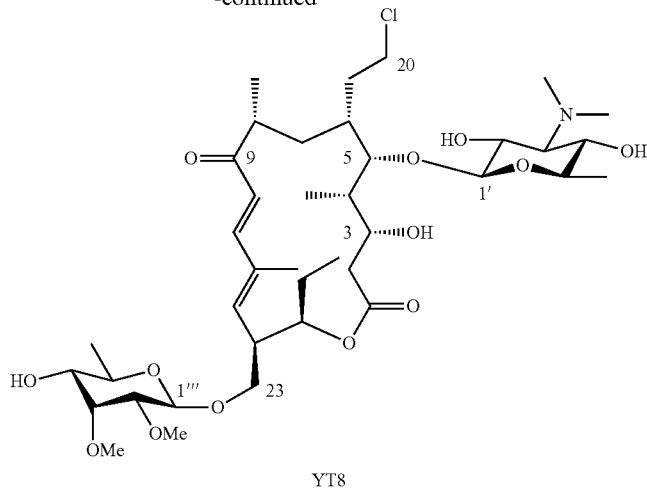

YT8

To a solution of YT7 (16.9 g, 21.8 mmol) in CH$_2$Cl$_2$:pyridine=1:1 (330 mL) were added PPh$_3$ (17.2 g, 65.4 mmol) and CCl$_4$ (3.2 g, 32.7 mmol) under N$_2$ atmosphere and the mixture was stirred for 16 hours at rt. The reaction mixture was diluted with CHCl$_3$, washed sequentially with sat. NaHCO$_3$ aq., brine. The organic layer was dried over Na$_2$SO$_4$ and then the solvent was removed under reduced pressure. The resulting products were purified by flash column chromatography to obtain YT8 (Yield: 83%).

Rf: 0.51 (CHCl$_3$:MeOH:NH$_4$OH=5:1:0.005)

HRFABMS: calcd. for C$_{39}$H$_{67}$O$_{13}$NCl: 792.4301 [M+H]. found m/z: 792.4300 [M+H]$^+$.

IR (KBr)vcm$^{-1}$: 3460 (—OH), 2933 (C—H), 1718 (C=O)

$^1$H NMR (270 MHz, CDCl$_3$) δ (ppm): 7.30 (d, J=15.2 Hz, 1H, H-11), 6.24 (d, J=15.2 Hz, 1H, H-10), 5.87 (d, J=10.9 Hz, 1H, H-13), 4.95 (br. dt, J=8.7 Hz, 1H, H-15), 4.54 (d, J=7.9 Hz, 1H, H-1'''), 4.29 (d, J=7.3 Hz, 1H, H-1'), 3.98 (dd, J=9.4, 3.5 Hz, 1H, H-23), 3.74-3.67 (m, 3H, H-3, H-5, H-3'''), 3.60 (s, 3H, 3'''-OCH$_3$), 3.60-3.47 (m, 5H, H-20, H-23, H-2', H-5'''), 3.47 (s, 3H, 2'''-OCH$_3$), 3.29 (m, 1H, H-5'), 3.17 (d, J=8.6 Hz, 1H, H-4'''), 3.07 (d, J=9.5, H-4'), 3.01 (dd, J=6.9, 2.6, 1H, H-2'''), 2.94 (m, 1H, H-14), 2.73 (m, 1H, H-8), 2.49 (s, 6H, 3'-N(CH$_3$)$_2$), 2.40 (d, J=4.9 Hz, 1H, H-2), 2.34 (d, J=9.9 Hz, 1H, H-3'), 2.14 (m, 1H, H-6), 1.96-1.83 (m, 2H, H-2, H-16), 1.77 (s, 3H, H-22), 1.62-1.51 (m, 5H, H-4, H-7, H-16, H-19), 1.30 (d, J=5.9 Hz, 3H, H-6'), 1.25 (d, J=6.9 Hz, 3H, H-6'''), (d, J=6.6 Hz, 3H, H-21), 1.01 (d, J=6.6 Hz, 3H, H-18), 0.91 (t, J=7.1 Hz, 3H, H-17).

$^{13}$C NMR (67.5 MHz, CDCl$_3$) δ (ppm): 203.5 (C-9), 174.2 (C-1), 147.7 (C-11), 141.9 (C-13), 134.9 (C-12), 118.5 (C-10), 103.9 (C-1'), 101.0 (C-1'''), 81.8 (C-2'''), 79.7 (C-5), 77.2 (C-3'''), 75.2 (C-15), 73.3 (C-5'), 72.6 (C-4'''), 70.7 (4C, C-2', C-3', C-4', C-5'''), 70.1 (C-23), 68.8 (C-3), 61.7 (C-8''), 59.6 (C-7''), 44.9 (2C, C-8, C-14), 43.1 (C-20), 41.7 (2C, C-7', 8'), 41.0 (C-4), 39.4 (C-2), 32.8 (C-7), 31.8 (C-6), 27.6 (C-19), 25.4 (C-16), 17.8 (3C, C-21, C-6', C-6'''), 12.9 (C-22), 9.6 (C-17), 9.4 (C-18).

(4) Preparation of 20-azido-20-deoxodesmycosin (YT11)

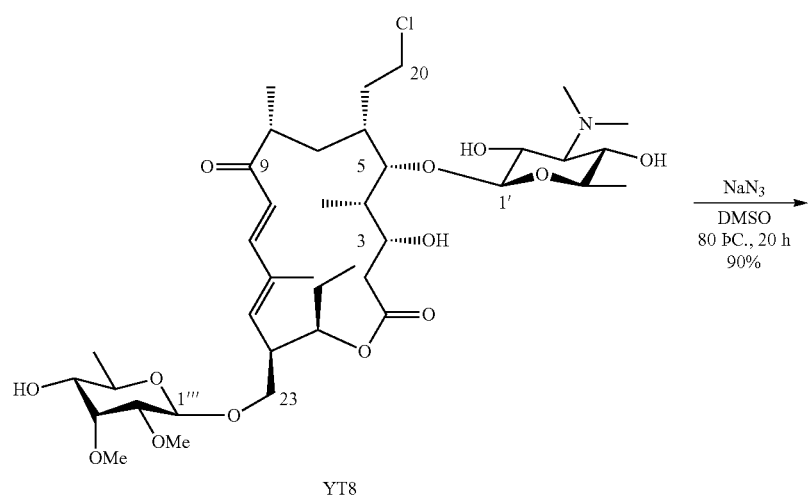

YT8

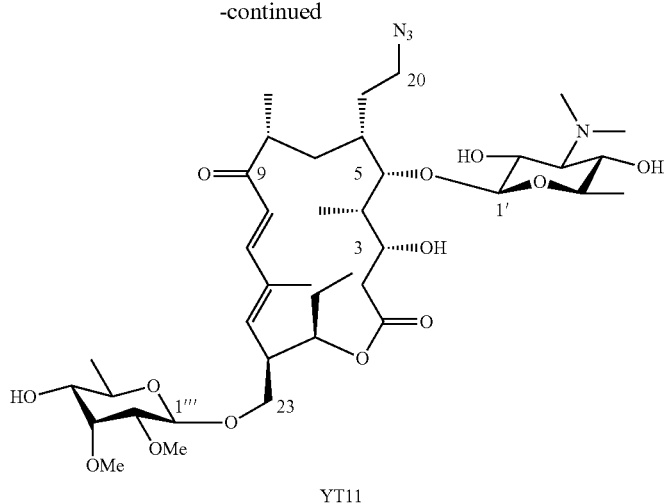

YT11

To a solution of YT8 (12.4 g, 15.7 mmol) in DMSO (160 mL, 0.100 M) was added NaN₃ (5.10 g, 78.3 mmol) and then the mixture was stirred for 20 hours at 80° C. The reaction mixture was diluted with AcOEt and water. The organic layer was separated, the aqueous layer was extracted with AcOEt and the combined organic layer was washed with water, brine, and then dried over Na₂SO₄ and concentrated. The resulting products were purified by flash column chromatography to obtain YT11 (Yield: 90%).

Rf: 0.51 (CHCl₃:MeOH:NH₄OH=5:1:0.005)

HRFABMS: calcd. for $C_{39}H_{67}O_{13}N_4$: 799.4705 [M+H]. found m/z: 799.4684 [M+H]⁺.

IR (KBr)vcm⁻¹: 3458 (—OH), 2933 (C—H), 2096 (—N₃), 1716 (C═O)

¹H NMR (270 MHz, CDCl₃) δ (ppm): 7.30 (d, J=15.5 Hz, 1H, H-11), 6.24 (d, J=15.5 Hz, 1H, H-10), 5.87 (d, J=9.9 Hz, 1H, H-13), 4.95 (br. dt, J=8.4 Hz, 1H, H-15), 4.54 (d, J=7.9 Hz, 1H, H-1'''), 4.29 (d, J=7.3 Hz, 1H, H-1'), 3.98 (dd, J=9.6, 3.6 Hz, 1H, H-23), 3.74-3.66 (m, 3H, H-3, H-5, H-3'''), 3.60 (s, 3H, 3'''-OCH₃), 3.56-3.49 (m, 3H, H-23, H-2', H-5'''), 3.47 (s, 3H, 2'''-OCH₃), 3.32-3.20 (m, 3H, H-20, H-5'), 3.16 (dd, J=9.2, 3.0 Hz, 1H, H-4''), 3.07 (d, J=9.6 Hz, 1H, H-4'), 3.01 (dd, J=7.7, 2.8 Hz, 1H, H-2''), 2.94 (m, 1H, H-14), 2.73 (m, 1H, H-8), 2.48 (s, 6H, 3'-N(CH₃)₂), 2.42 (d, J=12.2 Hz, 1H, H-2), 2.34 (d, J=9.9 Hz, H-3'), 1.96-1.83 (m, 3H, H-2, H-6, H-16), 1.77 (s, 3H, H-22), 1.63-1.49 (m, 5H, H-4, H-7, H-9, H-16), 1.29 (d, J=6.3 Hz, 3H, H-6'), 1.24 (d, J=5.9 Hz, 3H, H-6'''), 1.18 (d, J=6.6 Hz, 3H, H-21), 1.01 (d, J=6.6 Hz, 3H, H-18), 0.92 (t, J=7.2 Hz, 3H, H-17).

¹³C NMR (67.5 MHz, CDCl₃) δ (ppm): 203.3 (C-9), 174.1 (C-1), 147.8 (C-11), 141.9 (C-13), 134.7 (C-12), 118.5 (C-10), 103.8 (C-1'), 100.8 (C-1'''), 81.6 (C-2'''), 79.7 (C-5), 77.3 (C-3'''), 75.1 (C-15), 73.1 (C-5'), 72.5 (C-4'''), 70.7 (4C, C-2', C-3', C-4', C-5'''), 70.0 (C-23), 68.8 (C-3), 61.5 (C-8''), 59.4 (C-7''), 49.3 (C-20), 44.7 (2C, C-8, C-14), 41.5 (2C, C-7', 8'), 41.5 (C-4), 39.2 (C-2), 32.8 (C-7), 32.4 (C-6), 27.6 (C-19), 25.1 (C-16), 17.6 (3C, C-21, C-6', C-6'''), 12.8 (C-22), 9.4 (C-17), 9.2 (C-18).

(5) Preparation of 20-triazole-20-deoxodesmycosins

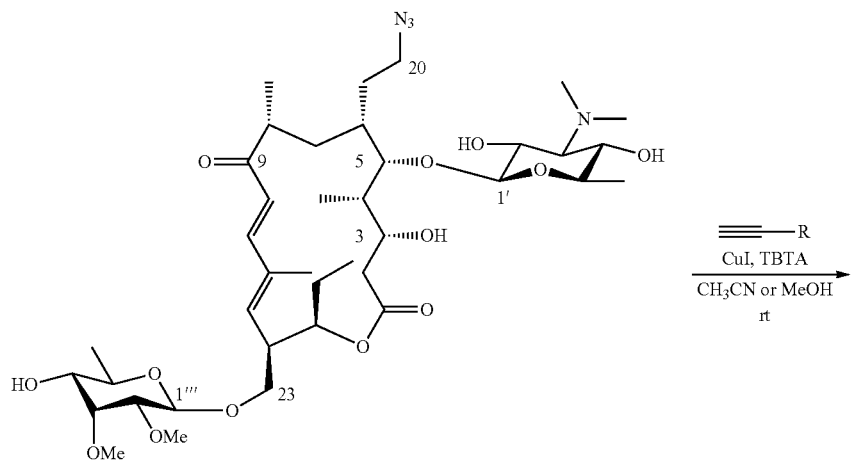

YT11

-continued

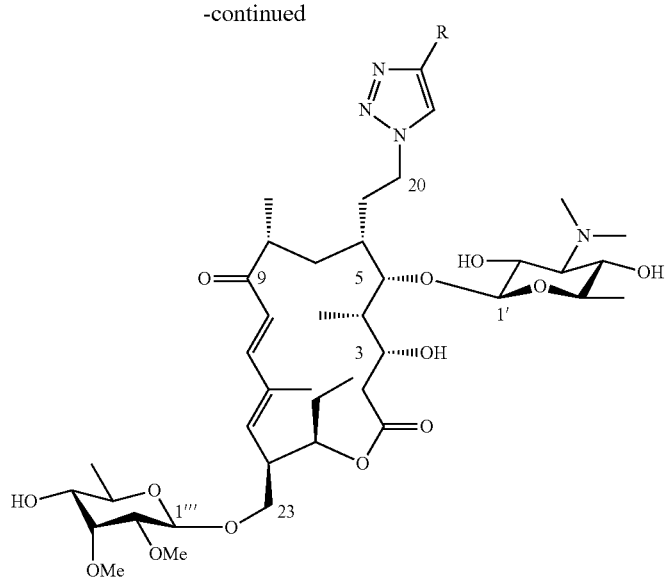

To a solution of YT11 (0.24 g, 0.30 mmol) in CH₃CN or MeOH (3.0 mL) were added copper catalyst (2.9 mg, 0.015 mmol), TBTA (1.6 mg, 3.0 μmol) or 2,6-lutidine (0.01 eq.) and acetylene compound wherein R is p-ethynyl (pentyloxy)benzene or phenyl (0.33 mmol) and the mixture was stirred at rt until the reaction was completed. After completion, the reaction mixture was diluted with CHCl₃, washed with 10% NH₃ aq. After removing copper catalyst, the filtrate was washed with brine. The organic layer was dried over Na₂SO₄ and concentrated. The resulting products were purified by flash column chromatography to obtain the triazole compounds.

The results of the step (5) are shown in Table 1 below.

TABLE 1

| | | | Reaction times* | |
|---|---|---|---|---|
| Entry | Conditions | Solvents (0.1M) | R = p-ethynyl (pentyloxy)benzene | R = Ph |
| 1 | CuI (0.05 eq.) 2,6-lutidine (0.01 eq.), rt Cu(CH₃CN)₄PF₆ (0.05 eq.) | CH₃CN | 2 days | 2 days |
| 2 | TBTA (0.01 eq.), rt Cu(CH₃CN)₄PF₆ (0.05 eq.) | MeOH | 2 days | 2 days |
| 3 | TBTA (0.01 eq.), rt CuI (0.05 eq.) | CH₃CN | 30 min | 30 min |
| 4 | TBTA (0.01 eq.), rt CuI (0.05 eq.) | MeOH | 50 min | 120 min |
| 5 | TBTA (0.01 eq.), rt | CH₃CN | 90 min | 120 min |

*Time for consumption of the starting material.

Under the conditions of Entry 4 or 5 above, with the following nineteen compounds:

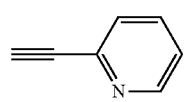
yt12

-continued

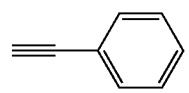
yt13

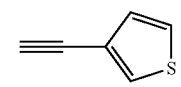
yt14

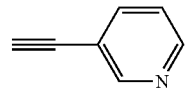
yt16

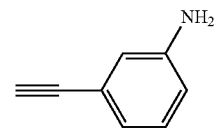
yt17

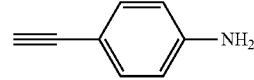
yt18

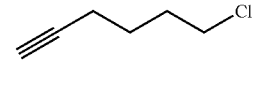
yt19

yt20

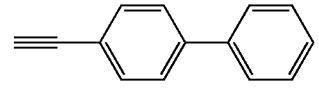
yt21

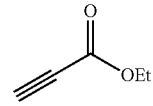
yt22

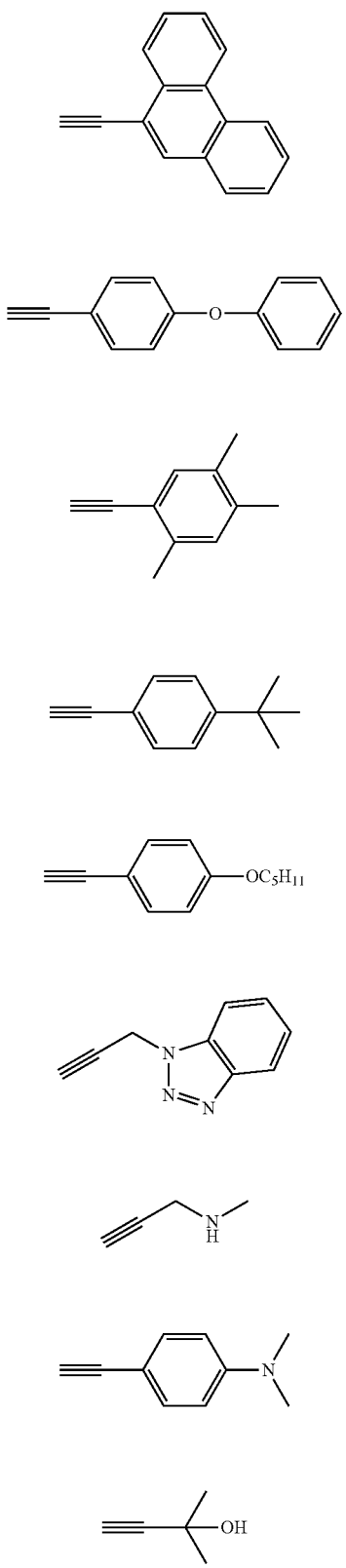

20-(4-(pyridine-2-yl)-1H-1,2,3-triazol-1-yl)-20-deoxodesmycosin (YT12)

Yield: 85%

HRFABMS: calcd. for $C_{46}H_{72}O_{13}N_5$: 902.5127 [M+H]. found m/z: 902.5132 [M+H]$^+$.

IR (KBr)νcm$^{-1}$: 3436 (—OH), 2933 (C—H), 1722 (C=O).

$^1$H NMR (270 MHz, CDCl$_3$) δ (ppm): 8.62 (d, J=2.8 Hz, 1H, H-20-triazole-pyridine), 8.23 (m, 2H, H-20-triazole-2-pyridine, H-20-triazole-2-pyridine), 7.79 (dt, J=5.5, 2.0 Hz, 1H, H-20-triazole-2-pyridine), 7.23 (dd, J=5.9, 5.0 Hz, 1H, H-20-triazole-2-pyridine), 7.12 (d, J=15.5 Hz, 1H, H-11), 6.19 (d, J=15.5 Hz, 1H, H-10), 5.62 (d, J=10.2 Hz, 1H, H-13), 4.89 (br. dt, J=9.2 Hz, 1H, H-15), 4.57 (d, J=7.9 Hz, 1H, H-1'''), 4.48 (m, 2H, H-20), 4.37 (d, J=7.6 Hz, 1H, H-1'), 3.97 (dd, J=9.2, 4.0 Hz, 1H, H-23), 3.82 (d, J=9.2 Hz, 1H, H-5), 3.76 (t, J=3.1 Hz, 1H, H-3'''), 3.64 (s, 3H, 3'''-OCH$_3$), 3.61-3.48 (m, 4H, H-3, H-23, H-2', H-5'''), 3.46 (s, 3H, 2'''-OCH$_3$), 3.35 (m, 1H, H-5'), 3.18 (dd, J=9.4, 3.1 Hz, 1H, H-4'''), 3.09 (d, J=9.6, 1H, H-4'), 3.01 (dd, J=7.9, 3.0, 1H, H-2'''), 2.94 (m, 1H, H-14), 2.67 (m, 1H, H-8), 2.51 (s, 6H, 3'-N(CH$_3$)$_2$), 2.46-2.36 (m, 3H, H-2, H-6, H-3'), 2.04 (m, 1H, H-19), 1.90-1.85 (m, 2H, H-2, H-16), 1.61 (s, 3H, H-22), 1.62-1.51 (m, 4H, H-4, H-7, H-16), 1.27 (d, J=6.3 Hz, 3H, H-6'), 1.24 (d, J=6.3 Hz, 3H, H-6'''), 1.18 (d, J=6.6 Hz, 3H, H-21), 1.04 (d, J=6.6 Hz, 3H, H-18), 0.92 (t, J=7.3 Hz, 3H, H-17).

$^{13}$C NMR (67.5 MHz, CDCl$_3$) δ (ppm): 203.4 (C-9), 174.2 (C-1), 150.8 (C-20-triazole-2-pyridine), 149.7 (C-20-triazole-2-pyridine), 148.2 (C-11), 142.5 (C-13), 137.1 (C-20-triazole-2-pyridine), 135.2 (C-12), 122.9 (C-20-triazole-2-pyridine), 122.5 (2C, C-20-triazole-2-pyridine), 120.7 (C-20-triazole-2-pyridine), 118.6 (C-10), 104.2 (C-1'), 101.4 (C-1'''), 82.0 (C-2'''), 80.3 (C-5), 78.1 (C-3'''), 75.4 (C-15), 73.6 (C-5'), 73.1 (C-4'''), 70.7 (4C, C-2', C-3', C-4', C-5'''), 69.5 (C-23), 67.1 (C-3), 62.0 (C-8''), 59.8 (C-7''), 48.8 (C-20), 45.2 (2C, C-8, C-14), 39.7 (2C, C-7', 8'), 41.5 (C-4'), 39.7 (C-2), 32.8 (C-7), 32.4 (C-6), 27.6 (C-19), 25.6 (C-16), 18.1 (2C, C-6', C-6'''), 17.6 (C-21), 13.2 (C-22), 9.9 (C-17), 9.5 (C-18).

as the acetylene compound, the step (5) above was repeated to obtain the 20-triazole-20-deoxodesmycosins, which are shown below.

20-(4-phenyl-1H-1,2,3-triazol-1-yl)-20-deoxodesmycosin (YT13)

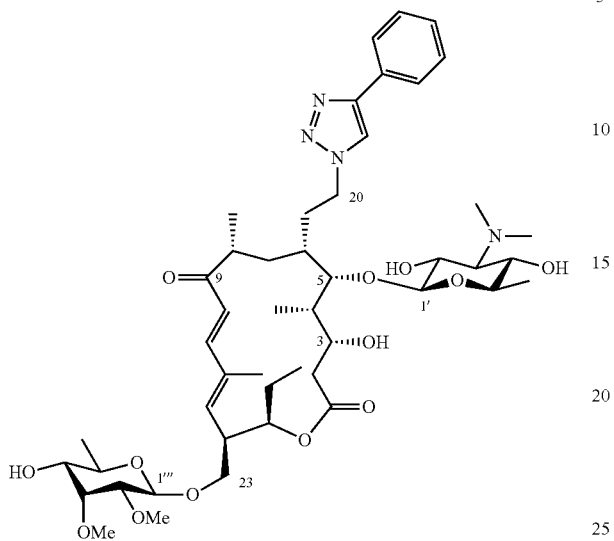

Yield: 98%

HRFABMS: calcd. for $C_{47}H_{73}O_{13}N_4$: 901.5174 [M+H]. found m/z: 902.5157 [M+H]$^+$.

IR (KBr)vcm$^{-1}$: 3442 (—OH), 2933 (C—H), 1720 (C=O).

$^1$H NMR (270 MHz, CDCl$_3$) δ (ppm): 8.00 (d, J=7.3 Hz, 2H, H-20-triazole-phenyl), 7.90 (s, 1H, H-20-triazole-phenyl), 7.46 (t, J=7.6 Hz, 2H, H-20-triazole-phenyl), 7.32 (t, J=6.9 Hz, 1H, H-20-triazole-phenyl), 6.92 (d, J=15.5 Hz, 1H, H-11), 6.14 (d, J=15.2 Hz, 1H, H-10), 5.23 (d, J=9.6 Hz, 1H, H-13), 4.80 (br. dt, J=9.6 Hz, 1H, H-15), 4.57 (d, J=7.6 Hz, 1H, H-1'''), 4.48 (m, 2H, H-20), 4.35 (d, J=7.2 Hz, 1H, H-1'), 3.92 (dd, J=9.2, 4.3 Hz, 1H, H-23), 3.81 (d, J=9.9 Hz, 1H, H-5), 3.76 (t, J=2.6 Hz, 1H, H-3'''), 3.64 (s, 3H, 3'''-OCH$_3$), 3.60-3.36 (m, 5H, H-3, H-23, H-2', H-5''', H-5'), 3.40 (s, 3H, 2'''-OCH$_3$), 3.16 (dd, J=9.4, 3.1 Hz, 1H, H-4'''), 3.08 (d, J=9.6, H-4'), 2.98 (dd, J=7.8, 2.4, 1H, H-2''), 2.86 (m, 1H, H-14), 2.67 (m, 1H, H-8), 2.50 (s, 6H, 3'-N(CH$_3$)$_2$), 2.44-2.37 (m, 2H, H-2, H-3'), 2.20 (m, 1H, H-6), 2.02 (m, 1H, H-19), 1.90-1.75 (m, 2H, H-2, H-16), 1.66 (s, 3H, H-22), 1.62-1.51 (m, 4H, H-4, H-7, H-16), 1.28 (d, J=6.0 Hz, 3H, H-6'), 1.27 (d, J=6.0 Hz, 3H, H-6'''), 1.17 (d, J=6.9 Hz, 3H, H-21), 1.00 (d, J=6.6 Hz, 3H, H-18), 0.90 (t, J=7.3 Hz, 3H, H-17).

$^{13}$C NMR (67.5 MHz, CDCl$_3$) δ (ppm): 203.8 (C-9), 173.7 (C-1), 148.1 (C-11), 147.7 (C-20-triazole-phenyl), 142.7 (C-13), 134.9 (C-12), 131.1 (C-20-triazole-phenyl), 129.2 (C-20-triazole-phenyl), 128.9 (C-20-triazole-phenyl), 128.1 (C-20-triazole-phenyl), 126.1 (2C, C-20-triazole-phenyl), 119.7 (C-20-triazole-phenyl), 118.2 (C-10), 103.8 (C-1'), 101.3 (C-1'''), 81.9 (C-2'''), 80.1 (C-5), 78.0 (C-3'''), 75.1 (C-15), 73.4 (C-5'), 73.0 (C-4''), 70.5 (4C, C-2', C-3', C-4', C-5'''), 69.6 (C-23), 66.9 (C-3), 61.8 (C-8'''), 59.7 (C-7'''), 48.1 (C-20), 45.0 (2C, C-8, C-14), 41.9 (2C, C-7', 8'), 41.5 (C-4), 39.5 (C-2), 32.8 (C-7), 32.4 (C-6), 27.7 (C-19), 25.6 (C-16), 18.0 (2C, C-6', C-6'''), 17.5 (C-21), 13.1 (C-22), 9.8 (C-17), 9.3 (C-18).

20-(4-(thiophene-3-yl)-1H-1,2,3-triazol-1-yl)-20-deoxodesmycosin (YT14)

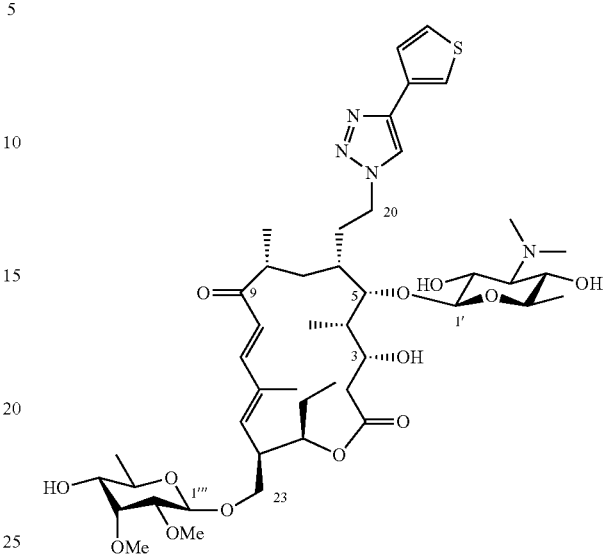

Yield: 81%

HRFABMS: calcd. for $C_{45}H_{71}O_{13}N_4S$: 907.4738 [M+H]. found m/z: 907.4730 [M+H]$^+$.

IR (KBr)vcm$^{-1}$: 3437 (—OH), 2933 (C—H), 1720 (C=O).

$^1$H NMR (270 MHz, CDCl$_3$) δ (ppm): 7.84 (s, 1H, H-20-triazole-thiophene), 7.81 (s, 1H, H-20-triazole-thiophene), 7.65 (d, J=4.6 Hz, 1H, H-20-triazole-thiophene), 7.42 (m, 1H, H-20-triazole-thiophene), 6.91 (d, J=15.5 Hz, 1H, H-11), 6.15 (d, J=15.5 Hz, 1H, H-10), 5.31 (d, J=11.2 Hz, 1H, H-13), 4.84 (dt, J=9.2, 7.0 Hz, 1H, H-15), 4.57 (d, J=7.9 Hz, 1H, H-1'''), 4.48 (m, 2H, H-20), 4.35 (d, J=7.6 Hz, 1H, H-1'), 3.95 (dd, J=9.2, 4.2 Hz, 1H, H-23), 3.81 (d, J=9.9 Hz, 1H, H-5), 3.75 (t, J=3.0 Hz, 1H, H-3'''), 3.64 (s, 3H, 3'''-OCH$_3$), 3.60-3.35 (m, 5H, H-3, H-23, H-2', H-5''', H-5'), 3.43 (s, 3H, 2'''-OCH$_3$), 3.17 (dd, J=9.2, 3.1 Hz, 1H, H-4'''), 3.10 (br. dd, J=9.4, H-4'), 3.01 (dd, J=7.9, 2.8, 1H, H-2'''), 2.89 (m, 1H, H-14), 2.65 (m, 1H, H-8), 2.53 (s, 6H, 3'-N(CH$_3$)$_2$), 2.49-2.39 (m, H-2, H-3'), 2.25 (m, 1H, H-6), 2.08 (m, 1H, H-19), 1.85-1.75 (m, 2H, H-2, H-16), 1.68 (s, 3H, H-22), 1.56-1.54 (m, 4H, H-4, H-7, H-16), 1.29 (d, J=6.0 Hz, 3H, H-6'), 1.27 (d, J=6.2 Hz, 3H, H-6'''), 1.18 (d, J=6.9 Hz, 3H, H-21), 1.01 (d, J=6.6 Hz, 3H, H-18), 0.90 (t, J=7.3 Hz, 3H, H-17).

$^{13}$C NMR (67.5 MHz, CDCl$_3$) δ (ppm): 204.0 (C-9), 174.0 (C-1), 148.3 (C-11), 144.4 (C-20-triazole-thiophene), 143.1 (C-13), 135.1 (C-12), 132.5 (C-20-triazole-thiophene), 126.6 (C-20-triazole-thiophene), 121.4 (C-20-triazole-thiophene), 119.7 (C-20-triazole-thiophene), 118.5 (C-10), 104.0 (C-1'), 101.5 (C-1'''), 82.2 (C-2'''), 80.2 (C-5), 78.0 (C-3'''), 75.1 (C-15), 73.6 (C-5'), 73.1 (C-4''), 70.8 (4C, C-2', C-3', C-4', C-5'''), 69.8 (C-23), 66.9 (C-3), 62.1 (C-8'''), 59.9 (C-7'''), 48.3 (C-20), 45.3 (2C, C-8, C-14), 42.1 (2C, C-7', 8'), 41.5 (C-4), 39.8 (C-2), 32.8 (C-7), 32.4 (C-6), 26.7 (C-19), 25.6 (C-16), 18.2 (2C, C-6', C-6'''), 17.5 (C-21), 13.3 (C-22), 10.0 (C-17), 9.5 (C-18).

20-(4-(pyridine-3-yl)-1H-1,2,3-triazol-1-yl)-20-deoxodesmycosin (YT16)

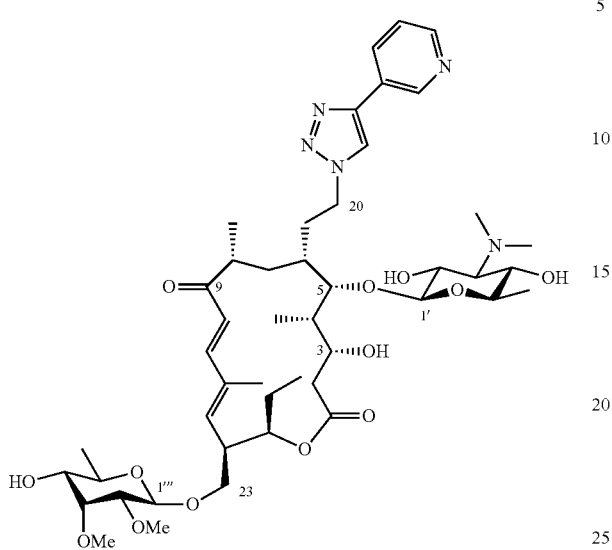

Yield: 82%

HRFABMS: calcd. for $C_{46}H_{72}O_{13}N_5$: 902.5127 [M+H]. found m/z: 902.5106 [M+H]$^+$.

IR (KBr)vcm$^{-1}$: 3438 (—OH), 2931 (C—H), 1722 (C=O).

$^1$H NMR (270 MHz, CDCl$_3$) δ (ppm): 9.22 (s, 1H, H-20-triazole-3-pyridine), 8.59 (d, J=4.0 Hz, 1H, H-20-triazole-3-pyridine), 8.34 (d, 1H, H-20-triazole-3-pyridine), 8.02 (s, 1H, H-20-triazole-3-pyridine), 7.43 (dd, J=7.9, 5.1 Hz, 1H, H-20-triazole-3-pyridine), 6.88 (d, J=15.2 Hz, 1H, H-11), 6.16 (d, J=15.2 Hz, 1H, H-10), 5.30 (d, J=10.2 Hz, 1H, H-13), 4.87 (br. dt, J=9.2 Hz, 1H, H-15), 4.58 (d, J=7.6 Hz, 1H, H-1'''), 4.48 (m, 2H, H-20), 4.37 (d, J=7.6 Hz, 1H, H-1'), 3.97 (dd, J=9.6, 4.0 Hz, 1H, H-23), 3.83 (d, J=9.9 Hz, 1H, H-5), 3.76 (t, J=2.7 Hz, 1H, H-3'''), 3.65 (s, 3H, 3'''-OCH$_3$), 3.61-3.35 (m, 4H, H-3, H-23, H-2', H-5'''), 3.41 (s, 3H, 2'''-OCH$_3$), 3.35 (m, 1H, H-5'), 3.18 (dd, J=9.3, 3.2 Hz, 1H, H-4'''), 3.11 (t, J=9.4, H-4'), 3.01 (dd, J=7.9, 2.7, 1H, H-2''), 2.91 (m, 1H, H-14), 2.65 (m, 1H, H-8), 2.53 (s, 6H, 3'-N(CH$_3$)$_2$), 2.46-2.39 (m, 2H, H-2, H-3'), 2.28 (m, 1H, H-6), 2.05, (m, 1H, H-19), 1.85-1.79 (m, 2H, H-2, H-16), 1.69 (s, 3H, H-22), 1.60-1.55 (m, 4H, H-4, H-7, H-16), 1.27 (d, J=6.3 Hz, 3H, H-6'), 1.24 (d, J=6.3 Hz, 3H, H-6'''), 1.18 (d, J=6.9 Hz, 3H, H-21), 1.03 (d, J=6.6 Hz, 3H, H-18), 0.91 (t, J=7.3 Hz, 3H, H-17).

$^{13}$C NMR (67.5 MHz, CDCl$_3$) δ (ppm): 203.7 (C-9), 174.1 (C-1), 149.0 (C-20-triazole-3-pyridine), 148.1 (C-20-triazole-3-pyridine), 147.4 (C-11), 144.8 (C-20-triazole-3-pyridine), 143.0 (C-13), 135.0 (C-12), 133.6 (C-20-triazole-3-pyridine), 127.5 (C-20-triazole-3-pyridine), 124.0 (C-20-triazole-3-pyridine), 120.4 (C-20-triazole-3-pyridine), 118.3 (C-10), 104.0 (C-1'), 101.5 (C-1'''), 82.0 (C-2'''), 80.3 (C-5), 77.7 (C-3'''), 75.3 (C-15), 73.6 (C-5'), 73.1 (C-4'''), 70.5 (4C, C-2', C-3', C-4', C-5'''), 69.7 (C-23), 67.0 (C-3), 62.0 (C-8''), 59.8 (C-7''), 48.4 (C-20), 45.2 (2C, C-8, C-14), 42.0 (2C, C-7', 8'), 40.7 (C-4), 39.7 (C-2), 32.8 (C-7), 31.8 (C-6), 25.8 (C-19), 25.8 (C-16), 18.1 (2C, C-6', C-6'''), 17.6 (C-21), 13.2 (C-22), 9.9 (C-17), 9.5 (C-18).

20-(4-(3-aminophenyl-1H-1,2,3-triazol-1-yl)-20-deoxodesmycosin (YT17)

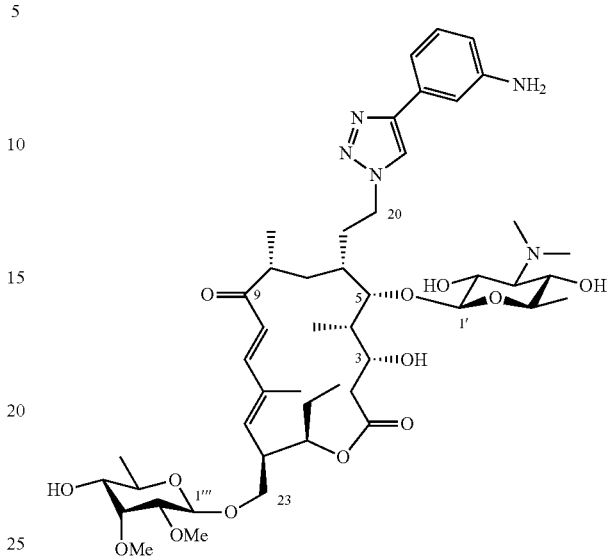

Yield: 91%

HRFABMS: calcd. for $C_{47}H_{74}O_{13}N_5$: 916.5283 [M+H]. found m/z: 916.5309 [M+H]$^+$.

IR (KBr)vcm$^{-1}$: 3463 (—OH), 2933 (C—H), 1720 (C=O).

$^1$H NMR (270 MHz, CDCl$_3$) δ (ppm): 7.84 (s, 1H, H-20-triazole-3-aniline), 7.33-7.29 (m, 2H, H-20-triazole-3-aniline), 7.18 (t, J=7.6 Hz, 1H, H-20-triazole-3-aniline), 6.84 (d, J=15.2 Hz, 1H, H-11), 6.61 (d, J=7.0 Hz, 1H, H-20-triazole-3-aniline), 6.08 (d, J=15.5 Hz, 1H, H-10), 5.17 (d, J=9.6 Hz, 1H, H-13), 4.76 (br. dt, J=8.9 Hz, 1H, H-15), 4.52 (d, J=7.9 Hz, 1H, H-1'''), 4.48 (m, 2H, H-20), 4.30 (d, J=7.2 Hz, 1H, H-1'), 3.90 (dd, J=9.6, 4.3 Hz, 1H, H-23), 3.75 (d, J=9.9 Hz, 1H, H-5), 3.71 (t, J=2.8 Hz, 1H, H-3'''), 3.58 (s, 3H, 3'''-OCH$_3$), 3.55-3.23 (m, 5H, H-3, H-23, H-2', H-5', H-5'''), 3.34 (s, 3H, 2'''-OCH$_3$), 3.14 (dd, J=9.6, 3.0 Hz, 1H, H-4'''), 3.06 (d, J=9.6, H-4'), 2.94 (dd, J=7.9, 2.7, 1H, H-2''), 2.86 (m, 1H, H-14), 2.67 (m, 1H, H-8), 2.47 (s, 6H, 3'-N(CH$_3$)$_2$), 2.39-2.34 (m, 2H, H-2, H-3'), 2.18 (m, 1H, H-6), 1.99 (m, 1H, H-19), 1.77-1.71 (m, 2H, H-2, H-16), 1.61 (s, 3H, H-22), 1.57-1.44 (m, 4H, H-4, H-7, H-16), 1.23 (d, J=6.3 Hz, 3H, H-6'), 1.22 (d, J=6.0 Hz, 3H, H-6'''), 1.11 (d, J=6.6 Hz, 3H, H-21), 0.97 (d, J=6.6 Hz, 3H, H-18), 0.85 (t, J=7.1 Hz, 3H, H-17).

$^{13}$C NMR (67.5 MHz, C13) δ (ppm): 203.9 (C-9), 173.9 (C-1), 148.4 (C-11), 148.0 (C-20-triazole-3-aniline), 147.3 (C-20-triazole-3-aniline), 142.9 (C-13), 135.2 (C-12), 132.0 (C-20-triazole-3-aniline), 130.0 (C-20-triazole-3-aniline), 120.0 (C-20-triazole-3-aniline), 118.3 (C-10), 116.3 (C-20-triazole-3-aniline), 115.0 (C-20-triazole-3-aniline), 112.8 (C-20-triazole-3-aniline), 104.0 (C-1'), 101.4 (C-1'''), 81.9 (C-2'''), 80.3 (C-5), 77.7 (C-3'''), 75.3 (C-15), 73.5 (C-5'), 73.0 (C-4'''), 70.5 (4C, C-2', C-3', C-4', C-5'''), 69.9 (C-23), 67.1 (C-3), 62.0 (C-8''), 59.8 (C-7''), 47.9 (C-20), 45.1 (2C, C-8, C-14), 41.9 (2C, C-7', 8'), 40.9 (C-4), 39.7 (C-2), 33.2 (C-7), 32.8 (C-6), 27.9 (C-19), 25.9 (C-16), 18.1 (2C, C-6', C-6'''), 17.7 (C-21), 13.2 (C-22), 9.9 (C-17), 9.4 (C-18).

20-(4-(3-aminophenyl-1H-1,2,3-triazol-1-yl)-20-deoxodesmycosin (YT18)

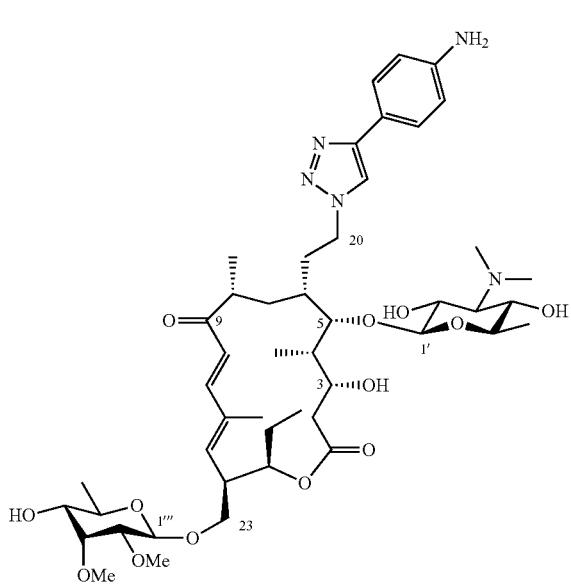

Yield: 67%

HRFABMS: calcd. for $C_{47}H_{74}O_{13}N_5$: 916.5283 [M+H]. found m/z: 916.5266 [M+H]$^+$.

IR (KBr)vcm$^{-1}$: 3448 (—OH), 2933 (C—H), 1720 (C=O).

$^1$H NMR (270 MHz, CDCl$_3$) δ (ppm): 7.83 (d, J=7.9 Hz, 1H, H-20-triazole-4-aniline), 7.77 (s, 1H, H-20-triazole-4-aniline), 7.73 (d, J=8.9 Hz, 1H, H-20-triazole-4-aniline), 6.90 (d, J=15.5 Hz, 1H, H-11), 6.80-6.77 (m, 2H, H-20-triazole-4-aniline), 6.11 (d, J=15.5 Hz, 1H, H-10), 5.12 (br. d, 1H, H-13), 4.75 (br. dt, J=8.9 Hz, 1H, H-15), 4.61 (d, J=7.9 Hz, 1H, H-1'''), 4.53 (m, 2H, H-20), 4.35 (d, J=7.3 Hz, 1H, H-1'), 3.96 (dd, J=9.0, 3.5 Hz, 1H, H-23), 3.79-3.72 (m, 2H, H-5, H-3'''), 3.64 (s, 3H, 3'''-OCH$_3$), 3.50-3.45 (m, 5H, H-3, H-23, H-2', H-5'''), 3.42 (s, 3H, 2'''-OCH$_3$), 3.32 (m, 1H, H-5'), 3.20-3.12 (m, 2H, H-4', H-4'''), 3.00 (dd, J=7.9, 2.6, 1H, H-2'''), 2.86 (m, 1H, H-14), 2.60 (m, 1H, H-8), 2.59 (s, 6H, 3'-N(CH$_3$)$_2$), 2.45-2.35 (m, 2H, H-2, H-3'), 2.18-1.14 (m, 2H, H-6, H-19), 1.74-1.64 (m, 2H, H-2, H-16), 1.61 (s, 3H, H-22), 1.56-1.45 (m, 4H, H-4, H-7, H-16), 1.27 (d, J=6.3 Hz, 3H, H-6'), 1.26 (d, J=6.0 Hz, 3H, H-6'''), 1.16 (d, J=6.9 Hz, 3H, H-21), 0.98 (d, J=6.9 Hz, 3H, H-18), 0.88 (t, J=7.2 Hz, 3H, H-17).

$^{13}$C NMR (67.5 MHz, CDCl$_3$) δ (ppm): 203.9 (C-9), 173.1 (C-1), 148.2 (2C, C-11, C-20-triazole-4-aniline), 146.6 (C-20-triazole-4-aniline), 142.9 (C-13), 134.9 (C-12), 127.2 (2C, C-20-triazole-4-aniline), 121.0 (C-20-triazole-4-aniline), 118.0 (2C, C-10, C-20-triazole-4-aniline), 115.2 (2C, C-20-triazole-4-aniline, C-20-triazole-4-aniline), 103.5 (C-1'), 101.2 (C-1'''), 81.5 (C-2'''), 80.3 (C-5), 77.3 (C-3''), 74.5 (C-15), 73.2 (C-5'), 73.1 (C-4'''), 70.2 (4C, C-2', C-3', C-4', C-5'''), 69.8 (C-23), 66.5 (C-3), 61.9 (C-8'''), 60.0 (C-7'''), 47.5 (C-20), 44.7 (2C, C-8, C-14), 41.7 (2C, C-7', 8'), 40.6 (C-4), 39.5 (C-2), 33.2 (C-7), 32.8 (C-6), 27.1 (C-19), 25.5 (C-16), 17.8 (2C, C-6', C-6'''), 17.7 (C-21), 12.8 (C-22), 9.6 (C-17), 9.0 (C-18).

20-(4-(4-chlorobutyl)-1H-1,2,3-triazol-1-yl)-20-deoxodesmycosin (YT19)

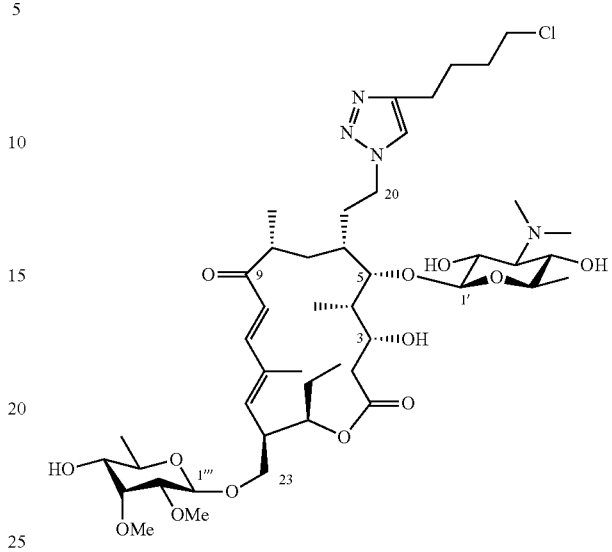

Yield: 54%

HRFABMS: calcd. for $C_{45}H_{76}O_{13}N_4C_1$: 915.5097 [M+H]. found m/z: 915.5129 [M+H]$^+$.

IR (KBr)vcm$^{-1}$: 3433 (—OH), 2933 (C—H), 1722 (C=O).

$^1$H NMR (270 MHz, CDCl$_3$) δ (ppm): 7.35 (s, 1H, H-20-triazole-1-chlorobutyl), 7.14 (d, J=15.2 Hz, 1H, H-11), 6.19 (d, J=15.2 Hz, 1H, H-10), 5.83 (d, J=10.2 Hz, 1H, H-13), 4.94 (br. dt, J=8.6 Hz, 1H, H-15), 4.54 (d, J=7.9 Hz, 1H, H-1'''), 4.33-4.31 (m, 3H, H-20, H-1'), 3.97 (dd, J=9.4, 3.7 Hz, 1H, H-23), 3.77-3.67 (m, 2H, H-5, H-3'''), 3.59 (s, 3H, 3'''-OCH$_3$), 3.57-3.49 (m, 6H, H-3, H-23, H-2', H-5''', H-20-triazole-1-chlorobutyl), 3.45 (s, 3H, 2'''-OCH$_3$), 3.32 (m, 1H, H-5'), 3.16 (d, J=8.9 Hz, 1H, H-4'''), 3.08 (t, J=9.4 Hz, 1H, H-4'), 3.00 (dd, J=7.9, 2.6, 1H, H-2'''), 2.93 (m, 1H, H-14), 2.76 (m, 2H, H-20-triazole-1-chlorobutyl), 2.60 (m, 1H, H-8), 2.49 (s, 6H, 3'-N(CH$_3$)$_2$), 2.43-2.35 (m, 2H, H-2, H-3'), 2.26-2.15 (m, 2H, H-6, H-19), 1.83-1.88 (m, 2H, H-2, H-16), 1.73 (s, 3H, H-22), 1.65-1.45 (m, 4H, H-4, H-7, H-16), 1.23 (d, J=6.3 Hz, 3H, H-6'), 1.20 (d, J=6.0 Hz, 3H, H-6'''), 1.16 (d, J=6.6 Hz, 3H, H-21), 1.01 (d, J=6.6 Hz, 3H, H-18), 0.90 (t, J=7.3 Hz, 3H, H-17).

$^{13}$C NMR (67.5 MHz, CDCl$_3$) δ (ppm): 203.3 (C-9), 173.7 (C-1), 148.0 (C-11), 147.3 (C-20-triazole-1-chlorobutyl), 141.9 (C-13), 134.5 (C-12), 120.5 (C-20-triazole-1-chlorobutyl), 118.0 (C-10), 103.8 (C-1'), 100.9 (C-1'''), 81.7 (C-2'''), 79.7 (C-5), 77.2 (C-3''), 75.0 (C-15), 73.2 (C-5'), 72.6 (C-4'''), 70.7 (4C, C-2', C-3', C-4', C-5'''), 70.0 (C-23), 66.0 (C-3), 61.6 (C-8'''), 59.5 (C-7'''), 48.0 (C-20), 45.0 (C-14), 44.7 (C-8), 41.6 (2C, C-7', 8'), 40.6 (C-4), 39.4 (C-2), 33.8 (C-7), 33.0 (C-6), 31.9 (2C, C-20-triazole-1-chlorobutyl), 28.7 (C-19), 26.5 (C-20-triazole-1-chlorobutyl), 25.2 (C-16), 24.7 (C-20-triazole-1-chlorobutyl), 17.6 (2C, C-6', C-6'''), 17.3 (C-21), 12.8 (C-22), 9.5 (C-17), 9.2 (C-18).

20-(4-butyl-1H-1,2,3-triazol-1-yl)-20-deoxodesmycosin (YT20)

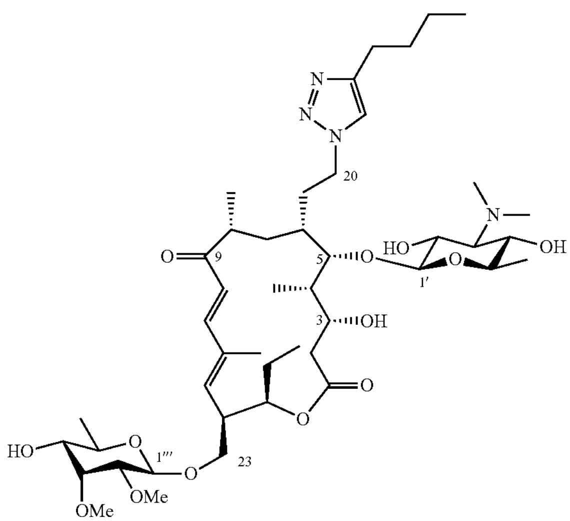

Yield: 83%

HRFABMS: calcd. for $C_{45}H_{77}O_{13}N_4$: 881.5487 [M+H]. found m/z: 881.5443 $[M+H]^+$.

IR (KBr)$\nu cm^{-1}$: 3440 (—OH), 2933 (C—H), 1722 (C═O).

$^1$H NMR (270 MHz, $CDCl_3$) δ (ppm): 7.33 (s, 1H, H-20-triazole-butyl), 7.18 (d, J=15.5 Hz, 1H, H-11), 6.20 (d, J=15.5 Hz, 1H, H-10), 5.86 (d, J=10.2 Hz, 1H, H-13), 4.96 (br. dt, J=9.2 Hz, 1H, H-15), 4.55 (d, J=7.9 Hz, 1H, H-1'''), 4.38-4.33 (m, 3H, H-20, H-1'), 4.01-3.93 (m, 4H, H-23, H-20-triazole-butyl), 3.78-3.73 (m, 2H, H-5, H-3'''), 3.61 (s, 3H, 3'''-OC$H_3$), 3.56-3.50 (m, 4H, H-3, H-23, H-2', H-5'''), 3.47 (s, 3H, 2'''-OC$H_3$), 3.38 (m, 1H, H-5'), 3.24 (d, J=9.9 Hz, 1H, H-4''), 3.17 (dd, J=9.6, 3.1 Hz, 1H, H-4'), 3.01 (dd, J=7.7, 2.8, 1H, H-2'''), 2.94 (m, 1H, H-14), 2.76-2.70 (m, 9H, H-8, 3'-N(C$H_3$)$_2$, H-20-triazole-butyl), 2.50-2.33 (m, 3H, H-2, H-3'), 2.23 (m, 1H, H-6), 2.02 (m, 3H, H-19, H-20-triazole-butyl), 1.91-1.85 (m, 2H, H-2, H-16), 1.76 (s, 3H, H-22), 1.73-1.54 (m, 4H, H-4, H-7, H-16), 1.40 (m, 2H, H-20-triazole-butyl), 1.26-1.24 (m, 6H, H-6', H-6''), 1.17 (d, J=6.9 Hz, 3H, H-21), 1.01 (d, J=6.6 Hz, 3H, H-18), 0.90 (t, J=7.3 Hz, 3H, H-17).

$^{13}$C NMR (67.5 MHz, $CDCl_3$) δ (ppm): 203.3 (C-9), 173.6 (C-1), 148.1 (C-20-triazole-butyl), 147.8 (C-11), 142.4 (C-13), 134.6 (C-12), 120.3 (C-20-triazole-butyl), 118.1 (C-10), 103.8 (C-1'), 100.9 (C-1'''), 81.6 (C-2'''), 79.7 (C-5), 77.2 (C-3'''), 74.9 (C-15), 73.2 (C-5'), 72.6 (C-4'''), 70.7 (4C, C-2', C-3', C-4', C-5'''), 69.0 (C-23), 66.5 (C-3), 61.5 (C-8'''), 59.4 (C-7'''), 47.9 (C-20), 44.9 (C-14), 44.7 (C-8), 41.5 (2C, C-7', 8'), 39.4 (2C, C-2, C-4), 33.8 (C-7), 33.0 (C-6), 31.4 (C-20-triazole-butyl), 28.9 (C-19), 25.1 (C-20-triazole-butyl), 22.2 (3C, C-16, C-20-triazole-butyl), 17.6 (2C, C-6', C-6'''), 17.2 (C-21), 13.7 (C-20-triazole-butyl), 12.8 (C-22), 9.5 (C-17), 9.1 (C-18).

20-(4-phenyl-1H-1,2,3-triazol-1-yl)-20-deoxodesmycosin (YT21)

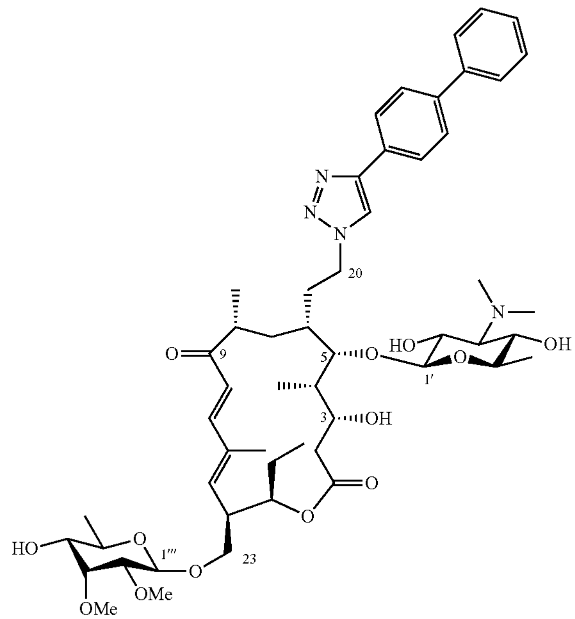

Yield: 86%

HRFABMS: calcd. for $C_{53}H_{77}O_{13}N_4$: 977.5487 [M+H]. found m/z: 977.5464 $[M+H]^+$.

IR (KBr)$\nu cm^{-1}$: 3440 (—OH), 2931 (C—H), 1718 (C═O).

$^1$H NMR (270 MHz, $CDCl_3$) δ (ppm): 8.06 (m, 2H, H-20-triazole-biphenyl), 7.94 (s, 1H, H-20-triazole-biphenyl), 7.72-7.63 (m, 4H, H-20-triazole-biphenyl), 7.48-7.42 (m, 2H, H-20-triazole-biphenyl), 7.35 (d, J=7.3 Hz, 1H, H-20-triazole-biphenyl), 6.99 (d, J=15.5 Hz, 1H, H-11), 6.17 (d, J=15.2 Hz, 1H, H-10), 5.36 (d, J=8.9 Hz, 1H, H-13), 4.80 (br. dt, J=8.7 Hz, 1H, H-15), 4.47 (m, 2H, H-20), 4.38-4.35 (m, 2H, H-1', H-1'''), 3.84-3.81 (m, 2H, H-5, H-23), 3.67 (t, J=2.8 Hz, 1H, H-3'''), 3.59 (s, 3H, 3'''-OC$H_3$), 3.53-3.47 (m, 4H, H-3, H-23, H-2', H-5'''), 3.38 (s, 3H, 2'''-OC$H_3$), 3.27 (m, 1H, H-5'), 3.13-3.07 (m, 2H, H-4', H-4'''), 2.92-2.89 (m, 2H, H-14, H-2'''), 2.70 (m, 1H, H-8), 2.51 (s, 6H, 3'-N(C$H_3$)$_2$), 2.45-2.37 (m, 2H, H-2, H-3'), 2.28 (m, 1H, H-6), 2.10 (m, 1H, H-19), 1.83-1.75 (m, 2H, H-2, H-16), 1.68 (s, 3H, H-22), 1.59-1.54 (m, 4H, H-4, H-7, H-16), 1.28 (d, J=6.0 Hz, 3H, H-6'), 1.24-1.18 (m, 6H, H-6''', H-21), 1.02 (d, J=6.9 Hz, 3H, H-18), 0.89 (t, J=7.4 Hz, 3H, H-17).

$^{13}$C NMR (67.5 MHz, $CDCl_3$) δ (ppm): 203.9 (C-9), 174.0 (C-1), 148.2 (C-20-triazole-biphenyl), 147.4 (C-11), 142.8 (C-13), 140.8 (C-20-triazole-biphenyl), 135.1 (C-12), 130.1 (C-20-triazole-biphenyl), 129.1 (4C, C-20-triazole-biphenyl), 127.6 (2C, C-20-triazole-biphenyl), 127.2 (2C, C-20-triazole-biphenyl), 126.6 (2C, C-20-triazole-biphenyl), 120.0 (C-20-triazole-biphenyl), 118.4 (C-10), 103.8 (C-1'), 101.2 (C-1'''), 82.1 (C-2'''), 80.1 (C-5), 78.0 (C-3'''), 75.6 (C-15), 73.5 (C-5'), 72.9 (C-4''), 70.5 (4C, C-2', C-3', C-4', C-5'''), 69.4 (C-23), 67.0 (C-3), 61.9 (C-8'''), 59.8 (C-7'''), 48.3 (C-20), 45.2 (2C, C-8, C-14), 42.0 (2C, C-7', 8'), 41.5 (C-4), 39.6 (C-2), 32.8 (C-7), 32.4 (C-6), 28.1 (C-19), 25.8 (C-16), 18.2 (2C, C-6', C-6'''), 17.7 (C-21), 13.2 (C-22), 9.8 (C-17), 9.3 (C-18).

53
20-(4-ethoxycarbonyl-1H-1,2,3-triazol-1-yl)-20-deoxodesmycosin (YT22)

54
20-(4-(phenanthrene-8-yl)-1H-1,2,3-triazol-1-yl)-20-deoxodesmycosin (YT23)

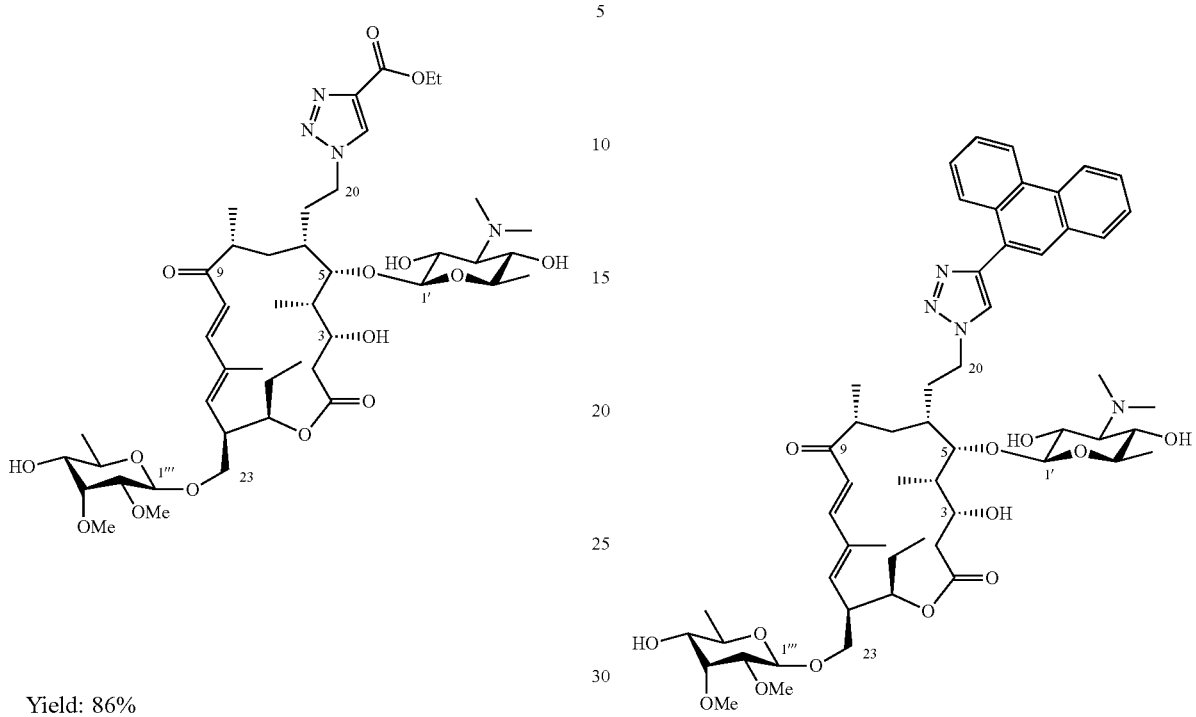

Yield: 86%

HRFABMS: calcd. for $C_{44}H_{72}O_{15}N_4Na$: 919.4892 [M+Na]. found m/z: 919.4877 [M+Na]$^+$.

IR (KBr)vcm$^{-1}$: 3452 (—OH), 2933 (C—H), 1726 (C=O).

$^1$H NMR (270 MHz, CDCl$_3$) δ (ppm): 8.15 (s, 1H, H-20-triazole-COOEt), 7.23 (d, J=15.5 Hz, 1H, H-11), 6.21 (d, J=15.5 Hz, 1H, H-10), 5.87 (d, J=9.9 Hz, 1H, H-13), 4.95 (br. dt, J=9.2 Hz, 1H, H-15), 4.54 (d, J=7.6 Hz, 1H, H-1'''), 4.46-4.38 (m, 4H, H-20, H-20-triazole-COOEt), 4.32 (m, 1H, H-1'), 3.98 (d, J=9.6 Hz, 1H, H-23), 3.55-3.65 (m, 2H, H-5, H-3'''), 3.59 (s, 3H, 3'''-OC$\underline{H}_3$), 3.59-3.46 (m, 4H, H-3, H-23, H-2', H-5'''), 3.45 (s, 3H, 2''''-OC$\underline{H}_3$), 3.30 (m, 1H, H-5'), 3.15 (d, J=9.6 Hz, 1H, H-4'''), 3.09-2.94 (m, 3H, H-14, H-4', H-2'''), 2.59 (m, 1H, H-8), 2.48 (s, 6H, 3'-N(C$\underline{H}_3$)$_2$), 2.40-2.33 (m, 4H, H-2, H-6, H-19, H-3'), 2.02-1.85 (m, 2H, H-2, H-16), 1.75 (s, 3H, H-22), 1.63-1.54 (m, 4H, H-4, H-7, H-16), 1.39 (dt, J=7.3, 3.0 Hz, 2H, H-20-triazole-COO$\underline{Et}$), 1.24 (d, J=5.0 Hz, 3H, H-6'''), 1.19-1.17 (m, 6H, H-21, H-6'), 1.01 (d, J=6.3 Hz, 3H, H-18), 0.90 (t, J=6.9 Hz, 3H, H-17).

$^{13}$C NMR (67.5 MHz, CDCl$_3$) δ (ppm): 203.7 (C-9), 174.4 (C-1), 161.1 (C-20-triazole-$\underline{C}$OOEt), 148.3 (C-11), 142.8 (C-13), 140.3 (C-20-$\underline{triazole}$-COOEt), 135.2 (C-12), 127.6 (C-20-$\underline{triazole}$-COOEt), 118.3 (C-10), 103.8 (C-1'), 101.8 (C-1'''), 82.1 (C-2'''), 80.1 (C-5), 77.3 (C-3'''), 75.6 (C-15), 73.7 (C-5'''), 73.0 (C-4''), 70.7 (4C, C-2', C-3', C-4', C-5'''), 69.4 (C-23), 67.2 (C-3), 62.0 (C-20-triazole-COO$\underline{Et}$), 61.3 (C-8'''), 59.9 (C-7'''), 49.1 (C-20), 45.3 (2C, C-8, C-14), 42.0 (2C, C-7', 8'), 39.5 (2C, C-2, C-4), 33.8 (C-7), 33.0 (C-6), 28.9 (C-19), 25.7 (C-16), 18.1 (2C, C-6', C-6'''), 17.6 (C-21), 14.6 (C-20-triazole-COO$\underline{Et}$), 13.2 (C-22), 10.0 (C-17), 9.6 (C-18).

Yield: 93%

HRFABMS: calcd. for $C_{55}H_{77}O_{13}N_4$: 1001.5487 [M+H]. found m/z: 1001.5475 [M+H]$^+$.

IR (KBr)vcm$^{-1}$: 3444 (—OH), 2929 (C—H), 1720 (C=O).

$^1$H NMR (270 MHz, CDCl$_3$) δ (ppm): 8.80-8.64 (m, 3H, H-20-triazole-phenanthrene), 8.18 (s, 1H, H-20-triazole-phenanthrene), 8.02 (s, 1H, H-20-triazole-phenanthrene), 7.98 (d, J=7.6 Hz, 1H, H-20-triazole-phenanthrene), 7.72-7.59 (m, 4H, H-20-triazole-phenanthrene), 6.95 (d, J=15.2 Hz, 1H, H-11), 6.16 (d, J=15.5 Hz, 1H, H-10), 5.18 (br. d, 1H, H-13), 4.67 (m, 1H, H-15), 4.56 (m, 2H, H-20), 4.45 (d, J=7.9 Hz, 1H, H-1'''), 4.38 (d, J=7.3 Hz, 1H, H-1'), 3.90 (d, J=9.6 Hz, 1H, H-23), 3.74 (m, 1H, H-5), 3.76 (t, J=3.0 Hz, 1H, H-3'''), 3.63 (s, 3H, 3'''-OC$\underline{H}_3$), 3.58-3.48 (m, 4H, H-3, H-23, H-2', H-5'''), 3.37 (m, 1H, H-5'), 3.26 (s, 3H, 2''''-OC$\underline{H}_3$), 3.16-3.06 (m, 2H, H-4', H-4'''), 2.88 (dd, J=7.4, 2.2, 1H, H-2''), 2.86 (m, 1H, H-14), 2.67 (m, 1H, H-8), 2.50 (s, 6H, 3'-N(C$\underline{H}_3$)$_2$), 2.44-2.37 (m, 2H, H-2, H-3'), 2.20-2.00 (m, 2H, H-6, H-19), 1.88-1.77 (m, 2H, H-2, H-16), 1.66 (s, 3H, H-22), 1.60-1.58 (m, 4H, H-4, H-7, H-16), 1.30-1.25 (m, 6H, H-6', H-6'''), 1.18 (d, J=6.6 Hz, 3H, H-21), 1.05 (d, J=6.9 Hz, 3H, H-18), 0.87 (t, J=7.2 Hz, 3H, H-17).

20-(4-(4-phenoxyphenyl)-1H-1,2,3-triazol-1-yl)-20-deoxodesmycosin (YT24)

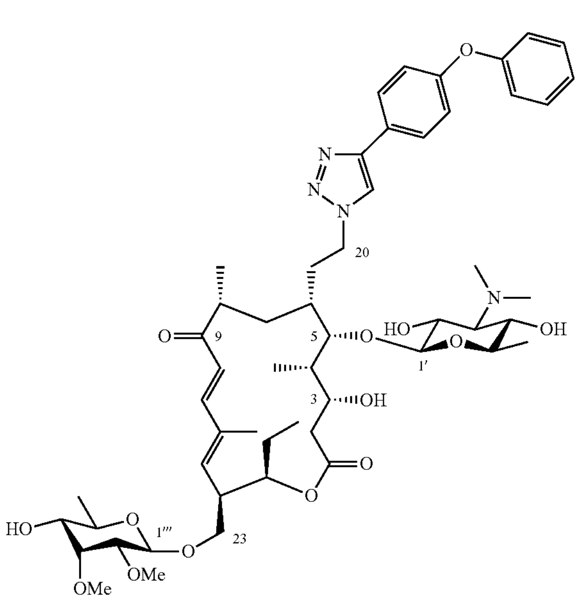

Yield: 85%

HRFABMS: calcd. for $C_{53}H_{77}O_{14}N_4$: 993.5436 [M+H]. found m/z: 993.5455 $[M+H]^+$.

IR (KBr)νcm$^{-1}$: 3444 (—OH), 2931 (C—H), 1720 (C═O).

$^1$H NMR (270 MHz, $CDCl_3$) δ (ppm): 7.94 (d, J=8.3 Hz, 2H, H-20-triazole-Ph-O-Ph), 7.85 (s, 1H, H-20-triazole-Ph-O-Ph), 7.37-7.31 (m, 2H, H-20-triazole-Ph-O-Ph), 7.13-7.03 (m, 5H, H-20-triazole-Ph-O-Ph), 6.99 (d, J=15.5 Hz, 1H, H-11), 6.17 (d, J=15.1 Hz, 1H, H-10), 5.45 (d, J=10.4 Hz, 1H, H-13), 4.86 (br. dt, J=9.2 Hz, 1H, H-15), 4.57 (d, J=7.9 Hz, 1H, H-1'''), 4.46 (m, 2H, H-20), 4.35 (d, J=7.2 Hz, 1H, H-1'), 3.95 (dd, J=9.5, 4.2 Hz, 1H, H-23), 3.82 (d, J=9.9 Hz, 1H, H-5), 3.72 (t, J=2.6 Hz, 1H, H-3'''), 3.59 (s, 3H, 3'''-$OCH_3$), 3.53-3.45 (m, 5H, H-3, H-23, H-2', H-5', H-5'''), 3.43 (s, 3H, 2'''-$OCH_3$), 3.14 (dd, J=9.5, 3.1 Hz, 1H, H-4'''), 3.08 (t, J=9.0, H-4'), 3.00 (dd, J=7.7, 2.8, 1H, H-2'''), 2.91 (m, 1H, H-14), 2.62 (m, 1H, H-8), 2.50 (s, 6H, 3'-$N(CH_3)_2$), 2.47-2.37 (m, 2H, H-2, H-3'), 2.26 (m, 1H, H-6), 2.08 (m, 1H, H-19), 1.86-1.76 (m, 2H, H-2, H-16), 1.71 (s, 3H, H-22), 1.57-1.42 (m, 4H, H-4, H-7, H-16), 1.27 (d, J=5.9 Hz, 3H, H-6'), 1.23 (d, J=5.9 Hz, 3H, H-6'''), 1.18 (d, J=6.6 Hz, 3H, H-21), 1.02 (d, J=6.6 Hz, 3H, H-18), 0.91 (t, J=7.3 Hz, 3H, H-17).

$^{13}$C NMR (67.5 MHz, $CDCl_3$) δ (ppm): 203.2 (C-9), 173.6 (C-1), 156.9 (C-20-triazole-Ph-O-Ph), 156.7 (C-20-triazole-Ph-O-Ph), 147.7 (C-11), 146.9 (C-20-triazole-Ph-O-Ph), 142.3 (C-13), 134.6 (C-12), 134.6 (3C, C-20-triazole-Ph-O-Ph), 127.3 (C-20-triazole-Ph-O-Ph), 126.1 (C-20-triazole-Ph-O-Ph), 123.1 (C-20-triazole-Ph-O-Ph), 119.0 (2C, C-20-triazole-Ph-O-Ph), 119.0 (3C, C-20-triazole-Ph-O-Ph, C-20-triazole-Ph-O-Ph), 118.6 (C-10), 103.8 (C-1'), 101.0 (C-1'''), 81.6 (C-2''), 79.6 (C-5), 77.2 (C-3'''), 75.1 (C-15), 73.1 (C-5'), 72.5 (C-4'''), 70.5 (4C, C-2', C-3', C-4', C-5'''), 69.0 (C-23), 66.8 (C-3), 61.5 (C-8'''), 59.3 (C-7'''), 47.8 (C-20), 44.7 (2C, C-8, C-14), 41.5 (2C, C-7', 8'), 40.5 (C-4), 39.2 (C-2), 32.8 (C-7), 32.4 (C-6), 27.8 (C-19), 25.1 (C-16), 17.7 (2C, C-6', C-6'''), 17.6 (C-21), 12.8 (C-22), 9.4 (C-17), 9.2 (C-18).

20-(4-(2,4,5-trimethylphenyl)-1H-1,2,3-triazol-1-yl)-20-deoxodesmycosin (YT25)

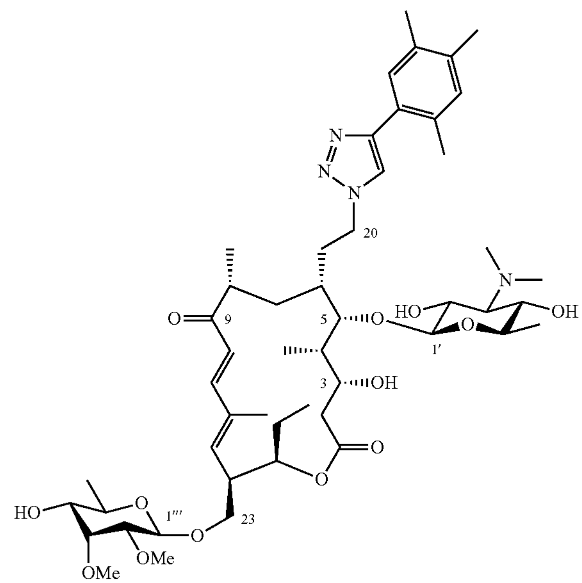

Yield: 73%

HRFABMS: calcd. for C50$H_{79}O_{13}N_4$: 943.5644 [M+H]. found m/z: 943.5643 $[M+H]^+$.

IR (KBr)νcm$^{-1}$: 3442 (—OH), 2931 (C—H), 1716 (C═O).

$^1$H NMR (270 MHz, $CDCl_3$) δ (ppm): 7.67 (s, 1H, H-20-triazole-$Ph(CH_3)_3$), 7.62 (s, 1H, H-20-triazole-$Ph(CH_3)_3$), 6.99 (s, 1H, H-20-triazole-$Ph(CH_3)_3$), 6.96 (d, J=15.5 Hz, 1H, H-11), 6.14 (d, J=15.2 Hz, 1H, H-10), 5.39 (d, J=9.2 Hz, 1H, H-13), 4.81 (br. dt, J=9.2 Hz, 1H, H-15), 4.49 (d, J=7.6 Hz, 1H, H-1'''), 4.40 (m, 2H, H-20), 4.30 (d, J=7.2 Hz, 1H, H-1'), 3.88 (dd, J=9.3, 4.1 Hz, 1H, H-23), 3.76 (d, J=9.6 Hz, 1H, H-5), 3.69 (s, 1H, H-3'''), 3.56 (s, 3H, 3'''-$OCH_3$), 3.52-3.27 (m, 5H, H-3, H-23, H-2', H-5', H-5'''), 3.37 (s, 3H, 2'''-$OCH_3$), 3.10 (dd, J=8.9, 2.6 Hz, 1H, H-4'''), 3.05 (d, J=8.9 Hz, 1H, H-4'), 2.93 (dd, J=8.0, 2.5, 1H, H-2'''), 2.85 (m, 1H, H-14), 2.59 (m, 1H, H-8), 2.45-2.43 (m, 9H, 3'-$N(CH_3)_2$, H-20-triazole-$Ph(CH_3)_3$), 2.37-2.33 (m, 2H, H-2, H-3'), 2.24-2.22 (m, 7H, H-6, H-20-triazole-$Ph(CH_3)_3$), 2.01 (m, 1H, H-19), 1.85-1.78 (m, 2H, H-2, H-16), 1.66 (s, 3H, H-22), 1.56-1.51 (m, 4H, H-4, H-7, H-16), 1.20 (d, J=6.3 Hz, 3H, H-6'), 1.18 (d, J=7.6 Hz, 3H, H-6'''), 1.12 (d, J=6.6 Hz, 3H, H-21), 0.99 (d, J=6.6 Hz, 3H, H-18), 0.86 (t, J=7.1 Hz, 3H, H-17).

$^{13}$C NMR (67.5 MHz, $CDCl_3$) δ (ppm): 203.7 (C-9), 173.7 (C-1), 147.7 (C-11), 146.7 (C-20-triazole-$Ph(CH_3)_3$), 142.0 (C-13), 135.8 (C-12), 134.7 (C-20-triazole-$Ph(CH_3)_3$), 133.5 (C-20-triazole-$Ph(CH_3)_3$), 132.5 (C-20-triazole-$Ph(CH_3)_3$), 132.0 (C-20-triazole-$Ph(CH_3)_3$), 130.0 (C-20-triazole-$Ph(CH_3)_3$), 127.3 (C-20-triazole-$Ph(CH_3)_3$), 121.0 (C-20-triazole-$Ph(CH_3)_3$), 118.1 (C-10), 103.5 (C-1'), 100.9 (C-1'''), 81.6 (C-2'''), 79.7 (C-5), 77.2 (C-3'''), 75.1 (C-15), 73.1 (C-5'), 72.5 (C-4'''), 70.3 (4C, C-2', C-3', C-4', C-5'''), 69.0 (C-23), 66.8 (C-3), 61.5 (C-8'''), 59.4 (C-7'''), 47.9 (C-20), 44.7 (2C, C-8, C-14), 41.5 (2C, C-7', 8'), 40.5 (C-4), 39.2 (C-2), 33.2 (C-7), 32.8 (C-6), 27.9 (C-19), 25.2 (C-16), 20.6 (C-20-triazole-$Ph(CH_3)_3$), 19.1 (2C, C-6', C-6'''), 19.0 (C-20-triazole-$Ph(CH_3)_3$), 17.6 (C-20-triazole-$Ph(CH_3)_3$), 17.5 (C-21), 12.8 (C-22), 9.4 (C-17), 9.3 (C-18).

20-(4-(4-t-butylphenyl)-1H-1,2,3-triazol-1-yl)-20-deoxodesmycosin (YT26)

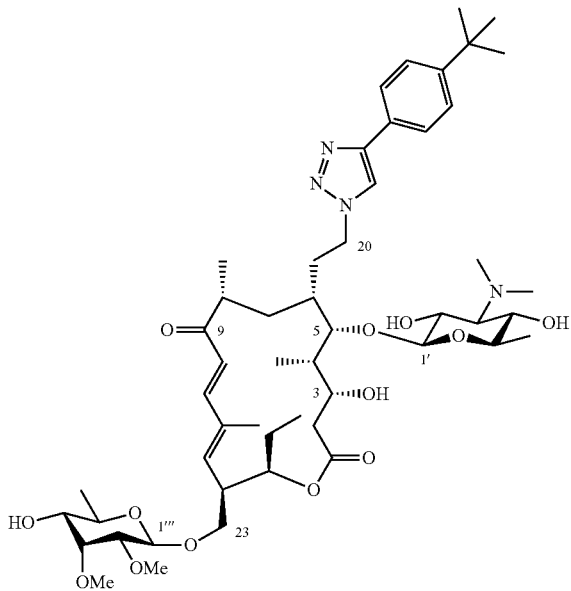

Yield: 88%

HRFABMS: calcd. for $C_{51}H_{81}O_{13}N_4$: 957.5800 [M+H]. found m/z: 957.5789 [M+H]$^+$.

IR (KBr)νcm$^{-1}$: 3446 (—OH), 2967 (C—H), 1724 (C=O).

$^1$H NMR (270 MHz, CDCl$_3$) δ (ppm): 7.84-7.82 (m, 3H, H-20-triazole-<u>Ph</u>-C(CH$_3$)$_3$, H-20-<u>triazole</u>-Ph-C(CH$_3$)$_3$), 7.42 (d, 2H, H-20-triazole-<u>Ph</u>-C(CH$_3$)$_3$), 6.97 (d, J=15.5 Hz, 1H, H-11), 6.15 (d, J=15.5 Hz, 1H, H-10), 5.50 (d, J=10.2 Hz, 1H, H-13), 4.84 (br. dt, J=8.5 Hz, 1H, H-15), 4.49 (d, J=7.6 Hz, 1H, H-1'''), 4.39 (m, 2H, H-20), 4.32 (d, J=7.3 Hz, 1H, H-1'), 3.89 (dd, J=9.4, 4.5 Hz, 1H, H-23), 3.76 (d, J=9.6 Hz, 1H, H-5), 3.69 (s, 1H, H-3'''), 3.56 (s, 3H, 3'''-OC<u>H</u>$_3$), 3.51-3.29 (m, 5H, H-3, H-23, H-2', H-5', H-5'''), 3.40 (s, 3H, 2'''-OC<u>H</u>$_3$), 3.15-3.08 (m, 2H, H-4', H-4''), 2.95 (dd, J=7.9, 2.7, 1H, H-2'''), 2.89 (m, 1H, H-14), 2.64 (m, 1H, H-8), 2.47 (s, 6H, 3'-N(C<u>H</u>$_3$)$_2$), 2.43-2.37 (m, 2H, H-2, H-3'), 2.22 (m, 1H, H-6), 1.98 (m, 1H, H-19), 1.84-1.78 (m, 2H, H-2, H-16), 1.67 (s, 3H, H-22), 1.53-1.56 (m, 4H, H-4, H-7, H-16), 1.31 (s, 9H, H-20-triazole-Ph-C(C<u>H</u>$_3$)$_3$), 1.23-1.21 (m, 6H, H-6', H-6'''), 1.13 (d, J=6.6 Hz, 3H, H-21), 0.99 (d, J=6.3 Hz, 3H, H-18), 0.87 (t, J=7.1 Hz, 3H, H-17).

$^{13}$C NMR (67.5 MHz, CDCl$_3$) δ (ppm): 203.5 (C-9), 173.6 (C-1), 150.6 (C-20-triazole-<u>Ph</u>-C(CH$_3$)$_3$), 147.8 (C-11), 147.4 (C-20-<u>triazole</u>-Ph-C(CH$_3$)$_3$), 142.0 (C-13), 134.6 (C-12), 127.9 (C-20-triazole-<u>Ph</u>-C(CH$_3$)$_3$), 125.4 (4C, C-20-triazole-<u>Ph</u>-C(CH$_3$)$_3$), 119.1 (C-20-<u>triazole</u>-Ph-C(CH$_3$)$_3$), 118.1 (C-10), 103.5 (C-1'), 100.9 (C-1'''), 81.7 (C-2'''), 79.6 (C-5), 77.2 (C-3'''), 75.2 (C-15), 73.2 (C-5'), 72.5 (C-4'''), 70.3 (4C, C-2', C-3', C-4', C-5'''), 69.3 (C-23), 66.7 (C-3), 61.5 (C-8'''), 59.4 (C-7''), 47.9 (C-20), 44.8 (2C, C-8, C-14), 41.5 (2C, C-7', 8'), 40.5 (C-4), 39.2 (C-2), 34.4 (C-20-triazole-Ph-<u>C</u>(CH$_3$)$_3$), 33.2 (C-7), 32.8 (C-6), 31.2 (3C, C-20-triazole-Ph-C(<u>C</u>H$_3$)$_3$), 28.1 (C-19), 25.3 (C-16), 17.7 (2C, C-6', C-6'''), 17.5 (C-21), 12.8 (C-22), 9.4 (C-17), 9.3 (C-18).

20-(4-(4-pentyloxyphenyl)-1H-1,2,3-triazol-1-yl)-20-deoxodesmycosin (YT27)

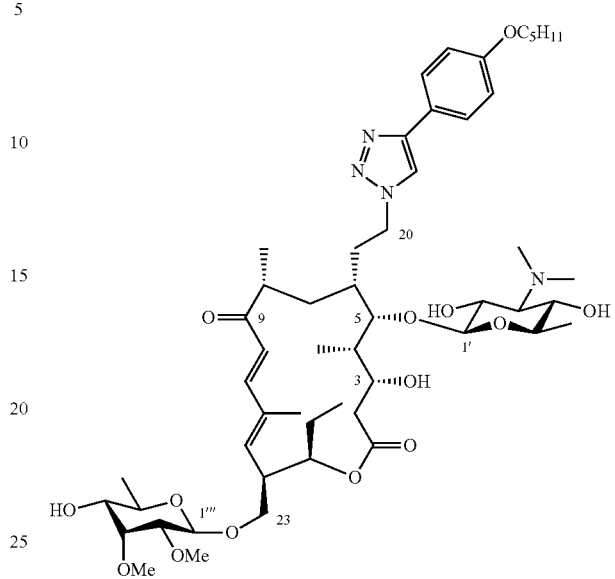

Yield: 86%

HRFABMS: calcd. for $C_{52}H_{83}O_{14}N_4$: 987.5906 [M+H]. found m/z: 987.5934 [M+H]$^+$.

IR (KBr)νcm$^{-1}$: 3455 (—OH), 2933 (C—H), 1720 (C=O).

$^1$H NMR (270 MHz, CDCl$_3$) δ (ppm): 7.82 (d, J=8.2 Hz, 2H, H-20-triazole-<u>Ph</u>-O—C$_5$H$_{11}$), 7.76 (s, 1H, H-20-<u>triazole</u>-Ph-O—C$_5$H$_{11}$), 7.00-6.92 (m, 3H, H-20-triazole-<u>Ph</u>-O—C$_5$H$_{11}$, H-11), 6.13 (d, J=15.2 Hz, 1H, H-10), 5.39 (d, J=9.9 Hz, 1H, H-13), 4.83 (br. dt, J=9.4 Hz, 1H, H-15), 4.51 (d, J=7.6 Hz, 1H, H-1'''), 4.40 (m, 2H, H-20), 4.32 (d, J=7.3 Hz, 1H, H-1'), 3.98-3.88 (m, 3H, H-23, H-20-triazole-Ph-O—C$_5$<u>H</u>$_{11}$), 3.76 (d, J=9.5 Hz, 1H, H-5), 3.70 (t, J=2.8 Hz, 1H, H-3'''), 3.58 (s, 3H, 3'''-OC<u>H</u>$_3$), 3.52-3.31 (m, 5H, H-3, H-23, H-2', H-5', H-5'''), 3.40 (s, 3H, 2'''-OC<u>H</u>$_3$), 3.14 (dd, J=9.3, 3.2 Hz, 1H, H-4''), 3.07 (t, J=9.3, H-4'), 2.96 (dd, J=8.0, 2.7, 1H, H-2'''), 2.86 (m, 1H, H-14), 2.61 (m, 1H, H-8), 2.49 (s, 6H, 3'-N(C<u>H</u>$_3$)$_2$), 2.41-2.36 (m, 2H, H-2, H-3'), 2.24 (m, 1H, H-6), 2.00 (m, 1H, H-19), 1.82-1.71 (m, 4H, H-2, H-16, H-20-triazole-Ph-O—C$_5$<u>H</u>$_{11}$), 1.66 (s, 3H, H-22), 1.53-1.56 (m, 4H, H-4, H-7, H-16), 1.45-1.32 (m, 4H, H-20-triazole-Ph-O—C$_5$<u>H</u>$_{11}$), 1.24-1.22 (m, 6H, H-6', H-6'''), 1.14 (d, J=6.9 Hz, 3H, H-21), 0.99 (d, J=6.7 Hz, 3H, H-18), 0.92-0.85 (m, 6H, H-17, H-20-triazole-Ph-O—C$_5$<u>H</u>$_{11}$).

$^{13}$C NMR (67.5 MHz, CDCl$_3$) δ (ppm): 203.8 (C-9), 174.0 (C-1), 159.1 (C-20-triazole-<u>Ph</u>-O—C$_5$H$_{11}$), 148.0 (C-11), 147.8 (C-20-<u>triazole</u>-Ph-O—C$_5$H$_{11}$), 142.7 (C-13), 135.1 (C-12), 127.4 (2C, C-20-triazole-<u>Ph</u>-O—C$_5$H$_{11}$), 123.6 (C-20-<u>triazole</u>-Ph-O—C$_5$H$_{11}$), 118.9 (C-20-triazole-<u>Ph</u>-O—C$_5$H$_{11}$), 118.4 (C-10), 114.9 (2C, C-20-triazole-<u>Ph</u>-O—C$_5$H$_{11}$), 103.8 (C-1'), 101.2 (C-1'''), 81.9 (C-2'''), 80.0 (C-5), 77.6 (C-3'''), 75.4 (C-15), 73.5 (C-5'), 72.9 (C-4'''), 70.3 (4C, C-2', C-3', C-4', C-5'''), 68.2 (C-23), 67.3 (C-3), 61.9 (C-8'''), 59.7 (C-7''), 48.2 (C-20), 45.1 (2C, C-8, C-14), 41.2 (2C, C-7', 8'), 40.8 (C-4), 39.6 (C-2), 33.2 (C-7), 32.8 (C-6), 29.1 (C-20-triazole-Ph-O—<u>C</u>$_5$H$_{11}$), 28.3 (2C, C-19, C-20-triazole-Ph-O—<u>C</u>$_5$H$_{11}$), 25.7 (C-16), 22.6

(C-20-triazole-Ph-O—$\underline{C}_5H_{11}$), 18.0 (2C, C-6', C-6'''), 17.5 (C-21), 14.2 (C-20-triazole-$\underline{Ph}$), 13.1 (C-22), 9.8 (C-17), 9.3 (C-18).

20-(4-(1-methyl-1H-benzotriazole)-1H-1,2,3-triazol-1-yl)-20-deoxodesmycosin (YT28)

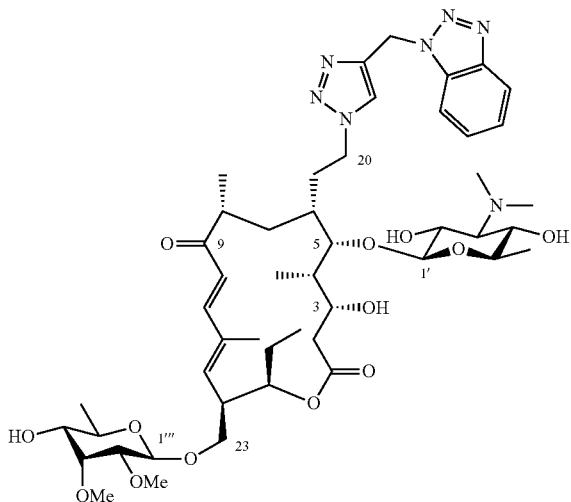

Yield: 96%

HRFABMS: calcd. for $C_{48}H_{73}O_{13}N_7Na$: 978.5164 [M+Na]. found m/z: 978.5139 [M+Na]$^+$.

IR (KBr)vcm$^{-1}$: 3438 (—OH), 2931 (C—H), 1720 (C=O).

$^1$H NMR (270 MHz, CDCl$_3$) δ (ppm): 8.00 (d, J=8.2 Hz, 1H, H-20-triazole-CH$_2$-$\underline{benzotriazole}$), 7.75 (d, J=8.2 Hz, H-20-triazole-CH$_2$-$\underline{benzotriazole}$), 7.58 (s, 1H, H-20-triazole-CH$_2$-benzotriazole), 7.44 (t, 1H, J=7.8 Hz, H-20-triazole-CH$_2$-$\underline{benzotriazole}$), 7.32 (t, J=7.8 Hz, 1H, H-20-triazole-CH$_2$-$\underline{benzotriazole}$), 7.14 (d, J=15.5 Hz, 1H, H-11), 6.16 (d, J=15.5 Hz, 1H, H-10), 5.99 (s, 2H, H-20-triazole-C$\underline{H}_2$-$\underline{benzotriazole}$), 5.88 (d, J=9.9 Hz, 1H, H-13), 4.96 (br. dt, J=9.6 Hz, 1H, H-15), 4.53 (d, J=7.9 Hz, 1H, H-1'''), 4.29-4.26 (m, 3H, H-20, H-1'), 3.97 (dd, J=9.3, 3.3 Hz, 1H, H-23), 3.70-3.66 (m, 2H, H-5, H-3'''), 3.56 (s, 3H, 3'''-OC$\underline{H}_3$), 3.51-3.38 (m, 4H, H-3, H-23, H-2', H-5'''), 3.43 (s, 3H, 2''''-OC$\underline{H}_3$), 3.22 (m, 1H, H-5'), 3.09 (dd, J=9.4, 2.8 Hz, 1H, H-4''), 3.03 (t, J=9.6, H-4'), 2.95 (dd, J=7.9, 3.0, 1H, H-2''), 2.86 (m, 1H, H-14), 2.50 (m, 1H, H-8), 2.48 (s, 6H, 3'-N(C$\underline{H}_3$)$_2$), 2.42-2.32 (m, 2H, H-2, H-3'), 2.23 (m, 1H, H-6), 1.89-1.83 (m, 2H, H-2, H-16, H-19), 1.72 (s, 3H, H-22), 1.60-1.52 (m, 4H, H-4, H-7, H-16), 1.22 (d, J=5.9 Hz, 3H, H-6'), 1.13 (d, J=6.6 Hz, 3H, H-6''), 1.00-0.97 (m, 6H, H-18, H-21), 0.90 (t, J=7.1 Hz, 3H, H-17).

$^{13}$C NMR (67.5 MHz, CDCl$_3$) δ (ppm): 203.5 (C-9), 174.1 (C-1), 148.2 (C-11), 146.1 (C-20-triazole-CH$_2$-benzotriazole), 142.8 (C-13), 141.9 (C-20-triazole-CH$_2$-$\underline{benzotriazole}$), 134.9 (C-20-triazole-CH$_2$-$\underline{benzotriazole}$), 132.9 (2C, C-12, C-20-triazole-CH$_2$-$\underline{benzotriazole}$), 127.8 (C-20-triazole-CH$_2$-$\underline{benzotriazole}$), 124.3 (C-20-triazole-CH$_2$-$\underline{benzotriazole}$), 122.9 (C-20-triazole-CH$_2$-$\underline{benzotriazole}$), 119.7 (C-20-triazole-CH$_2$-$\underline{benzotriazole}$), 118.1 (C-10), 110.6 (C-20-triazole-$\underline{C}$H$_2$-benzotriazole), 103.5 (C-1'), 101.2 (C-1'''), 81.9 (C-2''''), 80.1 (C-5), 77.7 (C-3'''), 75.4 (C-15), 73.4 (C-5'), 72.9 (C-4'''), 70.3 (4C, C-2', C-3', C-4', C-5'''), 69.1 (C-23), 66.8 (C-3), 61.9 (C-8'''), 59.7 (C-7'''), 48.8 (C-20), 45.2 (C-14), 44.0 (C-8), 41.9 (2C, C-7', 8'), 40.5 (C-4), 39.6 (C-2), 33.2 (C-7), 32.8 (C-6), 28.9 (C-19), 25.4 (C-16), 17.9 (2C, C-6', C-6'''), 17.5 (C-21), 13.1 (C-22), 9.8 (C-17), 9.3 (C-18).

20-(4-(4-dimethylaminophenyl)-1H-1,2,3-triazol-1-yl)-20-deoxodesmycosin (YT29)

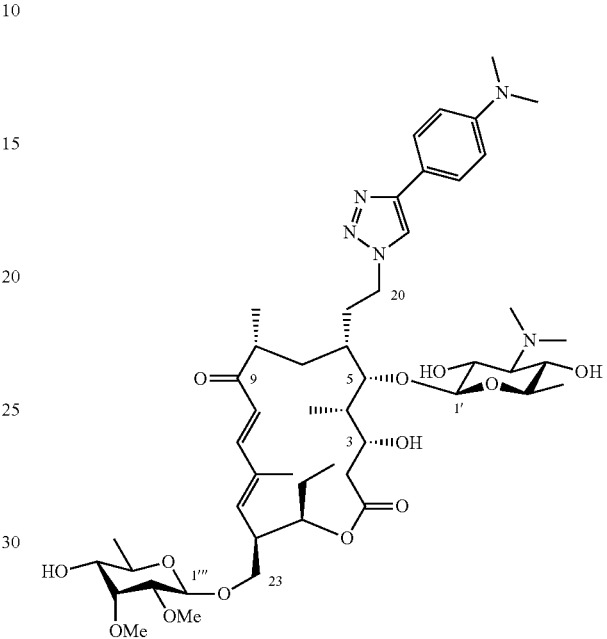

Yield: 89%

HRFABMS: calcd. for $C_{49}H_{77}O_{13}N_5Na$: 966.5416 [M+Na]. found m/z: 966.5406 [M+Na]$^+$.

IR (KBr)vcm$^{-1}$: 3442 (—OH), 2931 (C—H), 1722 (C=O).

$^1$H NMR (270 MHz, CDCl$_3$) δ (ppm): 7.83 (d, J=8.2 Hz, 2H, H-20-triazole-$\underline{Ph}$-N(CH$_3$)$_2$), 7.74 (s, 1H, H-20-triazole-Ph-N(CH$_3$)$_2$), 6.98 (d, J=15.5 Hz, 1H, H-11), 6.79 (d, J=8.6 Hz, 2H, H-20-triazole-$\underline{Ph}$-N(CH$_3$)$_2$), 6.15 (d, J=15.2 Hz, 1H, H-10), 5.28 (br. d, 1H, H-13), 4.82 (br. dt, J=8.9 Hz, 1H, H-15), 4.50 (d, J=7.6 Hz, 1H, H-1'''), 4.42 (m, 2H, H-20), 4.34 (d, J=7.2 Hz, 1H, H-1'), 3.91 (dd, J=9.3, 4.1 Hz, 1H, H-23), 3.79 (d, J=9.5 Hz, 1H, H-5), 3.71 (t, J=2.8 Hz, 1H, H-3'''), 3.60 (s, 3H, 3'''-OC$\underline{H}_3$), 3.53-3.44 (m, 4H, H-3, H-23, H-2', H-5'''), 3.40 (s, 3H, 2''''-OC$\underline{H}_3$), 3.34 (m, 1H, H-5'), 3.15 (dd, J=9.5, 3.1 Hz, 1H, H-4''), 3.08 (t, J=9.4, H-4'), 2.98-2.95 (m, 7H, H-2'', H-20-triazole-Ph-N(C$\underline{H}_3$)$_2$), 2.86 (m, 1H, H-14), 2.65 (m, 1H, H-8), 2.49 (s, 6H, 3'-N(C$\underline{H}_3$)$_2$), 2.44-2.36 (m, 2H, H-2, H-3'), 2.24 (m, 1H, H-6), 2.02 (m, 1H, H-19), 1.85-1.76 (m, 2H, H-2, H-16), 1.68 (s, 3H, H-22), 1.58-1.53 (m, 4H, H-4, H-7, H-16), 1.26 (d, J=5.9 Hz, 3H, H-6'), 1.25 (d, J=6.3 Hz, 3H, H-6'''), 1.17 (d, J=6.6 Hz, 3H, H-21), 1.00 (d, J=6.6 Hz, 3H, H-18), 0.90 (t, J=7.1 Hz, 3H, H-17).

$^{13}$C NMR (67.5 MHz, CDCl$_3$) δ (ppm): 203.5 (C-9), 173.2 (C-1), 150.0 (2C, C-11, C-20-triazole-$\underline{Ph}$-N(CH$_3$)$_2$), 147.8 (C-20-$\underline{triazole}$-Ph-N(CH$_3$)$_2$), 142.4 (C-13), 134.6 (C-12), 126.7 (C-20-$\underline{triazole}$-Ph-N(CH$_3$)$_2$), 119.0 (C-20-triazole-$\underline{Ph}$-N(CH$_3$)$_2$), 118.1 (C-10), 117.7 (C-20-triazole-$\underline{Ph}$-N(CH$_3$)$_2$), 112.2 (3C, C-20-triazole-$\underline{Ph}$-N(CH$_3$)$_2$), 103.5 (C-1'), 100.8 (C-1'''), 81.5 (C-2''''), 79.7 (C-5), 77.2 (C-3'''), 76.5 (C-15), 73.1 (C-5'), 72.5 (C-4'''), 70.3 (4C, C-2', C-3', C-4', C-5'''), 69.1 (C-23), 66.5 (C-3), 61.5 (C-8'''), 59.3 (C-7'''), 47.7 (C-20), 44.7 (2C, C-14,C-8), 41.5 (2C, C-20-triazole-Ph-N(CH₃)₂), 40.3 (3C, C-4, C-7', 8'), 39.3 (C-2), 33.2 (C-7), 32.8 (C-6), 27.9 (C-19), 25.3 (C-16), 17.6 (2C, C-6', C-6'''), 17.2 (C-21), 12.7 (C-22), 9.4 (C-17), 9.0 (C-18).

20-(4-(N-methyl-methylamine)-1H-1,2,3-triazol-1-yl)-20-deoxodesmycosin (YT30)

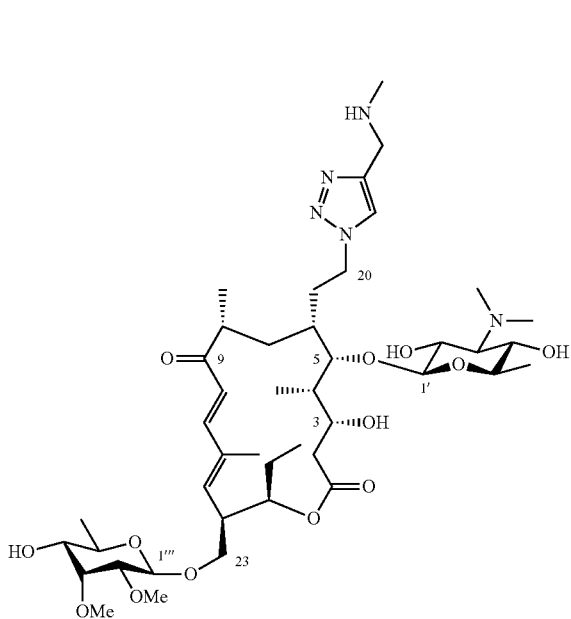

Yield: 80%

HRFABMS: calcd. for $C_{43}H_{74}O_{13}N_5$: 868.5283 [M+H]. found m/z: 968.5269 [M+H]⁺.

IR (KBr)vcm⁻¹: 3430 (—OH), 2933 (C—H), 1724 (C=O).

¹H NMR (270 MHz, CDCl₃) δ (ppm): 7.58 (s, 1H, H-20-triazole-CH₂NHCH₃), 7.15 (d, J=15.2 Hz, 1H, H-11), 6.18 (d, J=15.5 Hz, 1H, H-10), 5.85 (d, J=10.2 Hz, 1H, H-13), 4.93 (br. dt, J=9.9 Hz, 1H, H-15), 4.53 (d, J=7.9 Hz, 1H, H-1'''), 4.36 (m, 2H, H-20), 4.31 (d, J=7.2 Hz, 1H, H-1'), 3.97 (dd, J=9.6, 3.8 Hz, 1H, H-23), 3.92 (s, 1H, H-5), 3.73 (t, J=3.1 Hz, 1H, H-3'''), 3.59 (s, 3H, 3'''-OCH₃), 3.55-3.49 (m, 4H, H-3, H-23, H-2', H-5'''), 3.45 (s, 3H, 2'''-OCH₃), 3.31 (m, 1H, H-5'), 3.15 (dd, J=9.4, 3.1 Hz, 1H, H-4''), 3.10-2.85 (m, 5H, H-14, H-4', H-2''', H-20-triazole-CH₂NHCH₃), 2.50 (m, 1H, H-8), 2.48 (s, 9H, 3'-N(CH₃)₂, H-20-triazole-CH₂NHCH₃), 2.41-2.33 (m, 2H, H-2, H-3'), 2.24 (m, 1H, H-6), 1.88-1.83 (m, 3H, H-2, H-16, H-19), 1.73 (s, 3H, H-22), 1.60-1.54 (m, 4H, H-4, H-7, H-16), 1.23 (d, J=6.3 Hz, 3H, H-6'), 1.21 (d, J=6.3 Hz, 3H, H-6'''), 1.15 (d, J=6.6 Hz, 3H, H-21), 1.00 (d, J=6.6 Hz, 3H, H-18), 0.90 (t, J=7.2 Hz, 3H, H-17).

¹³C NMR (67.5 MHz, CDCl₃) δ (ppm): 203.3 (C-9), 173.5 (C-1), 148.0 (C-11), 145.8 (C-20-triazole-CH₂NHCH₃), 142.4 (C-13), 134.6 (C-12), 121.7 (C-20-triazole-CH₂NHCH₃), 118.1 (C-10), 103.8 (C-1'), 101.0 (C-1'''), 81.7 (C-2'''), 79.8 (C-5), 77.2 (2C, C-3''', C-20-triazole-Ph-CH₂NHCH₃), 75.0 (C-15), 73.2 (C-5'), 72.6 (C-4'''), 70.3 (4C, C-2', C-3', C-4', C-5'''), 69.0 (C-23), 66.3 (C-3), 61.7 (C-8'''), 59.5 (C-7'''), 48.1 (C-20), 46.2 (C-14), 45.0 (C-8), 42.3 (2C, C-7', 8'), 41.0 (C-4), 39.6 (C-2), 35.6 (C-20-triazole-Ph-CH₂NHCH₃), 33.2 (C-7), 32.8 (C-6), 27.9 (C-19), 25.2 (C-16), 17.7 (2C, C-6', C-6'''), 17.3 (C-21), 12.8 (C-22), 9.6 (C-17), 9.2 (C-18).

20-(4-(1-methyl-1-hydroxylethyl)-1H-1,2,3-triazol-1-yl)-20-deoxodesmycosin (YT32)

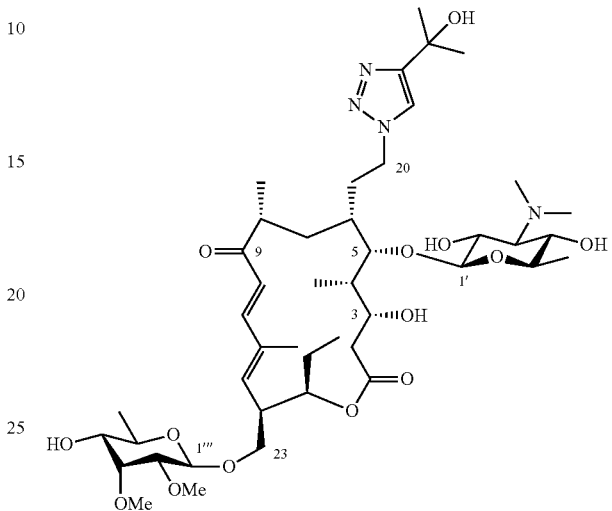

Yield: 92%

HRFABMS: calcd. for $C_{44}H_{75}O_{14}N_4$: 883.5280 [M+H]. found m/z: 883.5311 [M+H]⁺.

IR (KBr)vcm⁻¹: 3438 (—OH), 2931 (C—H), 1722 (C=O).

¹H NMR (270 MHz, CDCl₃) δ (ppm): 7.57 (s, 1H, H-20-triazole-C(CH₃)₂OH), 7.21 (d, J=15.2 Hz, 1H, H-11), 6.16 (d, J=15.5 Hz, 1H, H-10), 5.90 (d, J=10.5 Hz, 1H, H-13), 4.94 (br. dt, J=9.2 Hz, 1H, H-15), 4.58-4.45 (m, 2H, H-20, H-1'''), 4.36-4.28 (m, 2H, H-20, H-1'), 3.99 (dd, J=9.7, 3.8 Hz, H-23), 3.79 (d, J=11.6 Hz, 1H, H-5), 3.76 (t, J=3.1 Hz, 1H, H-3'''), 3.62 (s, 3H, 3'''-OCH₃), 3.56-3.44 (m, 4H, H-3, H-23, H-2', H-5'''), 3.47 (s, 3H, 2'''-OCH₃), 3.35 (m, 1H, H-5'), 3.19 (dd, J=9.0, 2.8 Hz, 1H, H-4'), 3.10 (t, J=9.4 Hz, 1H, H-4'''), 3.02 (dd, J=7.6, 2.7, 1H, H-2'''), 2.92 (m, 1H, H-14), 2.58 (m, 1H, H-8), 2.51 (s, 6H, H-3'-N(CH₃)₂), 2.44 (d, J=9.9 Hz, 1H, H-2), 2.40 (t, J=10.2 Hz, 1H, H-3'), 2.23 (m, 1H, H-6), 2.00 (m, 1H, H-19), 1.87-1.81 (m, 2H, H-2, H-16), 1.73 (s, 6H, H-20-triazole-C(CH₃)₂OH), 1.70 (s, 3H, H-22), 1.65-1.50 (m, 4H, H-4, H-7, H-16), 1.28-1.26 (m, 6H, H-6', H-6''), 1.18 (d, J=6.9 Hz, 3H, H-21), 1.03 (d, J=6.9 Hz, 3H, H-18), 0.92 (t, J=6.7 Hz, 3H, H-17).

¹³C NMR (67.5 MHz, CDCl₃) δ (ppm): 203.2 (C-9), 173.3 (C-1), 155.8 (C-20-triazole-C(CH₃)₂OH), 148.1 (C-11), 143.1 (C-13), 134.3 (C-12), 119.0 (C-20-triazole-C(CH₃)₂OH), 117.3 (C-10), 103.5 (C-1'), 100.9 (C-1'''), 81.6 (C-2'''), 79.7 (C-5), 77.2 (C-3'''), 74.9 (C-15), 73.0 (C-5'), 72.5 (C-4'''), 70.7 (4C, C-2', C-3', C-4', C-5'''), 68.7 (C-23), 67.8 (C-20-triazole-C(CH₃)₂OH), 66.1 (C-3), 61.5 (C-8'''), 59.5 (C-7'''), 47.4 (C-20), 45.0 (C-14), 44.7 (C-8), 41.5 (2C, C-7', 8'), 40.7 (C-4), 39.4 (C-2), 32.8 (C-7), 32.6 (C-6), 30.0 (2C, C-20-triazole-C(CH₃)₂OH), 28.2 (C-19), 25.1 (C-16), 17.6 (2C, C-6', C-6'''), 17.2 (C-21), 12.8 (C-22), 9.5 (C-17), 9.0 (C-18).

63
20-(4-(2-methyl-propyl)-1H-1,2,3-triazol-1-yl)-20-deoxodesmycosin (YT33)

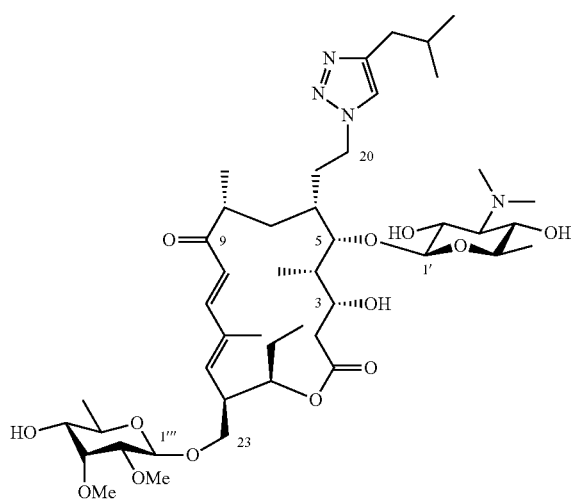

Yield: 89%

HRFABMS: calcd. for $C_{45}H_{77}O_{13}N_4$: 881.5487 [M+H]. found m/z: 881.5516 [M+H]$^+$.

IR (KBr)vcm$^{-1}$: 3438 (—OH), 2931 (C—H), 1722 (C=O).

$^1$H NMR (270 MHz, CDCl$_3$) δ (ppm): 7.31 (s, 1H, H-20-triazole-CH$_2$CH(CH$_3$)$_2$), 7.16 (d, J=15.2 Hz, 1H, H-11), 6.19 (d, J=15.5 Hz, 1H, H-10), 5.983 (d, J=9.9 Hz, 1H, H-13), 4.94 (br. dt, J=9.3 Hz, 1H, H-15), 4.52 (d, J=7.6 Hz, 1H, H-1'''), 4.37 (m, 2H, H-20), 4.31 (d, J=7.3 Hz, 1H, H-1'), 3.95 (dd, J=10.1, 4.0 Hz, H-23), 3.76-3.71 (m, 2H, H-5, H-3'''), 3.57 (s, 3H, 3'''-OCH$_3$), 3.54-3.42 (m, 4H, H-3, H-23, H-2', H-5'''), 3.44 (s, 3H, 2'''-OCH$_3$), 3.30 (m, 1H, H-5'), 3.13 (d, J=14.2 Hz, 1H, H-4'), 3.13 (t, J=9.1 Hz, 1H, H-4'''), 2.97 (dd, J=7.9, 2.8, 1H, H-2''), 2.91 (m, 1H, H-14), 2.56 (d, J=7.0 Hz, 2H, H-20-triazole-CH$_2$CH(CH$_3$)$_2$), 2.54 (m, 1H, H-8), 2.46 (s, 6H, H-3'-N(CH$_3$)$_2$), (d, J=9.9 Hz, 1H, H-2), 2.40 (t, J=10.2 Hz, 1H, H-3'), 2.23 (m, 1H, H-6), 1.97-1.83 (m, 3H, H-2, H-16, H-19), 1.72 (s, 3H, H-22), 1.59-1.56 (m, 4H, H-4, H-7, H-16), 1.22 (d, J=6.2 Hz, H-6'), 1.16-1.14 (m, 7H, H-21, H-6''', H-20-triazole-CH$_2$CH(CH$_3$)$_2$), 1.00 (d, J=6.6 Hz, 3H, H-18), 0.93-0.86 (m, 12H, H-17, H-18, H-20-triazole-CH$_2$CH(CH$_3$)$_2$).

$^{13}$C NMR (67.5 MHz, CDCl$_3$) δ (ppm): 203.3 (C-9), 173.7 (C-1), 147.7 (C-11), 146.7 (C-20-triazole-CH$_2$CH(CH$_3$)$_2$), 142.2 (C-13), 134.6 (C-12), 120.8 (C-20-triazole-CH$_2$CH(CH$_3$)$_2$), 118.0 (C-10), 103.5 (C-1'), 100.9 (C-1'''), 81.6 (C-2''), 79.7 (C-5), 77.2 (C-3'''), 74.9 (C-15), 73.2 (C-5'), 72.6 (C-4'''), 70.7 (4C, C-2', C-3', C-4', C-5'''), 68.8 (C-23), 66.1 (C-3), 61.6 (C-8'''), 59.5 (C-7'''), 47.9 (C-20), 44.8 (C-14), 44.7 (C-8), 41.5 (2C, C-7', 8'), 40.7 (C-4), 39.2 (C-2), 34.6 (C-20-triazole-CH$_2$CH(CH$_3$)$_2$), 32.8 (C-7), 32.6 (C-6), 28.5 (2C, C-19, C-20-triazole-CH$_2$CH(CH$_3$)$_2$), 25.0 (C-16), 22.3 (C-20-triazole-CH$_2$CH(CH$_3$)$_2$), 22.2 (C-20-triazole-CH$_2$CH(CH$_3$)$_2$), 17.2 (2C, C-6', C-6'''), 17.2 (C-21), 12.8 (C-22), 9.5 (C-17), 9.0 (C-18).

64
20-(4-nonyl-1H-1,2,3-triazol-1-yl)-20-deoxodesmycosin (YT34)

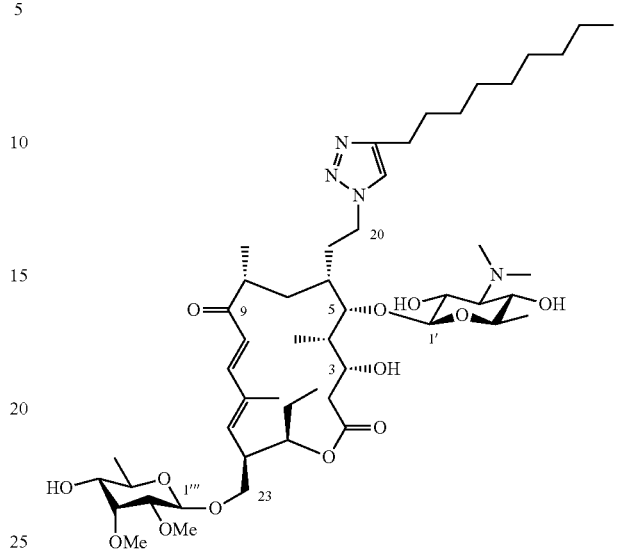

Yield: 97%

HRFABMS: calcd. for $C_{50}H_{87}O_{13}N_4$: 951.6270 [M+H]. found m/z: 951.6309 [M+H]$^+$.

IR (KBr)vcm$^{-1}$: 3440 (—OH), 2933 (C—H), 1722 (C=O).

$^1$H NMR (270 MHz, CDCl$_3$) δ (ppm): 7.25 (s, 1H, H-20-triazole-nonyl), 7.12 (d, J=14.8 Hz, 1H, H-11), 6.15 (d, J=15.6 Hz, 1H, H-10), 5.78 (d, J=10.2 Hz, 1H, H-13), 4.88 (br. dt, J=9.7 Hz, 1H, H-15), 4.48 (d, J=7.9 Hz, 1H, H-1'''), 4.20-4.40 (m, 3H, H-20, H-1'), 3.91 (dd, J=9.2, 3.4 Hz, H-23), 3.67-3.63 (m, 2H, H-5, H-3'''), 3.52 (s, 3H, 3'''-OCH$_3$), 3.45-3.43 (m, 4H, H-3, H-23, H-2', H-5'''), 3.40 (s, 3H, 2'''-OCH$_3$), 3.26 (m, 1H, H-5'), 3.11-3.06 (m, 2H, H-4', H-4'''), 2.93 (dd, J=7.6, 2.6, 1H, H-2''), 2.85 (m, 1H, H-14), 2.66-2.61 (m, 3H, H-8, H-20-triazole-nonyl), 2.42 (s, 6H, H-3'-N(CH$_3$)$_2$,), 2.40-2.29 (m, 3H, H-2, H-3'), 2.22 (m, 1H, H-19), 2.08 (m, 1H, H-6), 1.84-1.78 (m, 2H, H-2, H-16), 1.68 (s, 3H, H-22), 1.58-1.52 (m, 4H, H-4, H-7, H-16), 1.18-1.09 (m, 20H, H-6', H-6''', H-20-triazole-nonyl), 0.96 (d, J=6.3 Hz, 3H, H-21), 0.85 (d, J=6.9 Hz, 3H, H-18), 0.79 (m, 6H, H-17, H-20-triazole-nonyl).

$^{13}$C NMR (67.5 MHz, CDCl$_3$) δ (ppm): 203.2 (C-9), 173.7 (C-1), 148.0 (C-20-triazole-nonyl), 147.7 (C-11), 142.2 (C-13), 134.5 (C-12), 120.1 (C-20-triazole-nonyl), 118.0 (C-10), 103.5 (C-1'), 100.8 (C-1'''), 81.6 (C-2''), 79.7 (C-5), 77.5 (C-3'''), 76.5 (C-15), 74.9 (C-5'), 73.2 (C-4'''), 70.7 (4C, C-2', C-3', C-4', C-5'''), 68.8 (C-23), 67.9 (C-3), 61.5 (C-8'''), 59.4 (C-7'''), 47.9 (C-20), 44.8 (C-14), 44.7 (C-8), 41.4 (2C, C-7', 8'), 39.2 (2C, C-2, C-4), 33.8 (C-7), 33.0 (C-6), 31.6 (C-20-triazole-nonyl), 29.3 (C-20-triazole-nonyl), 29.1 (2C, C-20-triazole-nonyl), 29.0 (2C, C-20-triazole-nonyl), 28.9 (C-19), 25.4 (C-20-triazole-nonyl), 25.2 (C-16), 22.4 (C-20-triazole-nonyl), 17.6 (2C, C-6', C-6'''), 17.5 (C-21), 13.9 (C-20-triazole-nonyl), 12.7 (C-22), 9.4 (C-17), 8.9 (C-18).

20-(4-(3-quinoline)-1H-1,2,3-triazol-1-yl)-20-deoxodesmycosin (YT35)

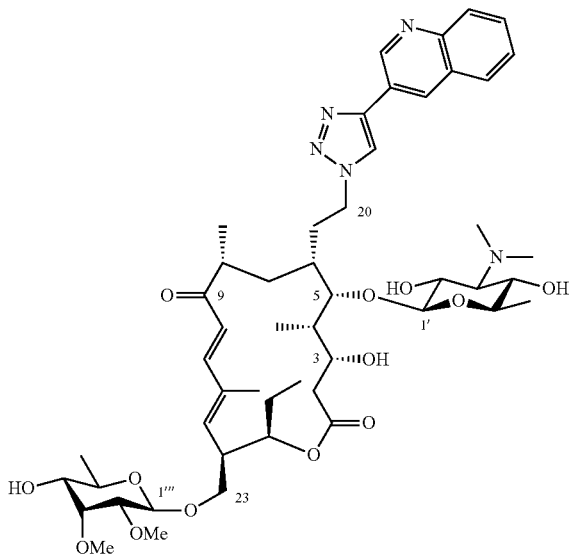

Yield: 93%

HRFABMS: calcd. for $C_{50}H_{74}O_{13}N_5$: 952.5283 [M+H]. found m/z: 952.5281 [M+H]$^+$.

IR (KBr)vcm$^{-1}$: 3436 (—OH), 2933 (C—H), 1722 (C=O).

$^1$H NMR (270 MHz, CDCl$_3$) δ (ppm): 9.55 (s, 1H, H-triazole-quinoline), 8.83 (s, 1H, H-triazole-quinoline), 8.19 (s, 1H, H-triazole-quinoline), 8.16 (s, 1H, H-triazole-quinoline), 7.97 (d, J=7.6 Hz, 1H, H-triazole-quinoline), 7.72 (t, J=7.1 Hz, 1H, H-triazole-quinoline), 7.59 (t, J=7.1 Hz, 1H, H-triazole-quinoline), 6.87 (d, J=15.5 Hz, 1H, H-11), 6.14 (d, J=15.2 Hz, 1H, H-10), 4.98 (d, J=9.2 Hz, 1H, H-13), 4.69 (br. dt, J=8.9 Hz, 1H, H-15), 4.55 (m, 2H, H-20), 4.39 (d, J=7.6 Hz, 1H, H-1'''), 4.38 (d, J=7.6 Hz, 1H, H-1'), 3.82 (d, J=9.9 Hz, 1H, H-5), 3.71 (m, 2H, H-23, H-3'''), 3.64 (s, 3H, 3'''-OCH$_3$), 3.60-3.37 (m, 4H, H-3, H-23, H-2', H-5'''), 3.33 (s, 3H, 2'''-OCH$_3$), 3.25 (m, 1H, H-5'), 3.17-3.09 (m, 2H, H-4', H-4'''), 2.90 (dd, J=7.5, 2.3, 1H, H-2'''), 2.81 (m, 1H, H-14), 2.68 (m, 1H, H-8), 2.53 (s, 6H, 3'-N(CH$_3$)$_2$), 2.47-2.39 (m, 3H, H-2, H-3'), 2.30 (m, 1H, H-6), 2.15 (m, 1H, H-19), 1.82-1.76 (m, 2H, H-2, H-16), 1.64 (s, 3H, H-22), 1.62-1.51 (m, 4H, H-4, H-7, H-16), 1.32 (d, J=5.9 Hz, 3H, H-6'), 1.27 (d, J=6.3 Hz, 3H, H-6'''), 1.16 (d, J=6.9 Hz, 3H, H-21), 1.05 (d, J=6.6 Hz, 3H, H-18), 0.89 (t, J=7.1 Hz, 3H, H-17).

$^{13}$C NMR (67.5 MHz, CDCl$_3$) δ (ppm): 203.3 (C-9), 173.5 (C-1), 150.8 (C-20-triazole-quinoline), 147.6 (C-11), 147.2 (C-20-triazole-quinoline), 144.5 (C-20-triazole-quinoline), 142.4 (C-13), 134.5 (C-12), 131.9 (C-20-triazole-quinoline), 129.2 (C-20-triazole-quinoline), 129.0 (C-20-triazole-quinoline), 128.0 (C-20-triazole-quinoline), 127.8 (C-20-triazole-quinoline), 126.9 (C-20-triazole-quinoline), 124.1 (C-20-triazole-quinoline), 120.2 (C-20-triazole-quinoline), 117.6 (C-10), 103.5 (C-1'), 100.8 (C-1'''), 81.4 (C-2'''), 79.7 (C-5), 77.5 (C-3''), 75.0 (C-15), 73.1 (C-5'), 72.5 (C-4'''), 70.2 (4C, C-2', C-3', C-4', C-5'''), 68.8 (C-23), 66.3 (C-3), 61.5 (C-8'''), 59.2 (C-7'''), 47.8 (C-20), 44.7 (2C, C-8, C-14), 41.5 (2C, C-7', 8'), 40.3 (C-4), 39.1 (C-2), 32.8 (C-7), 32.4 (C-6), 27.4 (C-19), 25.2 (C-16), 17.7 (2C, C-6', C-6'''), 17.1 (C-21), 12.7 (C-22), 9.4 (C-17), 9.0 (C-18).

20-(4-(4-butanol)-1H-1,2,3-triazol-1-yl)-20-deoxodesmycosin (YT36)

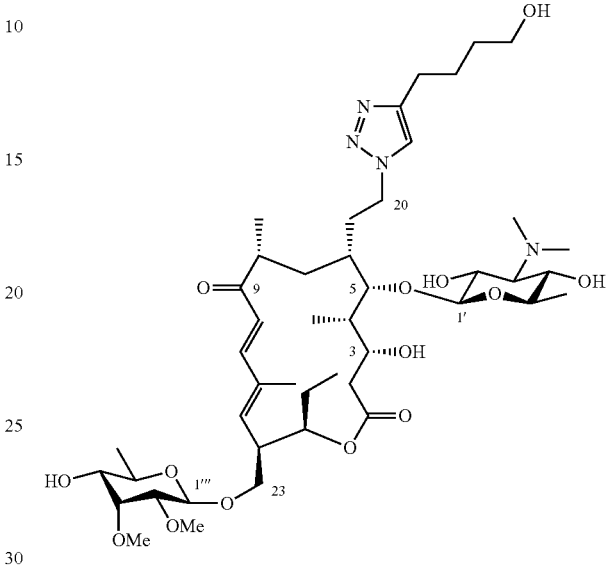

Yield: 97%

HRFABMS: calcd. for $C_{45}H_{77}O_{14}N_4$: 897.5436 [M+H]. found m/z: 897.5445 [M+H]$^+$.

IR (KBr)vcm$^{-1}$: 3433 (—OH), 2933 (C—H), 1722 (C=O).

$^1$H NMR (270 MHz, CDCl$_3$) δ (ppm): 7.37 (s, 1H, H-20-triazole-4-butanol), 7.12 (d, J=15.5 Hz, 1H, H-11), 6.16 (d, J=15.5 Hz, 1H, H-10), 5.88 (d, J=10.6 Hz, 1H, H-13), 4.91 (br. dt, J=10.5 Hz, 1H, H-15), 4.53 (d, J=7.9 Hz, 1H, H-1'''), 4.40 (m, 2H, H-20), 4.32 (d, J=7.3 Hz, 1H, H-1'), 3.98 (dd, J=9.4, 3.5 Hz, 1H, H-23), 3.78 (d, J=11.2 Hz, 1H, H-5), 3.73 (t, J=3.1 Hz, 1H, H-3'''), 3.68 (t, J=6.4 Hz, 2H, H-20-triazole-4-butanol), 3.58 (s, 3H, 3'''-OCH$_3$), 3.56-3.39 (m, 6H, H-3, H-23, H-2', H-5'''), 3.44 (s, 3H, 2'''-OCH$_3$), 3.30 (m, 1H, H-5'), 3.15 (dd, J=9.6, 3.0 Hz, 1H, H-4'''), 3.08 (t, J=9.4 Hz, 1H, H-4'), 3.00 (dd, J=7.9, 2.6 Hz, 1H, H-2'''), 2.99 (m, 3H, H-14, H-20-triazole-4-butanol), 2.77 (t, J=7.6 Hz, 4H, H-20-triazole-4-butanol), 2.60 (m, 1H, H-8), 2.48 (s, 6H, 3'-N(CH$_3$)$_2$), 2.44-2.35 (m, 2H, H-2, H-3'), 2.19-2.01 (m, 2H, H-6, H-19), 1.86-1.81 (m, 2H, H-2, H-16), 1.71 (s, 3H, H-22), 1.68-1.54 (m, 4H, H-4, H-7, H-16), 1.23 (d, J=6.3 Hz, 3H, H-6'), 1.22 (t, J=5.3 Hz, 3H, H-6'''), 1.14 (d, J=6.6 Hz, 3H, H-21), 1.00 (d, J=6.6 Hz, 3H, H-18), 0.89 (t, J=7.2 Hz, 3H, H-17).

$^{13}$C NMR (67.5 MHz, CDCl$_3$) δ (ppm): 203.2 (C-9), 173.5 (C-1), 147.9 (C-11), 147.8 (C-20-triazole-4-butanol), 142.7 (C-13), 134.4 (C-12), 120.3 (C-20-triazole-4-butanol), 18.0 (C-10), 103.5 (C-1'), 100.9 (C-1'''), 81.5 (C-2'''), 79.7 (C-5), 77.5 (C-3''), 74.8 (C-15), 73.1 (C-5'), 72.6 (C-4'''), 70.7 (4C, C-2', C-3', C-4', C-5'''), 69.0 (C-23), 66.0 (C-3), 61.9 (C-20-triazole-4-butanol), 61.6 (C-8'''), 59.4 (C-7'''), 47.6 (C-20), 44.9 (C-14), 44.9 (C-8), 41.5 (2C, C-7', 8'), 40.6 (C-4), 39.3 (C-2), 33.8 (C-7), 33.0 (C-6), 32.0 (C-20-triazole-4-butanol), 28.2 (C-19), 25.6 (C-20-triazole-4-butanol), 25.1 (C-20-triazole-4-butanol), 25.0 (C-16), 17.5 (2C, C-6', C-6'''), 17.3 (C-21), 12.7 (C-22), 9.5 (C-17), 9.0 (C-18).

20-(4-(methanol)-1H-1,2,3-triazol-1-yl)-20-deoxodesmycosin (YT37)

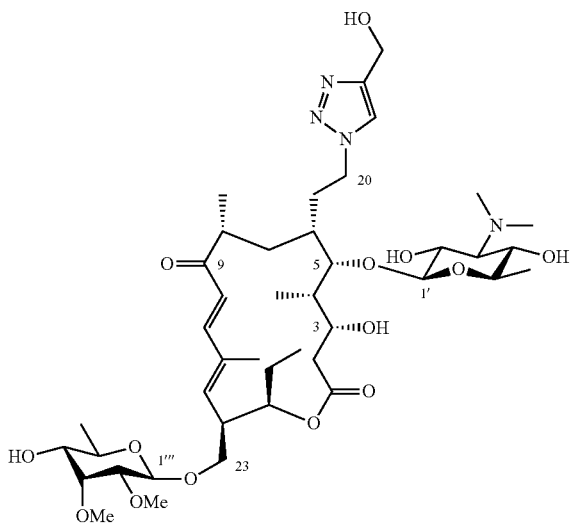

Yield: 100%

HRFABMS: calcd. for $C_{42}H_{71}O_{14}N_4$: 855.4967 [M+H]. found m/z: 855.4972 [M+H]$^+$.

IR (KBr)vcm$^{-1}$: 3433 (—OH), 2933 (C—H), 1722 (C=O).

$^1$H NMR (270 MHz, CDCl$_3$) δ (ppm): 7.60 (s, 1H, H-20-triazole-methanol), 7.16 (d, J=15.2 Hz, 1H, H-11), 6.12 (d, J=15.5 Hz, 1H, H-10), 5.89 (d, J=10.6 Hz, 1H, H-13), 4.89 (br. dt, J=9.6 Hz, 1H, H-15), 4.77 (d, J=7.9 Hz, 1H, H-20-triazole-methanol), 4.53 (d, J=7.6 Hz, 2H, H-20, H-1''''), 4.32 (d, J=7.3 Hz, 2H, H-20, H-1'), 3.94 (dd, J=9.6, 4.0 Hz, 1H, H-23), 3.72-3.69 (m, 2H, H-5, H-3'''), 3.57 (s, 3H, 3'''-OCH$_3$), 3.52-3.38 (m, 6H, H-3, H-23, H-2', H-5'''), 3.43 (s, 3H, 2'''-OCH$_3$), 3.31 (m, 1H, H-5'), 3.15 (d, J=8.9 Hz, 1H, H-4''), 3.06 (t, J=9.4 Hz, 1H, H-4'), 2.99 (dd, J=7.7, 2.8 Hz, 1H, H-2''), 2.89 (m, 1H, H-14), 2.55 (m, 1H, H-8), 2.46 (s, 6H, 3'-N(CH$_3$)$_2$), 2.39 (d, J=5.6 Hz, 1H, H-2), 2.35 (t, J=10.2 Hz, 1H, H-3'), 2.18 (m, 1H, H-19), 1.96 (m, 1H, H-6), 1.81-1.75 (m, 2H, H-2, H-16), 1.68 (s, 3H, H-22), 1.45-1.55 (m, 4H, H-4, H-7, H-16), 1.23 (d, J=3.3 Hz, 3H, H-6'), 1.21 (d, J=3.6 Hz, 3H, H-6'''), 1.13 (d, J=6.9 Hz, 3H, H-21), 0.90 (d, J=6.6 Hz, 3H, H-18), 0.86 (t, J=7.1 Hz, 3H, H-17).

$^{13}$C NMR (67.5 MHz, CDCl$_3$) δ (ppm): 203.6 (C-9), 173.7 (C-1), 148.3 (C-11), 148.2 (C-20-triazole-methanol), 143.3 (C-13), 134.4 (C-12), 121.8 (C-20-triazole-methanol), 117.5 (C-10), 103.5 (C-1'), 100.9 (C-1'''), 81.7 (C-2''), 79.7 (C-5), 77.5 (C-3''), 75.2 (C-15), 73.2 (C-5'), 72.6 (C-4''), 70.9 (4C, C-2', C-3', C-4', C-5'''), 70.0 (C-23), 66.0 (C-3), 61.6 (C-8'''), 59.5 (C-7'''), 56.3 (C-20-triazole-methanol), 47.6 (C-20), 45.1 (C-14), 45.0 (C-8), 41.6 (2C, C-7', 8'), 40.6 (C-4), 39.8 (C-2), 32.8 (C-7), 32.7 (C-6), 28.1 (C-19), 25.3 (C-16), 17.8 (2C, C-6', C-6'''), 17.7 (C-21), 12.8 (C-22), 9.6 (C-17), 9.1 (C-18).

Preparation of 23-triazole-23-deoxo-5-β-mycaminosyltylonolides (1) Preparation of 5-O-mycaminosyltylonolide (YT106)

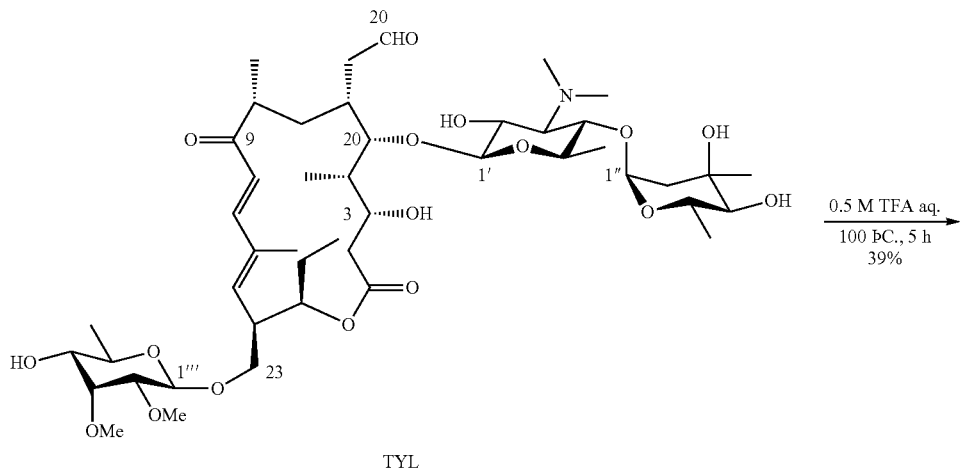

TYL

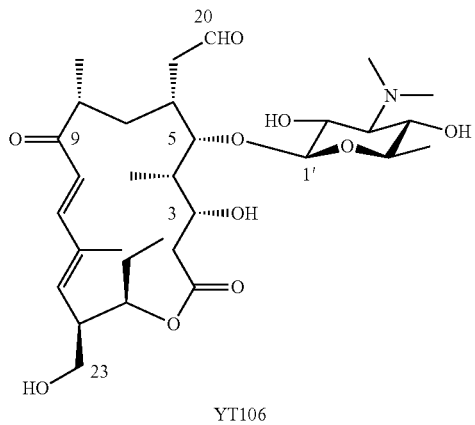

YT106

Tylosin (9.16 g, 10.0 mmol) was dissolved to 0.5 M TFA solution (300 mL) and then the mixture was stirred for 5 hours at 100° C. After confirming complete consumption of the starting material, the reaction mixture was neutralized by adding NaHCO$_3$ sat. aq., extracted with CHCl$_3$ and dried over Na$_2$SO$_4$. The solvent was removed under reduced-pressure. The resulting products were purified by flash column chromatography to obtain YT106 (Yield: 39%).

Rf: 0.3 (CHCl$_3$:MeOH:NH$_4$OH=5:1:0.005).

HRFABMS: calcd. for C$_{31}$H$_{52}$O$_{10}$N: 598.3591 [M+H]. found m/z: 598.3610 [M+H]$^+$.

$^1$H NMR (270 MHz, CDCl$_3$) δ (ppm): 9.69 (s, 1H, H-20), 7.32 (d, J=15.5 Hz, 1H, H-11), 6.29 (d, J=15.5 Hz, 1H, H-10), 5.88 (d, J=10.2 Hz, 1H, H-13), 4.96 (br. dt, J=9.6 Hz, 1H, H-15), 4.25 (d, J=7.2 Hz, 1H, H-1'), 3.84 (d, J=10.6 Hz, 1H, H-3), 3.73 (d, J=10.3 Hz, 1H, H-23), 3.48 (dd, J=10.0, 9.0 Hz, 1H, H-2'), 3.27 (m, 1H, H-5'), 3.27 (t, J=7.4 Hz, 1H, H-4'), 3.09-3.02 (m, 3H, H-14, H-19), 2.55 (m, 1H, H-8), 2.50 (s, 6H, 3'-N(CH$_3$)$_2$), 2.40-2.32 (m, 4H, H-2, H-19, H-3'), 2.13 (m, 1H, H-6), 1.95 (d, J=16.9 Hz, 1H, H-2), 1.87 (m, 1H, H-16), 1.83 (s, 3H, H-22), 1.68-1.48 (m, 4H, H-4, H-7, H-16), 1.26 (d, J=6.0 Hz, 3H, H-6'), 1.22 (d, J=6.9 Hz, 3H, H-21), 1.01 (d, J=6.6 Hz, 3H, H-18), 0.95 (t, J=7.2 Hz, 3H, H-17).

$^{13}$C NMR (67.5 MHz, CDCl$_3$) δ (ppm): 203.8 (C-9), 203.2 (C-20), 173.7 (C-1), 148.2 (C-11), 142.3 (C-13), 135.3 (C-12), 118.5 (C-10), 103.0 (C-1'), 81.0 (C-5), 74.9 (C-15), 73.0 (C-5'), 70.7 (C-4'), 70.6 (C-2'), 69.9 (C-3'), 67.4 (C-3), 61.9 (C-23), 46.9 (C-14), 44.6 (C-8), 43.5 (C-19), 41.5 (2C, C-7', 8'), 40.3 (C-4), 39.3 (C-2), 32.8 (C-7), 31.9 (C-6), 25.2 (C-16), 17.6 (C-6'), 17.2 (C-21), 12.9 (C-22), 9.5 (C-17), 8.8 (C-18).

(2) Preparation of 23-azido-23-deoxo-5-O-mycaminosyltylonolide (YT107)

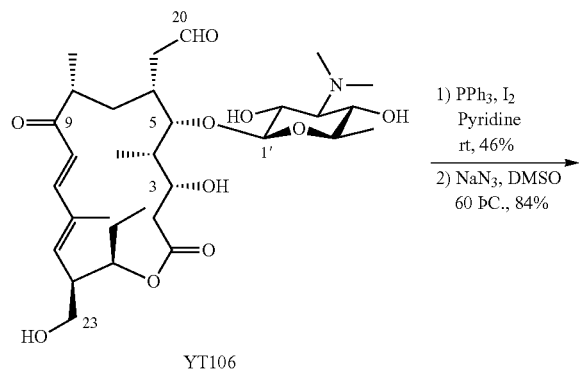

YT106

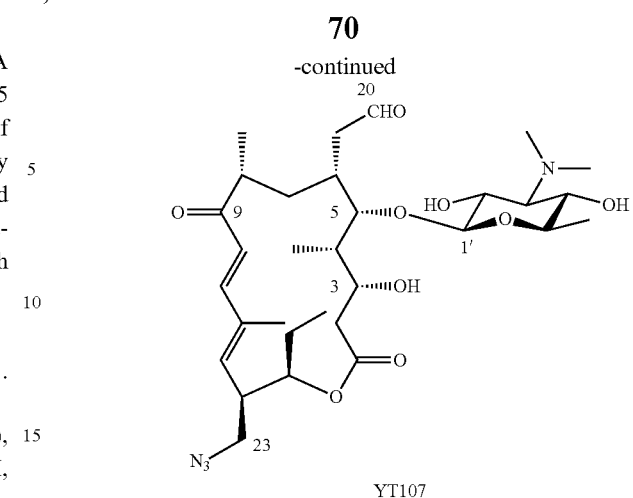

YT107

To a solution of PPh$_3$ (787 mg, 3.0 mmol) and I$_2$ (381 mg, 3.0 mmol) in pyridine (4.0 mL) was added YT106 (300 mg, 0.50 mmol) under N$_2$ atmosphere and then stirred for 4 hours at rt. After confirming complete consumption of the starting material, the reaction mixture was diluted with CHCl$_3$. The organic layer was washed with Na$_2$S$_2$O$_3$ sat. aq. and dried over Na$_2$SO$_4$. The solvent was then removed under reduced pressure. The resulting products were purified by flash column chromatography to obtain 23-I-23-deoxo-5-β-myca-minosyltylonolide (Yield: 46%).

To a solution of 23-I-23-deoxo-5-O-mycaminosyltylono-lide (155 mg, 0.22 mmol) in DMSO (2.0 mL) was added NaN$_3$ (50 mg, 0.77 mmol) and then the mixture was stirred for 90 minutes at 60° C. After confirming complete consumption of the starting material by mass spectrometry, the reaction mixture was diluted with CHCl$_3$. The organic layer was washed with water and dried over Na$_2$SO$_4$. The solvent was removed under reduced pressure. The resulting products were purified by flash column chromatography to obtain YT107 (Yield: 84%).

Rf: 0.5 (CHCl$_3$:MeOH:NH$_4$OH=5:1:0.005).

HRFABMS: calcd. for C$_{31}$H$_{51}$O$_9$N$_4$: 623.3656 [M+H]. found m/z: 623.3603 [M+H]$^+$.

$^1$H NMR (270 MHz, CDCl$_3$) δ (ppm): 9.69 (s, 1H, H-20), 7.31 (d, J=15.5 Hz, 1H, H-11), 6.31 (d, J=15.5 Hz, 1H, H-10), 5.76 (d, J=10.6 Hz, 1H, H-13), 4.90 (dt, J=9.6, 2.8 Hz, 1H, H-15), 4.25 (d, J=7.6 Hz, 1H, H-1'), 3.84 (d, J=10.9 Hz, 1H, H-3), 3.72 (d, J=8.9 Hz, 1H, H-5), 3.52-3.37 (m, 3H, H-23, H-2'), 3.27 (m, 1H, H-5'), 3.06 (t, J=9.4 Hz, 1H, H-4'), 2.97-2.85 (m, 3H, H-14, H-19), 2.55 (m, 1H, H-8), 2.62 (s, 6H, 3'-N(CH$_3$)$_2$), 2.70-2.33 (m, 4H, H-2, H-19, H-3'), 2.13 (m, 1H, H-6), 1.94 (d, J=16.0 Hz, 1H, H-2), 1.83 (s, 3H, H-22), 1.80 (m, 1H, H-16), 1.79-1.49 (m, 4H, H-4, H-7, H-16), 1.26 (d, J=6.6 Hz, 3H, H-6'), 1.22 (d, J=6.6 Hz, 3H, H-21), 1.01 (d, J=6.6 Hz, 3H, H-18), 0.95 (t, J=7.2 Hz, 3H, H-17).

$^{13}$C NMR (67.5 MHz, CDCl$_3$) δ (ppm): 203.2 (C-9), 203.1 (C-20), 173.5 (C-1), 147.3 (C-11), 142.3 (C-13), 135.9 (C-12), 118.5 (C-10), 104.0 (C-1'), 82.0 (C-5), 74.6 (C-15), 73.1 (C-5'), 70.7 (C-4'), 70.6 (C-2'), 70.0 (C-3'), 68.0 (C-3), 51.0 (C-23), 46.0 (C-14), 44.3 (C-8), 43.5 (C-19), 41.5 (2C, C-7', 8'), 40.6 (C-4), 39.3 (C-2), 32.8 (C-7), 31.9 (C-6), 25.1 (C-16), 17.6 (C-6'), 17.2 (C-21), 12.9 (C-22), 9.4 (C-17), 8.8 (C-18).

(3) Preparation of 23-triazole-23-deoxy-5-O-mycaminosyltylonolides

To a solution of YT107 (0.24 g, 0.30 mmol) in CH$_3$CN or MeOH (3.0 mL) were added CuI (2.9 mg, 0.015 mmol), TBTA (1.6 mg, 3.0 μmol) and a suitable acetylene compound, and then the mixture was stirred at rt until the reaction was completed. After completion, the reaction mixture was diluted with CHCl$_3$, and washed with 10% NH$_3$ aq. After removing CuI, the filtrate was washed with brine. The organic layer was dried over Na$_2$SO$_4$ and concentrated. The resulting products were purified by flash column chromatography to obtain the following triazole compounds:

23-(4-phenyl-1H-1,2,3-triazol-1-yl)-23-Deoxy-5-O-mycaminosyltylonolide (YT101)

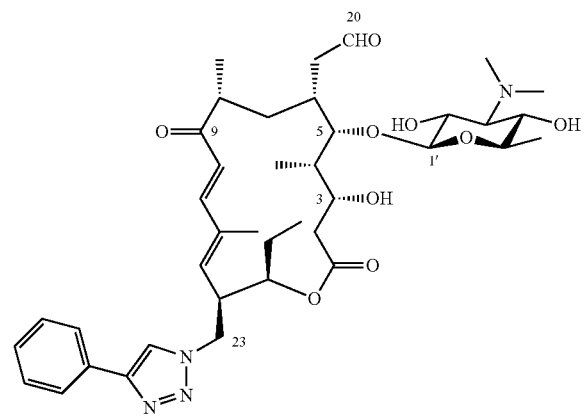

YT101

Yield: 64%
Rf: 0.5 (CHCl$_3$:MeOH:NH$_4$OH=8:1:0.008).
HRFABMS: calcd. for C$_{39}$H$_{57}$O$_9$N$_4$: 725.4126 [M+H]. found m/z: 725.4158 [M+H]$^+$.
$^1$H NMR (270 MHz, CDCl$_3$) δ (ppm): 9.68 (s, 1H, H-20), 7.80 (d, J=9.6 Hz, 3H, H-triazole-phenyl), 7.66 (s, 1H, H-triazole-phenyl), 7.40 (m, 2H, H-triazole-phenyl), 7.19 (d, J=15.5 Hz, 1H, H-11), 6.23 (d, J=15.5 Hz, 1H, H-10), 5.68 (d, J=10.6 Hz, 1H, H-13), 4.94 (br. dt, J=9.6, 1H, H-15), 4.66 (dd, J=13.5, 3.6 Hz, 1H, H-23), 4.32 (dd, J=13.5, 3.6 Hz, 1H, H-23), 4.23 (d, J=7.3 Hz, 1H, H-1'), 3.83 (d, J=10.5 Hz, 1H, H-3), 3.69 (d, J=7.9 Hz, 1H, H-5), 3.43 (m, 1H, H-2'), 3.25 (m, 1H, H-5'), 3.04 (t, J=9.7 Hz, 1H, H-4'), 2.90 (m, 1H, H-19), 2.55 (m, 1H, H-8), 2.49 (s, 6H, 3'-N(CH$_3$)$_2$), 2.46-2.21 (m, 2H, H-14, H-3'), 2.10 (m, 1H, H-6), 1.93 (d, J=7.2 Hz, 1H, H-2), 1.77 (m, 1H, H-16), 1.66 (s, 3H, H-22), 1.60-1.40 (m, 4H, H-4, H-7, H-16), 1.24 (d, J=5.9 Hz, 3H, H-6'), 1.16 (d, J=6.6 Hz, 3H, H-21), 0.99 (d, J=6.6 Hz, 3H, H-18), 0.95 (t, J=7.2 Hz, 3H, H-17).
$^{13}$C NMR (67.5 MHz, CDCl$_3$) δ (ppm): 203.2 (C-9), 203.0 (C-20), 173.6 (C-1), 147.6 (C-23-triazole-phenyl), 146.9 (C-11), 138.4 (C-13), 137.8 (C-12), 128.9 (2C, C-23-triazole-phenyl), 128.4 (C-23-triazole-phenyl), 125.8 (3C, C-23-triazole-phenyl), 120.1 (C-23-triazole-phenyl), 118.5 (C-10), 104.0 (C-1'), 81.0 (C-5), 74.5 (C-15), 73.4 (C-5'), 70.9 (C-4'), 70.8 (C-2'), 70.1 (C-3'), 68.0 (C-3), 51.1 (C-23), 46.0 (C-14), 44.3 (C-8), 43.8 (C-19), 41.8 (2C, C-7', 8'), 40.2 (C-4), 39.5 (C-2), 32.8 (C-7), 31.9 (C-6), 25.5 (C-16), 18.0 (C-6'), 17.4 (C-21), 13.0 (C-22), 9.7 (C-17), 9.1 (C-18).

23-(4-butyl-1H-1,2,3-triazol-1-yl)-23-Deoxo-5-O-mycaminosyltylonolide (YT102)

YT102

Yield: 77%
Rf: 0.5 (CHCl$_3$:MeOH:NH$_4$OH=8:1:0.008).
HRFABMS: calcd. for C$_{37}$H$_{61}$O$_9$N$_4$: 705.4439 [M+H]. found m/z: 705.4457 [M+H]$^+$.
$^1$H NMR (270 MHz, CDCl$_3$) δ (ppm): 9.70 (s, 1H, H-20), 7.21 (d, J=9.6 Hz, 1H, H-11), 7.16 (s, 1H, H-triazole-butyl), 6.25 (d, J=15.5 Hz, 1H, H-10), 5.63 (d, J=10.2 Hz, 1H, H-13), 4.91 (br. dt, J=9.6, 1H, H-15), 4.59 (dd, J=13.9, 3.6 Hz, 1H, H-23), 4.24 (d, J=7.6 Hz, 1H, H-1'), 4.19 (d, J=9.9 Hz, 1H, H-23), 3.83 (d, J=10.2 Hz, 1H, H-3), 3.71 (d, J=9.2 Hz, 1H, H-5), 3.49 (dd, J=9.5, 7.2 Hz, 1H, H-2'), 3.25 (m, 1H, H-5'), 3.05 (t, J=9.6 Hz, 1H, H-4'), 2.96 (m, 1H, H-19), 2.70-2.53 (m, 2H, H-8, H-19), 2.50 (s, 6H, 3'-N(CH$_3$)$_2$), 2.40-2.17 (m, 3H, H-8, H-14, H-3'), 2.10 (m, 1H, H-6), 1.93 (d, J=16.5 Hz, 1H, H-2), 1.86-1.39 (m, 8H, H-4, H-7, H-16, H-22), 1.36-1.10 (m, 12H, H-21, H-6', H-triazole-butyl), 1.02-0.97 (m, 6H, H-18, H-triazole-butyl), 0.90 (t, J=7.2 Hz, 3H, H-17).
$^{13}$C NMR (67.5 MHz, CDCl$_3$) δ (ppm): 203.1 (C-9), 203.0 (C-20), 173.6 (C-1), 146.6 (C-11), 148.6 (C-23-triazole-butyl), 138.0 (C-13), 137.6 (C-12), 121.3 (C-23-triazole-butyl), 118.5 (C-10), 104.0 (C-1'), 81.0 (C-5), 74.2 (C-15), 73.2 (C-5'), 70.7 (C-4'), 70.6 (C-2'), 70.2 (C-3'), 68.0 (C-3), 50.8 (C-23), 46.0 (C-14), 44.3 (C-8), 43.8 (C-19), 41.8 (2C, C-7', 8'), 40.2 (C-4), 39.5 (C-2), 32.8 (C-7), 31.9 (C-6), 31.6 (C-23-triazole-butyl), 31.0 (C-23-triazole-butyl), 25.3 (C-16), 22.3 (C-23-triazole-butyl), 17.9 (C-6'), 17.4 (C-21), 13.9 (C-23-triazole-butyl), 12.9 (C-22), 9.6 (C-17), 9.0 (C-18).

23-(4-(3-quinoline-3-yl)-1H-1,2,3-triazol-1-yl)-23-Deoxo-5-O-mycaminosyltylonolide (YT103)

23-(4-biphenyl-1H-1,2,3-triazol-1-yl)-23-Deoxy-5-O-mycaminosyltylonolide (YT104)

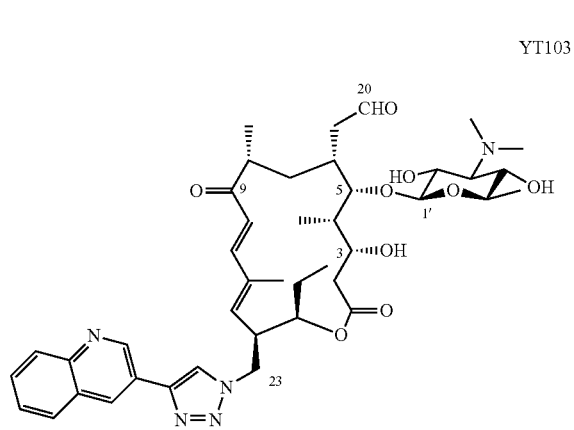

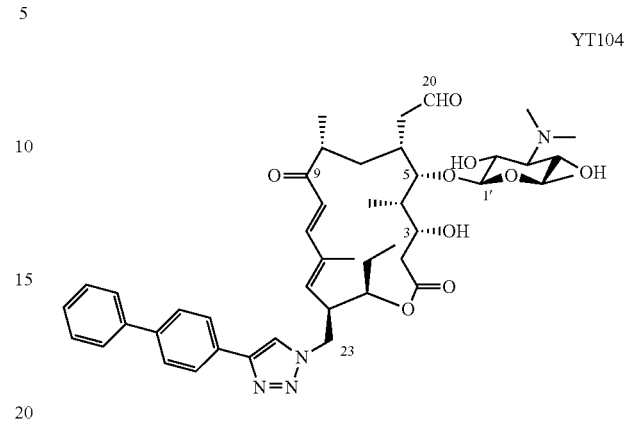

Yield: 100%

Rf: 0.4 (CHCl$_3$:MeOH:NH$_4$OH=8:1:0.008).

HRFABMS: calcd. for C$_{42}$H$_{58}$O$_9$N$_5$: 726.4235 [M+H]. found m/z: 726.4196 [M+H]$^+$.

$^1$H NMR (270 MHz, CDCl$_3$) δ (ppm): 9.67 (s, 1H, H-20), 9.29 (d, J=2.0 Hz, 1H, H-triazole-quinoline), 8.59 (d, J=2.0 Hz, 1H, H-triazole-quinoline), 8.09 (d, J=7.6 Hz, 1H, H-triazole-quinoline), 7.92 (s, 1H, H-triazole-quinoline), 7.86 (d, J=7.9 Hz, 1H, H-triazole-quinoline), 7.70 (t, J=6.9 Hz, 1H, H-triazole-quinoline), 7.55 (d, J=7.6 Hz, 1H, H-triazole-quinoline), 7.19 (d, J=15.5 Hz, 1H, H-11), 6.24 (d, J=15.5 Hz, 1H, H-10), 5.71 (d, J=10.6 Hz, 1H, H-13), 4.97 (br. dt, J=9.6, 1H, H-15), 4.66 (dd, J=13.5, 3.6 Hz, 1H, H-23), 4.32 (dd, J=13.5, 3.6 Hz, 1H, H-23), 4.23 (d, J=7.2 Hz, 1H, H-1'), 3.83 (d, J=10.2 Hz, 1H, H-3), 3.68 (d, J=7.9 Hz, 1H, H-5), 3.44 (m, 1H, H-2'), 3.25 (m, 1H, H-5'), 3.04 (t, J=9.4 Hz, 1H, H-4'), 2.95 (m, 1H, H-19), 2.55 (m, 1H, H-8), 2.48 (s, 6H, 3'-N(CH$_3$)$_2$), 2.46-2.31 (m, 2H, H-14, H-3'), 2.10 (m, 1H, H-6), 1.93 (d, J=6.8 Hz, 1H, H-2), 1.76 (m, 1H, H-16), 1.67 (s, 3H, H-22), 1.58-1.41 (m, 4H, H-4, H-7, H-16), 1.23 (d, J=5.9 Hz, 3H, H-6'), 1.13 (d, J=6.6 Hz, 3H, H-21), 1.04-0.99 (m, 6H, H-17, H-18).

$^{13}$C NMR (67.5 MHz, CDCl$_3$) δ (ppm): 203.2 (C-9), 203.0 (C-20), 173.8 (C-1), 148.4 (C-23-triazole-quinoline), 147.8 (C-23-triazole-quinoline), 146.8 (C-11), 145.0 (C-23-triazole-quinoline), 138.4 (C-13), 137.8 (C-12), 132.2 (C-23-triazole-quinoline), 129.8 (C-23-triazole-quinoline), 129.4 (C-23-triazole-quinoline), 128.3 (C-23-triazole-quinoline), 128.0 (C-23-triazole-quinoline), 127.3 (C-23-triazole-quinoline), 123.6 (C-23-triazole-quinoline), 120.8 (C-23-triazole-quinoline), 118.5 (C-10), 104.0 (C-1'), 81.0 (C-5), 74.5 (C-15), 73.4 (C-5'), 70.9 (C-4'), 70.8 (C-2'), 70.2 (C-3'), 68.0 (C-3), 51.3 (C-23), 46.0 (C-14), 44.7 (C-8), 43.8 (C-19), 41.8 (2C, C-7', 8'), 40.2 (C-4), 39.6 (C-2), 32.8 (C-7), 31.9 (C-6), 25.6 (C-16), 18.0 (C-6'), 17.4 (C-21), 13.0 (C-22), 9.7 (C-17), 9.1 (C-18).

Yield: 100%

Rf: 0.4 (CHCl$_3$:MeOH:NH$_4$OH=8:1:0.008).

HRFABMS: calcd. for C$_{45}$H$_{61}$O$_9$N$_4$: 801.4439 [M+H]. found m/z: 801.4435 [M+H]$^+$.

$^1$H NMR (270 MHz, CDCl$_3$) δ (ppm): 9.67 (s, 1H, H-20), 7.86 (d, J=6.9 Hz, 2H, H-triazole-biphenyl), 7.71 (s, 1H, H-triazole-biphenyl), 7.63 (t, J=8.3 Hz, 4H, H-triazole-biphenyl), 7.41 (m, 3H, H-triazole-biphenyl), 7.20 (d, J=15.5 Hz, 1H, H-11), 6.24 (d, J=15.5 Hz, 1H, H-10), 5.69 (d, J=10.5 Hz, 1H, H-13), 4.96 (br. dt, J=9.6, 1H, H-15), 4.66 (dd, J=13.5, 3.6 Hz, 1H, H-23), 4.33 (dd, J=13.5, 3.6 Hz, 1H, H-23), 4.23 (d, J=7.5 Hz, 1H, H-1'), 3.84 (d, J=10.2 Hz, 1H, H-3), 3.69 (d, J=8.9 Hz, 1H, H-5), 3.46 (m, 1H, H-2'), 3.25 (m, 1H, H-5'), 3.04 (t, J=9.6 Hz, 1H, H-4'), 2.95 (m, 1H, H-19), 2.56 (m, 1H, H-8), 2.49 (s, 6H, 3'-N(CH$_3$)$_2$), 2.39-2.31 (m, 2H, H-14, H-3'), 2.10 (m, 1H, H-6), 1.95 (d, J=7.1 Hz, 1H, H-2), 1.78 (m, 1H, H-16), 1.66 (s, 3H, H-22), 1.59-1.42 (m, 4H, H-4, H-7, H-16), 1.25 (d, J=5.9 Hz, 3H, H-6'), 1.16 (d, J=6.9 Hz, 3H, H-21), 1.04-0.99 (m, 6H, H-17, H-18).

$^{13}$C NMR (67.5 MHz, CDCl$_3$) δ (ppm): 203.2 (C-9), 203.0 (C-20), 173.8 (C-1), 147.6 (C-23-triazole-biphenyl), 146.9 (C-11), 141.2 (C-23-triazole-biphenyl), 140.6 (C-23-triazole-biphenyl), 138.4 (C-13), 137.8 (C-12), 129.0 (C-23-triazole-biphenyl), 128.9 (3C, C-23-triazole-biphenyl), 127.6 (2C, C-23-triazole-biphenyl), 127.1 (2C, C-23-triazole-biphenyl), 126.2 (2C, C-23-triazole-biphenyl), 120.2 (C-23-triazole-biphenyl), 118.5 (C-10), 104.0 (C-1'), 81.0 (C-5), 74.5 (C-15), 73.4 (C-5'), 70.9 (C-4'), 70.8 (C-2'), 70.1 (C-3'), 68.0 (C-3), 51.1 (C-23), 46.0 (C-14), 44.3 (C-8), 43.8 (C-19), 41.8 (2C, C-7', 8'), 40.2 (C-4), 39.5 (C-2), 32.8 (C-7), 31.9 (C-6), 25.5 (C-16), 18.0 (C-6'), 17.4 (C-21), 13.0 (C-22), 9.7 (C-17), 9.1 (C-18).

23-(4-(pyridine-3-yl)-1H-1,2,3-triazol-1-yl)-23-Deoxo-5-O-mycaminosyltylonolide (YT109)

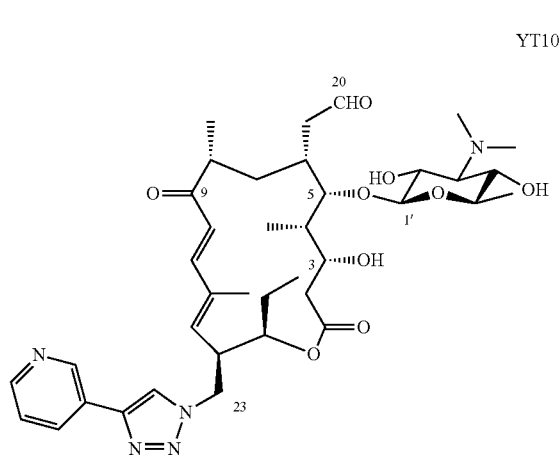

23-(4-(methyl-1H-benzotriazolyl)-1H-1,2,3-triazol-1-yl) 23-deoxo-5-O-mycaminosyltylonolide (YT109)

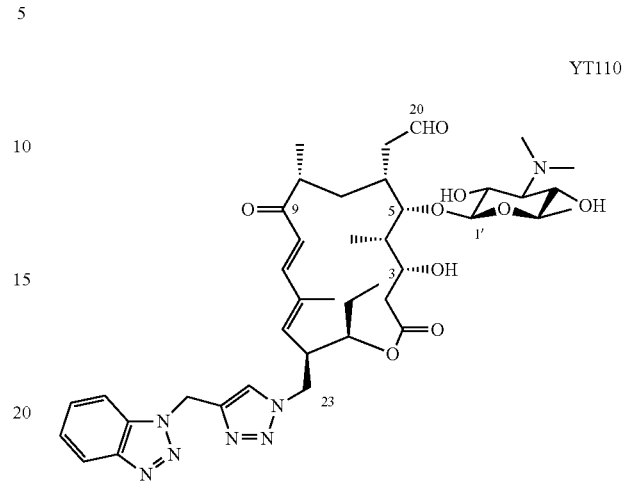

Yield: 94%

Rf: 0.5 (CHCl$_3$:MeOH:NH$_4$OH=8:1:0.008).

MS (ESI+): calcd. for C$_{38}$H$_{56}$O$_9$N$_5$: 726.4097 [M+H]. found m/z: 726.4078 [M+H]$^+$.

$^1$H NMR (270 MHz, CDCl$_3$) δ (ppm): 9.68 (s, 1H, H-20), 8.97 (s, 1H, H-triazole-3-pyridine), 8.56 (s, 1H, H-triazole-3-pyridine), 8.14 (d, J=7.9 Hz, 1H, H-triazole-3-pyridine), 7.79 (s, 1H, H-triazole-3-pyridine), 7.35 (dd, J=7.6, 4.7 Hz, 1H, H-triazole-3-pyridine), 7.19 (d, J=15.5 Hz, 1H, H-11), 6.25 (d, J=15.5 Hz, 1H, H-10), 5.68 (d, J=10.5 Hz, 1H, H-13), 4.96 (br. dt, J=9.6, 1H, H-15), 4.68 (dd, J=13.5, 3.8 Hz, 1H, H-23), 4.37 (dd, J=12.6, 9.6 Hz, 1H, H-23), 4.23 (d, J=7.6 Hz, 1H, H-1'), 3.83 (d, J=10.2 Hz, 1H, H-3), 3.68 (d, J=8.9 Hz, 1H, H-5), 3.50-3.39 (m, 2H, H-14, H-2'), 3.25 (m, 1H, H-5'), 3.04 (t, J=9.6 Hz, 1H, H-4'), 2.95 (m, 1H, H-19), 2.56 (m, 1H, H-8), 2.49 (s, 6H, 3'-N(CH$_3$)$_2$), 2.43-2.31 (m, 2H, H-9, H-3'), 2.10 (m, 1H, H-6), 1.93 (d, J=6.8 Hz, 1H, H-2), 1.75 (m, 1H, H-16), 1.67 (s, 3H, H-22), 1.60-1.45 (m, 4H, H-4, H-7, H-16), 1.24 (d, J=5.9 Hz, 3H, H-6'), 1.15 (d, J=6.9 Hz, 3H, H-21), 1.04-0.99 (m, 6H, H-17, H-18).

$^{13}$C NMR (67.5 MHz, CDCl$_3$) δ (ppm): 203.2 (C-9), 203.0 (C-20), 173.6 (C-1), 149.4 (C-23-triazole-3-pyridine), 147.1 (C-23-triazole-3-pyridine), 146.8 (C-11), 144.8 (C-23-triazole-3-pyridine), 138.4 (C-13), 137.9 (C-12), 133.2 (2C, C-23-triazole-3-pyridine), 123.9 (C-23-triazole-3-pyridine), 120.6 (C-23-triazole-3-pyridine), 118.5 (C-10), 104.0 (C-1'), 81.0 (C-5), 74.4 (C-15), 73.4 (C-5'), 70.9 (C-4'), 70.8 (C-2'), 70.2 (C-3'), 68.0 (C-3), 51.2 (C-23), 45.9 (C-14), 44.3 (C-8), 43.8 (C-19), 41.8 (2C, C-7', 8'), 40.2 (C-4), 39.6 (C-2), 32.8 (C-7), 31.9 (C-6), 25.5 (C-16), 17.9 (C-6'), 17.4 (C-21), 13.0 (C-22), 9.7 (C-17), 9.1 (C-18).

Yield: 94%

Rf: 0.5 (CHCl$_3$:MeOH:NH$_4$OH=8:1:0.008).

MS (ESI+): calcd. for C$_{40}$H$_{58}$O$_9$N$_7$: 780.4325 [M+H]. found m/z: 780.4296 [M+H]$^+$.

$^1$H NMR (270 MHz, CDCl$_3$) δ (ppm): 9.67 (s, 1H, H-20), 7.99 (d, J=8.3 Hz, 1H, H-triazole-CH$_2$-benzotriazole), 7.59 (d, J=8.3 Hz, 1H, H-triazole-CH$_2$-benzotriazole), 7.46 (s, 1H, H-triazole-CH$_2$-benzotriazole), 7.42 (d, J=8.3 Hz, 1H, H-triazole-CH$_2$-benzotriazole), 7.32 (t, J=7.3 Hz, 1H, H-triazole-CH$_2$-benzotriazole), 7.05 (d, J=15.5 Hz, 1H, H-11), 6.16 (d, J=15.5 Hz, 1H, H-10), 5.80 (s, 2H, H-triazole-CH$_2$-benzotriazole), 5.52 (d, J=10.5 Hz, 1H, H-13), 4.89 (br. dt, J=9.6, 1H, H-15), 4.52 (dd, J=13.5, 3.6 Hz, 1H, H-23), 4.29 (d, J=9.9 Hz, 1H, H-23), 4.22 (d, J=7.3 Hz, 1H, H-1'), 3.79 (d, J=10.2 Hz, 1H, H-3), 3.68 (d, J=8.9 Hz, 1H, H-5), 3.46 (m, 1H, H-2'), 3.24 (m, 1H, H-5'), 3.05 (t, J=9.6 Hz, 1H, H-4'), 2.95 (m, 1H, H-19), 2.56 (m, 1H, H-8), 2.49 (s, 6H, 3'-N(CH$_3$)$_2$), 2.35 (m, 1H, H-3'), 2.10 (m, 1H, H-6), 1.88 (d, J=6.5 Hz, 1H, H-2), 1.75 (m, 1H, H-16), 1.81-1.57 (m, 4H, H-4, H-7, H-16), 1.49 (s, 3H, H-22), 1.25 (d, J=6.0 Hz, 3H, H-6'), 1.20 (d, J=6.9 Hz, 3H, H-21), 0.04-0.91 (m, 6H, H-17, H-18).

$^{13}$C NMR (67.5 MHz, CDCl$_3$) δ (ppm): 203.1 (C-9), 203.0 (C-20), 173.6 (C-1), 146.6 (C-11), 146.2 (C-23-triazole-CH$_2$-benzotriazole), 142.3 (C-23-triazole-CH$_2$-benzotriazole), 138.0 (C-13), 137.6 (C-12), 132.7 (C-23-triazole-CH$_2$-benzotriazole), 127.9 (2C, C-23-triazole-CH$_2$-benzotriazole), 124.3 (C-23-triazole-CH$_2$-benzotriazole), 123.4 (C-23-triazole-CH$_2$-benzotriazole), 120.0 (C-23-triazole-CH$_2$-benzotriazole), 118.5 (C-10), 110.0 (C-23-triazole-CH$_2$-benzotriazole), 104.0 (C-1'), 81.0 (C-5), 74.2 (C-15), 73.2 (C-5'), 70.7 (C-4'), 70.6 (C-2'), 70.2 (C-3'), 68.0 (C-3), 51.0 (C-23), 45.7 (C-14), 44.3 (C-8), 43.8 (C-19), 41.8 (2C, C-7', 8'), 40.2 (C-4), 39.5 (C-2), 32.8 (C-7), 31.9 (C-6), 25.5 (C-16), 17.9 (C-6'), 17.4 (C-21), 12.7 (C-22), 9.6 (C-17), 9.0 (C-18).

Preparation of 20-(4-phenyl-1H-1,2,3-triazol-1-yl)-20-deoxo-23-triazole-23-deoxy-5-O-mycaminosyltylonolides (1) Preparation of 20-(4-phenyl-1H-1,2,3-triazol-1-yl)-20-deoxo-5-O-mycaminosyltylonolide (YT112)

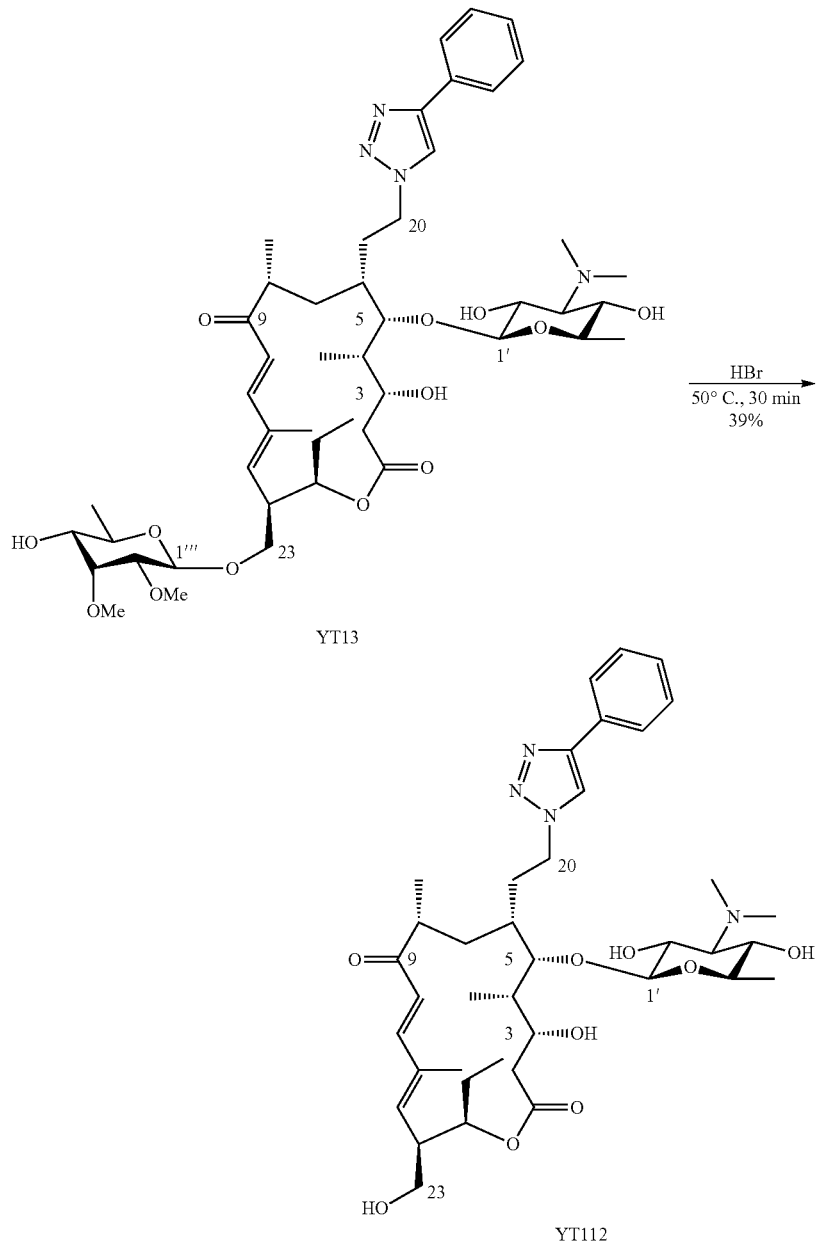

YT13 (0.5 g, 0.56 mmol) was dissolved in HBr (3.0 mL) and then the mixture was stirred for 30 minutes at 50° C. After confirming complete consumption of the starting material, the reaction mixture was neutralized by adding NaHCO$_3$ sat. aq., extracted with CHCl$_3$ and dried over Na$_2$SO$_4$. The solvent was removed under reduced pressure. The resulting products were purified by flash column chromatography to obtain YT112 (Yield: 39%).

Rf: 0.5 (CHCl$_3$:MeOH:NH$_4$OH=7:1:0.007).

HRFABMS: calcd. for $C_{39}H_{59}O_9N_4$: 724.4282 [M+H]. found m/z: 727.4307 [M+H]$^+$.

$^1$H NMR (270 MHz, CDCl$_3$) δ (ppm): 8.00 (d, J=7.3 Hz, 2H, H-20-triazole-phenyl), 7.90 (s, 1H, H-20-triazole-phenyl), 7.46 (t, J=7.6 Hz, 2H, H-20-triazole-phenyl), 7.32 (t, J=6.9 Hz, 1H, H-20-triazole-phenyl), 6.92 (d, J=15.5 Hz, 1H, H-11), 6.14 (d, J=15.2 Hz, 1H, H-10), 5.22 (d, J=9.6 Hz, 1H, H-13), 4.82 (br. dt, J=9.6 Hz, 1H, H-15), 4.50 (m, 2H, H-20), 4.35 (d, J=7.2 Hz, 1H, H-1'), 3.82 (d, J=10.2 Hz, 1H, H-3), 3.58-3.68 (m, 3H, H-5, H-14, H-23), 3.46 (m, 1H, H-2'), 3.34 (m, 1H, H-5'), 3.09 (t, J=9.6 Hz, 1H, H-4'), 2.72 (m, 1H, H-19), 2.56 (m, 1H, H-8), 2.49 (s, 6H, 3'-N(C$\underline{H}_3$)$_2$), 2.35 (m, 1H, H-3'), 2.10 (m, 1H, H-6), 1.88 (d, J=6.5 Hz, 1H, H-2), 1.75 (m, 1H, H-16), 1.81-1.57 (m, 4H, H-4, H-7, H-16), 1.49 (s, 3H, H-22), 1.25 (d, J=6.0 Hz, 3H, H-6'), 1.20 (d, J=6.9 Hz, 3H, H-21), 0.04-0.91 (m, 6H, H-17, H-18).

$^{13}$C NMR (67.5 MHz, CDCl$_3$) δ (ppm): 203.7 (C-9), 173.5 (C-1), 148.1 (C-11), 147.7 (C-20-<u>triazole</u>-phenyl), 140.7 (C-13), 136.0 (C-12), 131.0 (C-20-triazole-<u>phenyl</u>), 129.2 (C-20-triazole-<u>phenyl</u>), 128.9 (C-20-triazole-<u>phenyl</u>), 128.1 (C-20-<u>triazole</u>-phenyl), 126.1 (2C, C-20-triazole-phenyl), 119.9 (C-20-triazole-phenyl), 118.2 (C-10), 103.7 (C-1'), 80.1 (C-5), 75.1 (C-15), 73.4 (C-5'), 71.1 (C-4'), 71.0 (C-2'), 69.9 (C-3'), 66.9 (C-3), 62.7 (C-23), 48.0 (C-20), 47.9 (C-8), 47.0 (C-14), 45.0 (C-19), 41.8 (2C, C-7', 8'), 40.8 (C-4), 39.8 (C-2), 32.3 (C-7), 31.9 (C-6), 25.7 (C-16), 18.0 (C-6'), 17.7 (C-21), 13.4 (C-22), 9.8 (C-17), 9.4 (C-18).

(2) Preparation of 20-(4-phenyl-1H-1,2,3-triazol-1-yl)-20-deoxo-23-azido-23-deoxy-5-O-mycaminosyltylonolide (YT114)

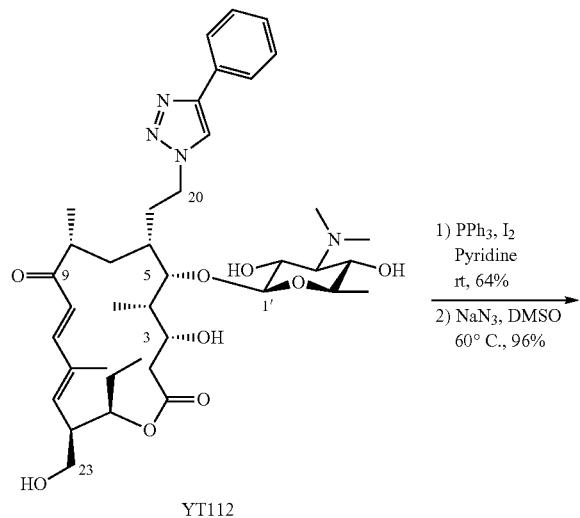

To a solution of PPh$_3$ (144 mg, 0.55 mmol) and I$_2$ (70 mg, 0.55 mmol) in pyridine (1.0 mL) was added YT112 (80 mg, 0.11 mmol) under N$_2$ atmosphere and then the mixture was stirred for 4 hours at rt. After confirming complete consumption of the starting material, the reaction mixture was diluted with CHCl$_3$. The organic layer was washed with Na$_2$S$_2$O$_3$ sat. aq. and dried over Na$_2$SO$_4$. The solvent was removed under reduced pressure. The resulting products were purified by flash column chromatography to obtain 20-(4-phenyl-1H-1,2,3-triazol-1-yl)-20-deoxo-23-I-23-deoxy-5-O-mycaminosyltylonolide (Yield: 64%).

To a solution of 20-(4-phenyl-1H-1,2,3-triazol-1-yl)-20-deoxo-23-I-23-deoxy-5-O-mycaminosyltylonolide (57 mg, 0.068 mmol) in DMSO (0.6 mL) was added NaN$_3$ (13 mg, 0.20 mmol) and then the mixture was stirred for 30 minutes at 60° C. After confirming complete consumption of the starting material by LC Mass, the reaction mixture was diluted with CHCl$_3$. The organic layer was washed with water and dried over Na$_2$SO$_4$. The solvent was removed under reduced pressure. The resulting products were purified by flash column chromatography to obtain YT114 (Yield: 96%).

Rf: 0.5 (CHCl$_3$:MeOH:NH$_4$OH=5:1:0.005).

HRFABMS: calcd. for C$_{39}$H$_{58}$O$_8$N$_7$: 752.4347 [M+H]. found m/z: 752.4354 [M+H]$^+$.

$^1$H NMR (270 MHz, CDCl$_3$) δ (ppm): 8.00 (d, J=7.3 Hz, 2H, H-20-triazole-<u>phenyl</u>), 7.90 (s, 1H, H-20-<u>triazole</u>-phenyl), 7.46 (t, J=7.6 Hz, 2H, H-20-triazole-<u>phenyl</u>), 7.32 (t, J=6.9 Hz, 1H, H-20-triazole-<u>phenyl</u>), 6.92 (d, J=15.5 Hz, 1H, H-11), 6.14 (d, J=15.2 Hz, 1H, H-10), 4.92 (d, J=9.6 Hz, 1H, H-13), 4.72 (br. dt, J=9.6 Hz, 1H, H-15), 4.60 (m, 2H, H-20), 4.33 (d, J=7.2 Hz, 1H, H-1'), 3.82 (d, J=10.2 Hz, 1H, H-3), 3.50 (m, 1H, H-5), 3.42-3.35 (m, 4H, H-23, H-2', H-5'), 3.22 (m, 1H, H-14), 3.09 (t, J=9.6 Hz, 1H, H-4'), 2.72 (m, 1H, H-19), 2.56 (m, 1H, H-8), 2.49 (s, 6H, 3'-N(C$\underline{H}_3$)$_2$), 2.35 (m, 1H, H-3'), 2.10 (m, 1H, H-6), 1.88 (d, J=6.5 Hz, 1H, H-2), 1.75 (m, 1H, H-16), 1.81-1.57 (m, 4H, H-4, H-7, H-16), 1.49 (s, 3H, H-22), 1.25 (d, J=6.0 Hz, 3H, H-6'), 1.20 (d, J=6.9 Hz, 3H, H-21), 0.04-0.91 (m, 6H, H-17, H-18).

$^{13}$C NMR (67.5 MHz, CDCl$_3$) δ (ppm): 203.7 (C-9), 173.5 (C-1), 148.1 (C-11), 147.6 (C-20-<u>triazole</u>-phenyl), 140.7 (C-13), 136.0 (C-12), 131.0 (C-20-triazole-<u>phenyl</u>), 129.2 (C-20-triazole-<u>phenyl</u>), 128.9 (C-20-triazole-<u>phenyl</u>), 128.1 (C-20-triazole-<u>phenyl</u>), 126.1 (2C, C-20-triazole-<u>phenyl</u>), 119.5 (C-20-<u>triazole</u>-phenyl), 118.2 (C-10), 103.7 (C-1'), 80.1 (C-5), 75.1 (C-15), 73.4 (C-5'), 71.1 (C-4'), 71.0 (C-2'), 69.9 (C-3'), 66.9 (C-3), 51.9 (C-23), 48.0 (C-20), 47.9 (C-8), 47.0 (C-14), 45.0 (C-19), 41.8 (2C, C-7', 8'), 40.8 (C-4), 39.6 (C-2), 32.3 (C-7), 31.5 (C-6), 25.5 (C-16), 18.0 (C-6'), 17.7 (C-21), 13.1 (C-22), 9.7 (C-17), 9.3 (C-18).

(3) Preparation of 20-(4-phenyl-1H-1,2,3-triazol-1-yl)-20-deoxo-23-triazole-23-deoxy-5-O-mycaminosyltylonolides To a solution of YT114 (0.24 g, 0.30 mmol) in CH$_3$CN or MeOH (3.0 mL) were added CuI (2.9 mg, 0.015 mmol), TBTA (1.6 mg, 3.0 μmol) and a suitable acetylene compound, and then the mixture was stirred at rt until the reaction was completed. After completion, the reaction mixture was diluted with CHCl$_3$, washed with 10% NH$_3$ aq. After removing CuI, the filtrate was washed with brine. The organic layer was dried over Na$_2$SO$_4$ and concentrated. The

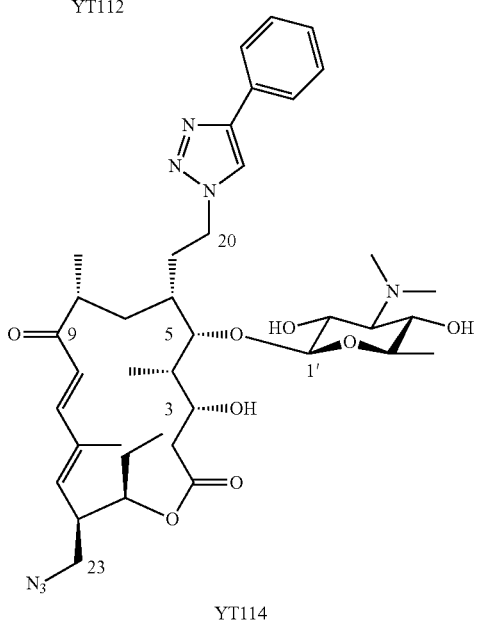

resulting products were purified by flash column chromatography to obtain the following triazole compounds:

20-(4-phenyl-1H-1,2,3-triazol-1-yl)-20-deoxo-23-(4-phenyl-1H-1,2,3-triazol-1-yl)-23-deoxy-5-O-mycaminosyltylonolide (YT115)

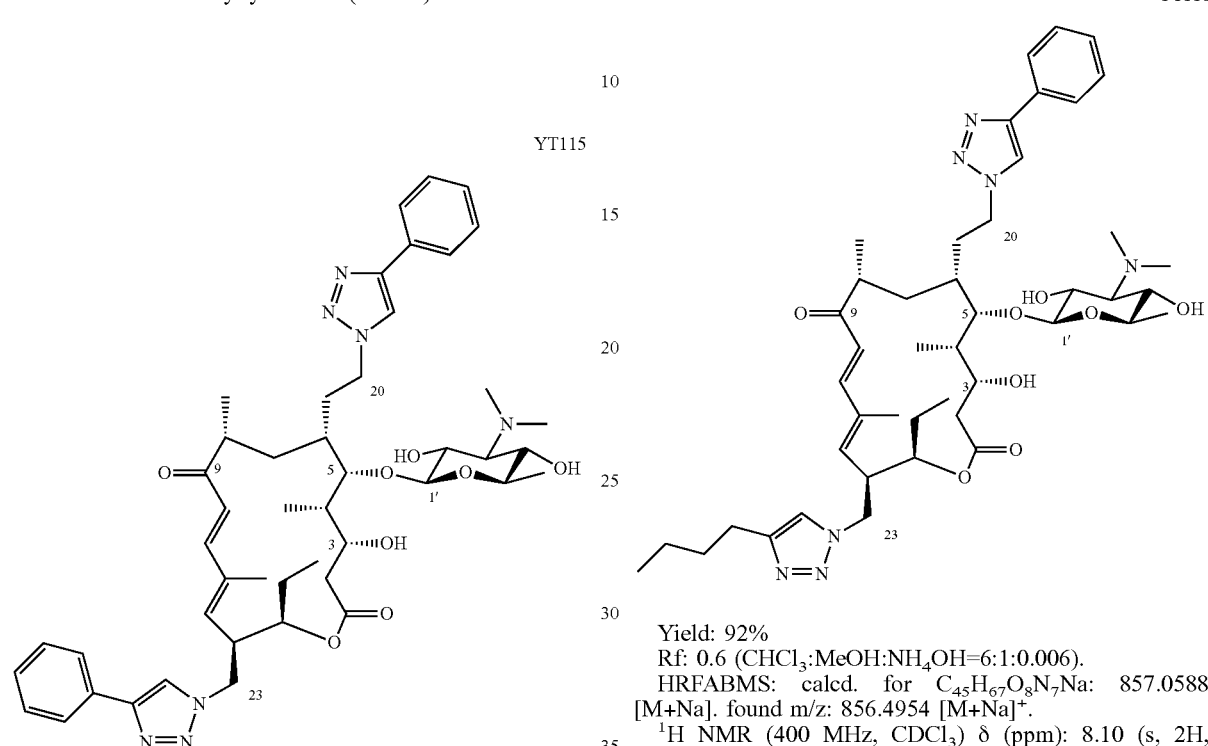

Yield: 85%

Rf: 0.6 (CHCl$_3$:MeOH:NH$_4$OH=6:1:0.006).

HRFABMS: calcd. for C$_{47}$H$_{63}$O$_8$N$_7$Na: 876.4636 [M+Na]. found m/z: 876.4662 [M+Na]$^+$.

$^1$H NMR (400 MHz, CDCl$_3$) δ (ppm): 8.10 (s, 2H, H-20-triazole-phenyl), 7.90 (s, 2H, H-20-triazole-phenyl), 7.72 (d, J=7.6 Hz, 3H, H-20-triazole-phenyl), 7.50 (t, J=7.6 Hz, 4H, H-20-triazole-phenyl), 7.32 (t, J=6.9 Hz, 1H, H-20-triazole-phenyl), 6.65 (d, J=15.5 Hz, 1H, H-11), 6.09 (d, J=15.2 Hz, 1H, H-10), 4.80 (br. d, J=9.6 Hz, 1H, H-13), 4.67 (br. dt, J=9.6 Hz, 1H, H-15), 4.60 (m, 2H, H-23), 4.33 (d, J=7.2 Hz, 1H, H-1'), 4.01 (m, 2H, H-20), 3.84 (d, J=10.2 Hz, 1H, H-3), 3.50 (m, 1H, H-5), 3.45-3.35 (m, 2H, H-2', H-5'), 3.18 (m, 1H, H-14), 3.09 (t, J=9.6 Hz, 1H, H-4'), 2.64 (m, 1H, H-19), 2.63 (m, 1H, H-8), 2.49 (s, 6H, 3'-N(CH$_3$)$_2$), 2.45 (m, 1H, H-3'), 2.15 (m, 1H, H-19), 1.85 (m, 1H, H-6), 1.88 (d, J=6.5 Hz, 1H, H-2), 1.75 (m, 1H, H-16), 1.81-1.57 (m, 4H, H-4, H-7, H-16), 1.49 (s, 3H, H-22), 1.25 (d, J=6.0 Hz, 3H, H-6'), 1.20 (d, J=6.9 Hz, 3H, H-21), 0.04-0.91 (m, 6H, H-17, H-18).

20-(4-phenyl-1H-1,2,3-triazol-1-yl)-20-deoxo-23-(4-butyl-1H-1,2,3-triazol-1-yl)-23-deoxy-5-O-mycaminosyltylonolide (YT116)

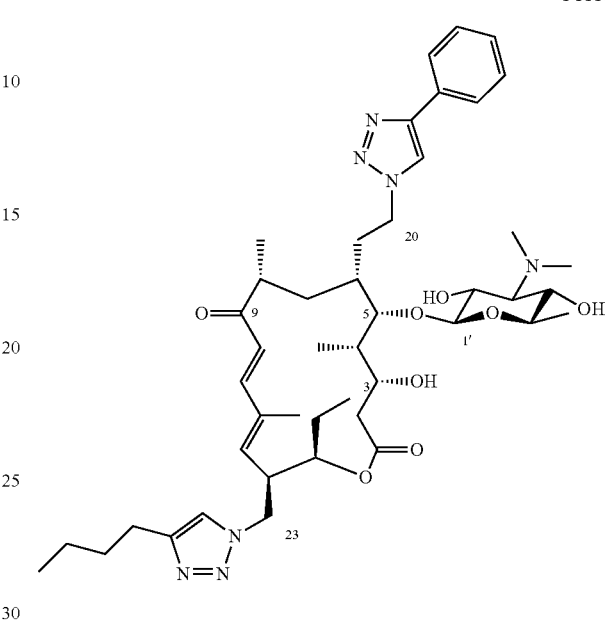

Yield: 92%

Rf: 0.6 (CHCl$_3$:MeOH:NH$_4$OH=6:1:0.006).

HRFABMS: calcd. for C$_{45}$H$_{67}$O$_8$N$_7$Na: 857.0588 [M+Na]. found m/z: 856.4954 [M+Na]$^+$.

$^1$H NMR (400 MHz, CDCl$_3$) δ (ppm): 8.10 (s, 2H, H-20-triazole-phenyl), 7.90 (s, 2H, H-20-triazole-phenyl, H-23-triazole-butyl), 7.72 (d, J=7.6 Hz, 3H, H-20-triazole-phenyl), 7.50 (t, J=7.6 Hz, 4H, H-20-triazole-phenyl), 7.32 (t, J=6.9 Hz, 1H, H-20-triazole-phenyl), 6.62 (d, J=15.5 Hz, 1H, H-11), 6.09 (d, J=15.2 Hz, 1H, H-10), 4.78 (br. d, J=9.6 Hz, 1H, H-13), 4.64 (br. dt, J=9.6 Hz, 1H, H-15), 4.60 (m, 2H, H-23), 4.33 (d, J=7.2 Hz, 1H, H-1'), 3.90 (m, 2H, H-20), 3.84 (d, J=10.2 Hz, 1H, H-3), 3.50 (m, 1H, H-5), 3.45-3.35 (m, 2H, H-2', H-5'), 3.09 (t, J=9.6 Hz, 1H, H-4'), 3.07 (m, 1H, H-14), 2.64 (m, 1H, H-19), 2.63 (m, 1H, H-8), 2.49 (s, 6H, 3'-N(CH$_3$)$_2$), 2.45 (m, 1H, H-3'), 2.15 (m, 1H, H-19), 1.85 (m, 1H, H-6), 1.65 (m, 1H, H-2), 1.86-1.39 (m, 8H, H-4, H-7, H-16, H-22), 1.36-1.10 (m, 12H, H-21, H-6', H-triazole-butyl), 1.02-0.97 (m, 6H, H-18, H-triazole-butyl), 0.90 (t, J=7.2 Hz, 3H, H-17).

Paper Disc Assays (1) Antibacterial Activities Against *Mannheimia* and *Pasteurella* were Determined by the Following Steps:

1) *M. hemolytica* KB345 (Tilmicosin-sensitivity strain) and *M. hemolytica* KB346 (Tilmicosin-low sensitivity strain) were provided. KB 345 strain stored at −80° C. was seeded to BHIB agar medium (10 mL) by using Microbank beads (Pro-Lab) and platinum nail. After statically incubating the KB 345 strain for 24 hours at 37° C., it was seeded to maintaining slant BHIB agar medium (7 mL) by using platinum loop, further statically incubated for 24 hours at 37° C. to obtain slant. One platinum loop of KB 345 strain stored at the slant was inoculated into a large test tube charged with BHIB liquid medium (10 mL) and then incubated for 24 hours at 37° C. with shaking.

2) A paper disc (ADVANTEC, Φ:6 mm) was impregnated with a solution of test compound and dried under reduced pressure.

3) To a melted BHIB agar medium was inoculated 1% of the broth obtained from step 1) above to prepare a test plate. After the medium set, the paper disc prepared in step 2) above was put on the plate and it was incubated at 37° C.

4) After one day, the inhibition zone diameter and clarity (A to E) were determined.

For KB346 strain, the same procedures were repeated.

The results of the assays are shown in Tables below:

TABLE 2

| | | \multicolumn{5}{c|}{Mannhemia hemolytica KB345:} |
| --- | --- | --- | --- | --- | --- | --- |
| | | \multicolumn{5}{c|}{Inhibition zone (mm) and clarity (A to E)} |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| Tylosin | — | 11.0 A | 10.5 B | — | — | — |
| Tilmicosin | —CH$_2$—N(3,5-dimethylpiperidinyl) | NT | NT | 16.0 A | 13.5 A | 10.7 A |
| Tulathromycin | — | NT | NT | 18.0 A | 16.0 A | 12.5 A |
| YT6 | —CHO | NT | 10.5 A | — | — | — |
| YT7 | —CH$_2$OH | — | — | — | — | — |
| YT8 | —CH$_2$Cl | 20.0 A | 18.0 A | 12.5 A | — | — |
| YT11 | —CH$_2$N$_3$ | 18.0 A | 16.0 A | 13.0 A | 10.0 A | — |
| YT12 | —CH$_2$-(1,2,3-triazol-1-yl)-4-(2-pyridyl) | 22.0 A | 19.0 A | 17.0 A | 13.0 A | 9.0 A |
| YT13 | —CH$_2$-(1,2,3-triazol-1-yl)-4-phenyl | 21.0 A | 18.0 A | 16.0 A | 15.0 A | 11.0 A |
| YT14 | —CH$_2$-(1,2,3-triazol-1-yl)-4-(2-thienyl) | 22.0 A | 19.5 A | 16.5 A | 14.0 A | 11.0 A |
| YT16 | —CH$_2$-(1,2,3-triazol-1-yl)-4-(3-pyridyl) | 19.0 A | 16.5 A | 14.5 A | 11.5 A | — |

TABLE 2-continued
Mannhemia hemolytica KB345:
| Sample | 20-position substituent | Inhibition zone (mm) and clarity (A to E) | | | | |
|---|---|---|---|---|---|---|
| | | 100 mg/ 6 mm disk | 30 mg/ 6 mm disk | 10 mg/ 6 mm disk | 3 mg/ 6 mm disk | 1 mg/ 6 mm disk |
| YT17 | 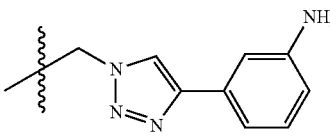 | 19.5 A | 18.0 A | 14.0 A | 12.0 A | — |
| YT18 | 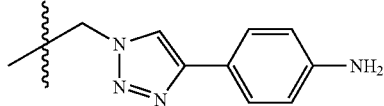 [SMILES: *Cn1cc(-c2ccc(N)cc2)nn1] | 19.5 A | 17.0 A | 14.5 A | 11.0 A | — |
| YT19 | 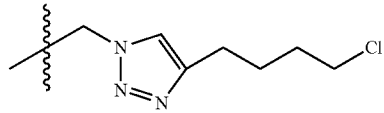 [SMILES: *Cn1cc(CCCCCl)nn1] | 21.0 A | 18.0 A | 16.0 A | 14.0 A | NT |
| YT20 | 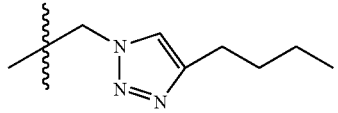 [SMILES: *Cn1cc(CCCC)nn1] | 20.0 A | 17.5 A | 16.0 A | 11.5 A | 9.0 B |
| YT21 | 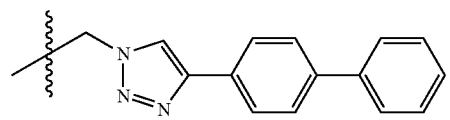 [SMILES: *Cn1cc(-c2ccc(-c3ccccc3)cc2)nn1] | 19.0 A | 18.0 A | 15.5 A | 13.5 A | 11.5 A |
| YT22 | 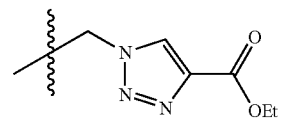 [SMILES: *Cn1cc(C(=O)OCC)nn1] | 21.0 A | 18.0 A | 14.5 A | 11.5 A | 7.5 B |
| YT23 | 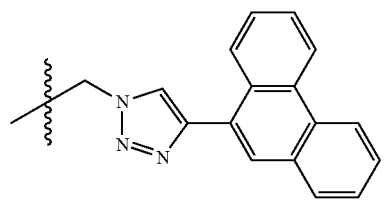 [SMILES: *Cn1cc(-c2cc3ccccc3c3ccccc23)nn1] | 16.5 A | 14.5 A | 13.5 A | 10.0 A | 7.5 B |
| YT24 | 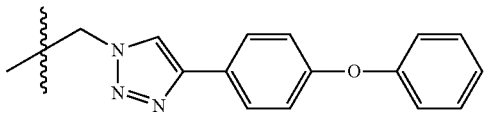 [SMILES: *Cn1cc(-c2ccc(Oc3ccccc3)cc2)nn1] | 18.0 A | 17.0 A | 14.5 A | 12.0 A | 8.5 B |
| YT25 | 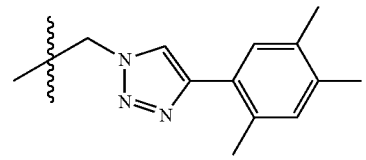 [SMILES: *Cn1cc(-c2cc(C)c(C)cc2C)nn1] | 18.5 A | 17.0 A | 14.0 A | 12.0 A | 8.0 A |
| YT26 | 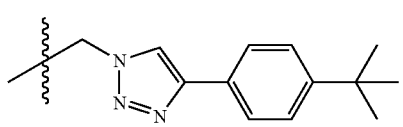 [SMILES: *Cn1cc(-c2ccc(C(C)(C)C)cc2)nn1] | 16.0 A | 14.0 A | 11.5 A | 9.0 A | — |

TABLE 2-continued

Mannhemia hemolytica KB345:

| Sample | 20-position substituent | Inhibition zone (mm) and clarity (A to E) | | | | |
|---|---|---|---|---|---|---|
| | | 100 mg/ 6 mm disk | 30 mg/ 6 mm disk | 10 mg/ 6 mm disk | 3 mg/ 6 mm disk | 1 mg/ 6 mm disk |
| YT27 | triazole-CH2-C6H4-OC5H11 | 16.0 A | 13.0 A | 11.0 A | 9.0 A | — |
| YT28 | triazole-CH2-benzotriazole | 19.0 A | 16.0 A | 13.0 A | 11.0 A | — |
| YT29 | triazole-C6H4-N(CH3)2 | 20.0 A | 17.5 A | 16.0 A | 13.5 A | — |
| YT 30 | triazole-CH2-NH-CH3 | 10.0 A | — | — | — | NT |
| YT32 | triazole-C(CH3)2-OH | 16.0 A | 14.0 A | 9.0 A | — | NT |
| YT33 | triazole-CH2-CH(CH3)2 | 20.0 A | 17.0 A | 16.0 A | 13.0 A | NT |
| YT34 | triazole-(CH2)8- | 15.0 A | 14.0 A | 13.0 A | 11.0 B | NT |
| YT35 | triazole-quinoline | 21.0 A | 19.0 A | 17.0 A | 14.0 A | NT |
| YT36 | triazole-(CH2)4-OH | 9.0 A | — | — | — | NT |
| YT37 | triazole-CH2-OH | 12.5 A | 9.0 A | — | — | NT |

TABLE 3

| | | Mannhemia hemolytica KB346 | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| Tylosin | — | 9.5 B | — | — | — | — |
| Tilmicosin | 3,5-dimethylpiperidinylmethyl | NT | NT | 11.0 A | — | — |
| Tulathromycin | — | NT | NT | 14.0 A | 12.0 A | 9.5 A |
| YT6 | CHO | 21.0 A | 17.5 A | 13.5 A | 8.5 A | — |
| YT7 | CH2OH | — | — | — | — | — |
| YT8 | CH2Cl | 14.5 A | 11.0 A | — | — | — |
| YT11 | CH2N3 | 11.0 A | — | — | — | — |
| YT12 | CH2-triazole-pyridin-2-yl | 16.0 A | 12.0 A | 9.0 B | — | — |
| YT13 | CH2-triazole-phenyl | 15.0 A | 12.0 A | 8.0 B | — | — |
| YT14 | CH2-triazole-thiophen-3-yl | 17.0 A | 12.0 A | 9.0 B | — | — |
| YT16 | CH2-triazole-pyridin-3-yl | 14.0 A | 11.0 A | 7.0 B | — | — |
| YT17 | CH2-triazole-(3-aminophenyl) | 13.0 A | 9.0 A | — | — | — |

TABLE 3-continued

| | Mannhemia hemolytica KB346 | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT18 | [triazole-C6H4-NH2] | 12.5 A | 8.5 A | — | — | — |
| YT19 | [triazole-(CH2)4-Cl] | 16.5 A | 14.0 A | 11.0 A | 7.0 A | — |
| YT20 | [triazole-butyl] | 17.5 A | 14.0 A | 10.5 A | — | — |
| YT21 | [triazole-biphenyl] | 17.0 A | 14.0 A | 12.5 A | 9.0 A | — |
| YT22 | [triazole-C(O)OEt] | 16.0 A | 11.0 A | 9.0 B | — | — |
| YT23 | [triazole-phenanthrenyl] | 11.0 A | 9.0 A | — | — | — |
| YT24 | [triazole-C6H4-O-C6H5] | 9.0 B | — | — | — | — |
| YT25 | [triazole-trimethylphenyl] | 12.5 A | 8.5 A | — | — | — |
| YT26 | [triazole-C6H4-tBu] | — | — | — | — | — |
| YT27 | [triazole-C6H4-OC5H11] | — | — | — | — | — |

TABLE 3-continued

| | | Mannhemia hemolytica KB346 | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT28 | (triazole-CH2-benzotriazole) | 15.0 A | 10.0 A | — | — | — |
| YT29 | (triazole-phenyl-N(CH3)2) | 11.0 A | — | — | — | — |
| YT30 | (triazole-CH2-NHCH3) | 10.0 A | 8.0 B | — | — | — |
| YT32 | (triazole-C(CH3)2-OH) | 13.5 A | 12.0 A | 8.0 B | — | — |
| YT33 | (triazole-isobutyl) | 14.5 A | 14.0 A | — | — | — |
| YT34 | (triazole-(CH2)8) | — | — | — | — | — |
| YT35 | (triazole-quinoline) | 14.5 A | 13.5 A | — | — | — |
| YT36 | (triazole-(CH2)4-OH) | 11.0 A | 8.0 A | — | — | — |
| YT37 | (triazole-CH2OH) | — | — | — | — | — |

TABLE 4

| | | | Mannhemia hemolytica KB345 | | | | |
|---|---|---|---|---|---|---|---|
| | | | Inhibition zone (mm) and clarity (A to E) mg/6 mm disk | | | | |
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| Tilmicosin | — | — | NT | | 18.0 A | 16.0 A | 12.0 A |
| Tylosin | — | — | 11.0 A | 10.5 B | — | — | — |
| YT106 | CHO | CH2OH | 15.0 A | 12.5 A | 8.5 A | — | — |
| YT111 | CHO | CH2I | 25.0 A | 20.0 A | 15.5 A | 11.5 A | NT |
| YT107 | CHO | CH2N3 | 21.5 A | 18.0 A | 16.0 A | 12.0 A | |
| YT101 | CHO | triazole-phenyl | 17.0 A | 14.0 A | 11.0 A | — | — |
| YT102 | CHO | triazole-(CH2)3CH3 | 15.0 A | 11.5 A | 9.0 A | — | — |
| YT103 | CHO | triazole-quinoline | 16.0 A | 14.0 A | 12.0 A | — | — |
| YT104 | CHO | triazole-biphenyl | 12.5 A | 10.0 A | 10.0 A | 9.0 A | — |
| YT109 | CHO | triazole-pyridyl | 12.5 A | 9.5 A | — | — | — |
| YT110 | CHO | triazole-CH2-benzotriazole | 11.5 A | 9.0 A | — | — | — |
| YT112 | triazole-phenyl | CH2OH | 29.0 A | 25.0 A | 20.0 A | 17.0 A | NT |
| YT113 | triazole-phenyl | CH2I | 19.5 A | 18.0 A | 11.0 A | — | NT |

TABLE 4-continued

Mannhemia hemolytica KB345

| | | | Inhibition zone (mm) and clarity (A to E) mg/6 mm disk) | | | | |
|---|---|---|---|---|---|---|---|
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| YT114 | 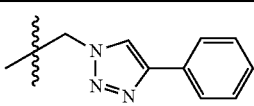 | 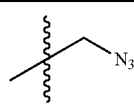 | 21.0 A | 21.0 A | 17.5 A | 11.5 B | NT |
| YT115 | 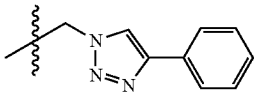 [SMILES: *Cn1cc(-c2ccccc2)nn1] | 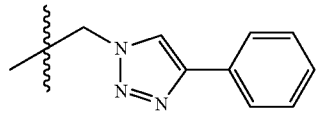 [SMILES: *Cn1cc(-c2ccccc2)nn1] | 16.0 A | 14.0 A | 12.0 A | — | NT |
| YT116 | 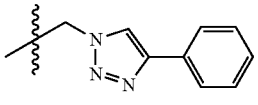 [SMILES: *Cn1cc(-c2ccccc2)nn1] | 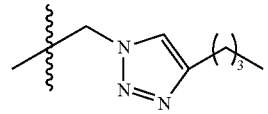 | 17.0 A | 17.0 A | 13.0 A | — | NT |

TABLE 5

Mannhemia hemolytica KB346

| | | | Inhibition zone (mm) and clarity (A to E) | | | | |
|---|---|---|---|---|---|---|---|
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| Tilmicosin | — | — | NT | 11.0 A | — | — | |
| Tylosin | — | — | 11.0 A | 10.5 B | — | — | |
| YT106 | 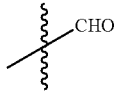 [SMILES: *C=O] | 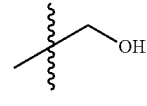 [SMILES: *CO] | 17.0 A | 13.0 A | 9.0 A | — | — |
| YT111 | 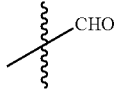 | 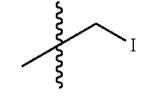 | 13.0 A | 8.5 A | — | — | — |
| YT107 | 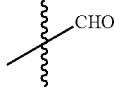 [SMILES: *C=O] | 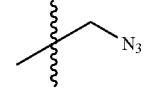 [SMILES: *CN=[N+]=[N-]] | 15.0 A | 10.5 A | — | — | — |
| YT101 | 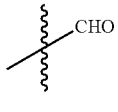 | 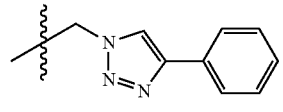 | — | — | — | — | — |
| YT102 | 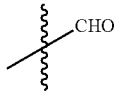 [SMILES: *C=O] | 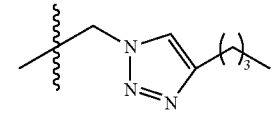 | — | — | — | — | — |
| YT103 | 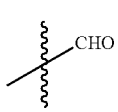 [SMILES: *C=O] | 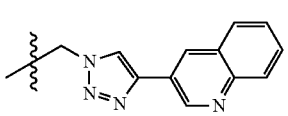 [SMILES: *Cn1cc(-c2cnc3ccccc3c2)nn1] | — | — | — | — | — |

TABLE 5-continued

Mannhemia hemolytica KB346

| | | | Inhibition zone (mm) and clarity (A to E) | | | | |
|---|---|---|---|---|---|---|---|
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| YT104 | CHO | triazole-biphenyl | — | — | — | — | — |
| YT109 | CHO | triazole-pyridyl | 9.0 A | — | — | — | — |
| YT110 | CHO | triazole-CH2-benzotriazole | 8.0 A | — | — | — | — |
| YT112 | triazole-phenyl | OH | 11.5 A | — | — | — | — |
| YT113 | triazole-phenyl | I | — | — | — | — | — |
| YT114 | triazole-phenyl | N3 | — | — | — | — | — |
| YT115 | triazole-phenyl | triazole-phenyl | — | — | — | — | — |
| YT116 | triazole-phenyl | triazole-(CH2)3- | — | — | — | — | — |

(2) Antibacterial activities against other bacteria were determined with *Micrococcus luteus* ATCC9341 (1), *Bacillus subtilis* ATCC663 (s), *Escherichia coli* NIHJ (c), *Xanthomonas campestris* KB88 (X), *Mucor racemosus* IFO 4581 (Mu) and *Candida albicans* ATCC 64548 (Ca).

*Bacillus subtilis* ATCC6633 was incubated in Davis synthetic medium and then the seed broth was combined with the medium in the ratio of 1:99 to obtain a test plate. *Micrococcus luteus* ATCC9341, *Escherichia coli* NIHJ and *Xanthomonas campestris* KB88 were respectively incubated in Nutrient agar medium and inoculated at 0.2%, 0.5% and 1.0%. *Mucor racemosus* IFO 4581 and *Candida albicans* ATCC 64548 were respectively incubated in GY agar medium and then inoculated at 0.3% and 0.2%.

A paper disc (ADVANTEC, Φ:6 mm) was impregnated with a solution of test compound and dried under reduced pressure. The paper disc was put on the test plate and it was incubated for 24 hours at 37° C. After incubation, the inhibition zone diameter and clarity (A to E) were determined.

The results of the assays are shown in Table 6 below:

TABLE 6

Six bacteria

| Sample | 20-position substituent | mg/6 mm disc | Inhibition zone (mm) and clarity | | | | | |
|---|---|---|---|---|---|---|---|---|
| | | | S | l | c | X | Ca | Mu |
| Tilmicosin | 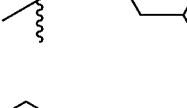 | 10 | 18 A | 27.5 A | 20 C | 30 C | — | — |
| | | 1 | 11 A | 19 A | 13 C | 20 C | — | — |
| | | 0.1 | 14 C | 12 A | — | 12 C | — | — |
| YT12 | 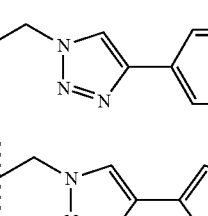 | 10 | 14 A | 25 A | — | 27 B | — | — |
| | | 1 | 12.5 A | 18.5 A | — | 12.5 B | — | — |
| | | 0.1 | 7 A | 12 A | — | 7 B | — | — |
| YT13 | 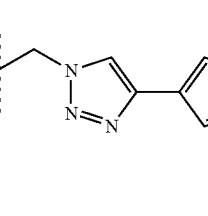 | 10 | 15.5 A | 27.5 A | — | 23.5 B | — | — |
| | | 1 | 12 A | 21.5 A | — | 17 B | — | — |
| | | 0.1 | 9.5 A | 15 A | — | 8 B | — | — |
| YT14 | 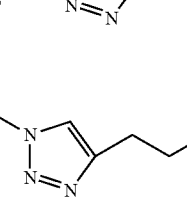 | 10 | 15 A | 26.5 A | 7 B | 22 B | — | — |
| | | 1 | 11 A | 20.5 A | — | 16 B | — | — |
| | | 0.1 | 8 A | 13.5 A | — | 7 B | — | — |
| YT19 | 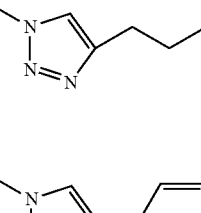 | 10 | 15 A | 26 A | — | 23 B | — | — |
| | | 1 | 10.5 A | 19 A | — | 14.5 B | — | — |
| | | 0.1 | 7 A | 13 A | — | 7 B | — | — |
| YT29 | 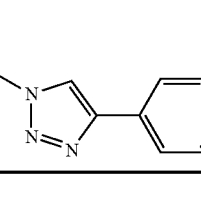 | 10 | 15 A | 25.5 A | — | 24 B | — | — |
| | | 1 | 10 A | 19.5 A | — | 15 B | — | — |
| | | 0.1 | 7 A | 11 A | — | 7 B | — | — |

Minimal inhibitory concentrations (MICs) were determined against the most prevalent pathogens in cattle (*Mannheimia* Haemolytica, 3 isolates) and swine (*A. pleuropneumoniae*, 6 isolates). The results are summarized in Table 7.

TABLE 7

MICs (µg/ml)

| | M. haemolytica isolate | | | pleuropneumoniae isolates | | | | | |
|---|---|---|---|---|---|---|---|---|---|
| Compound | 1 | 2 | 3 | 1 | 2 | 3 | 4 | 5 | 6 |
| YT104 | 8 | 4 | 8 | >16 | >16 | >16 | >16 | >16 | >16 |
| YT112 | 8 | 4 | 8 | 4 | 4 | 4 | 8 | 4 | 8 |

All references, patent applications and publications cited herein are hereby incorporated by reference in its entirety.

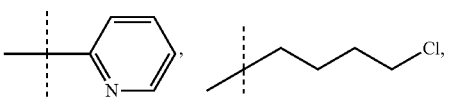

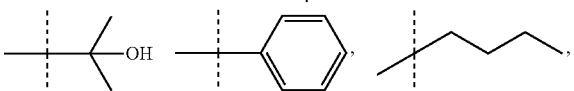

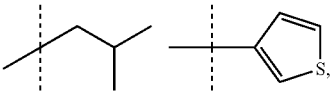

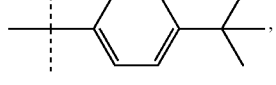

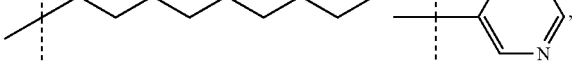

-continued
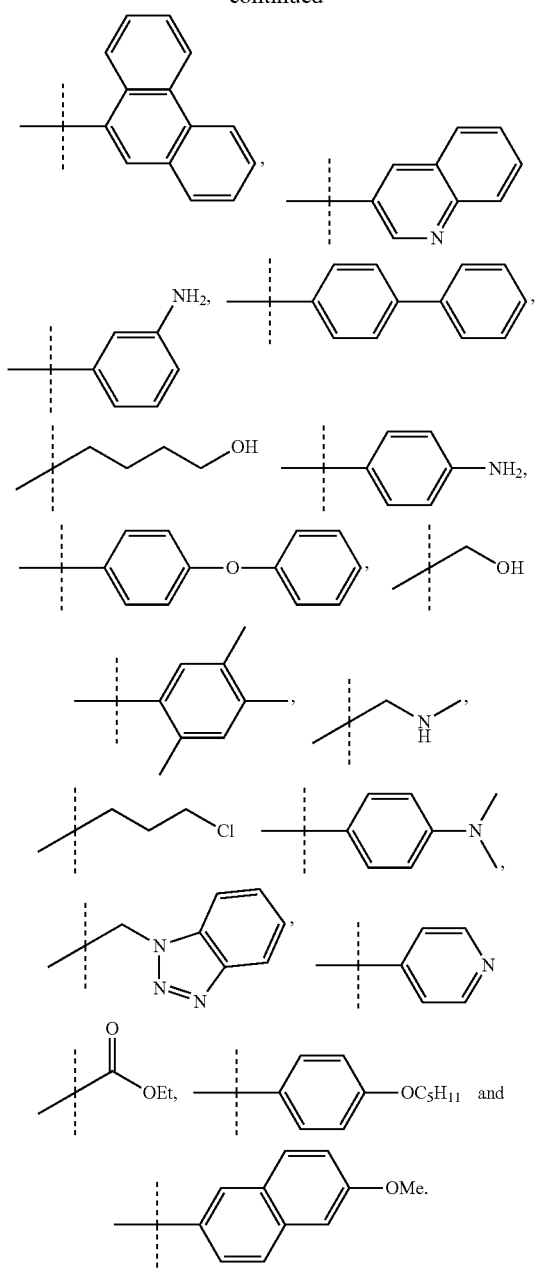
12. The compound of claim 3 wherein;
R is selected from the group consisting of
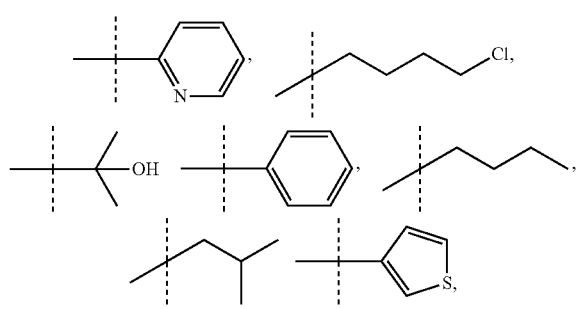
-continued
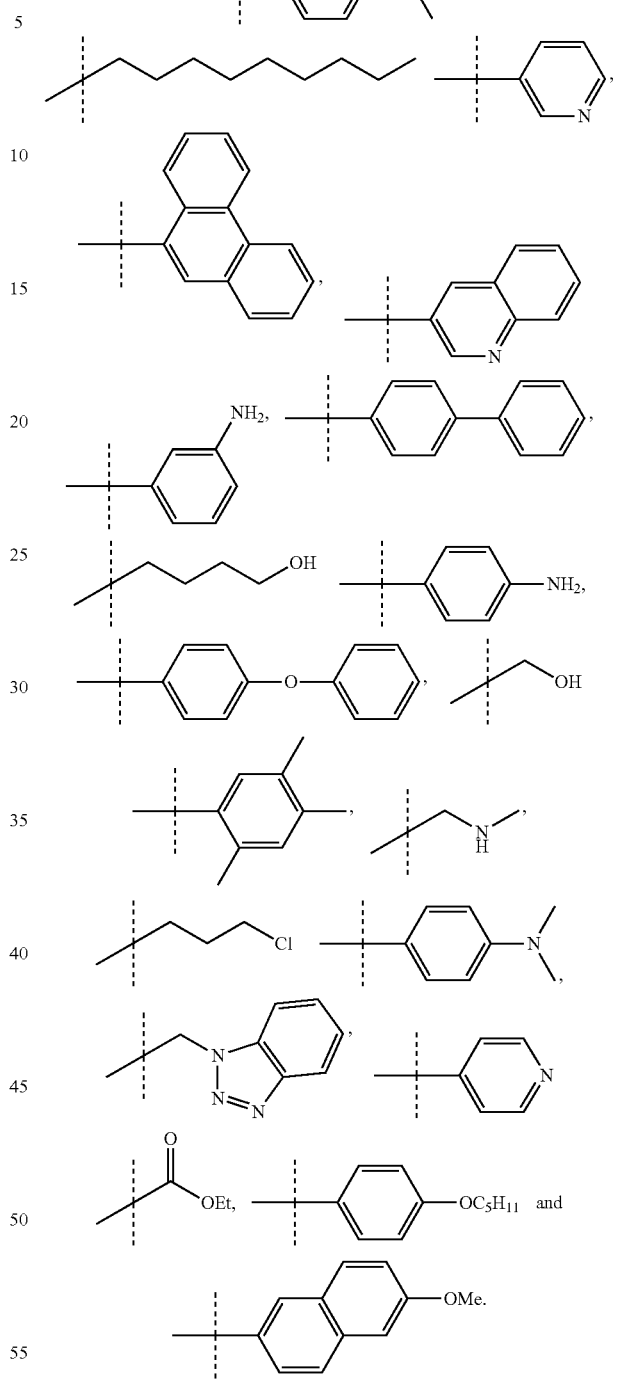
13. The compound of claim 4 wherein;
R is selected from the group consisting of
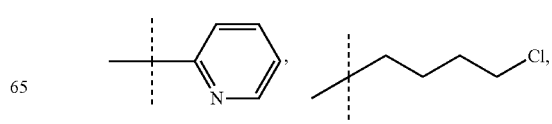

-continued
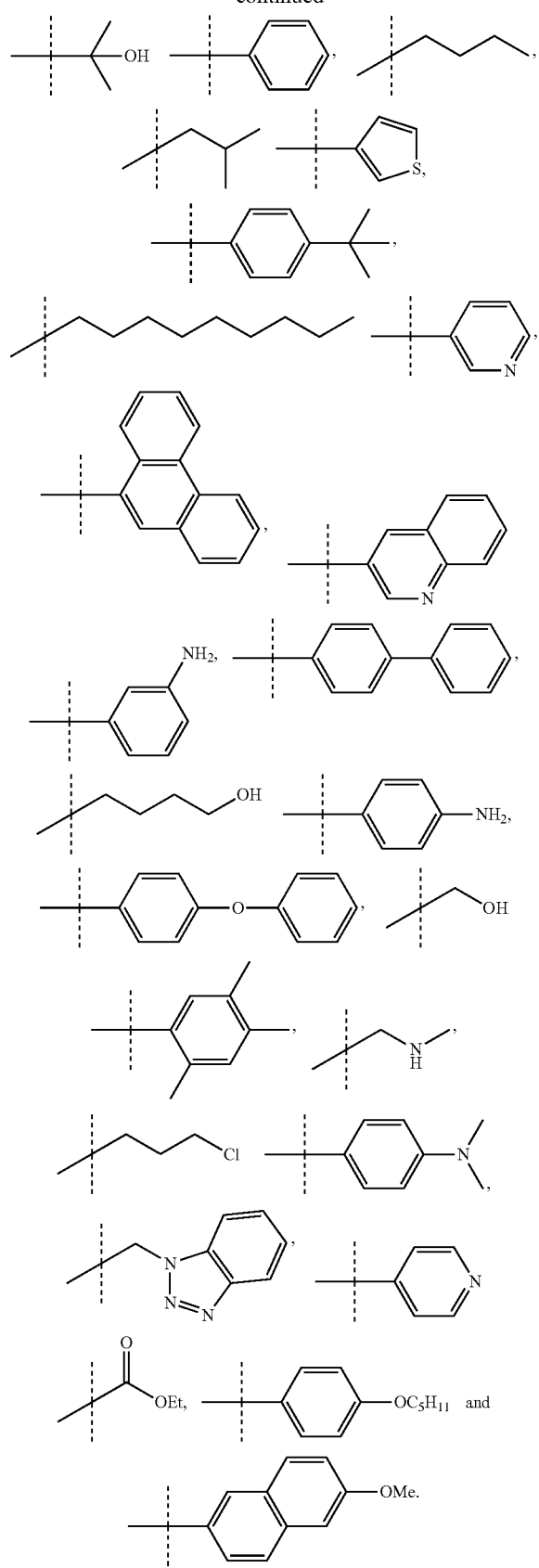
14. The compound of claim 5 wherein;
R is selected from the group consisting of
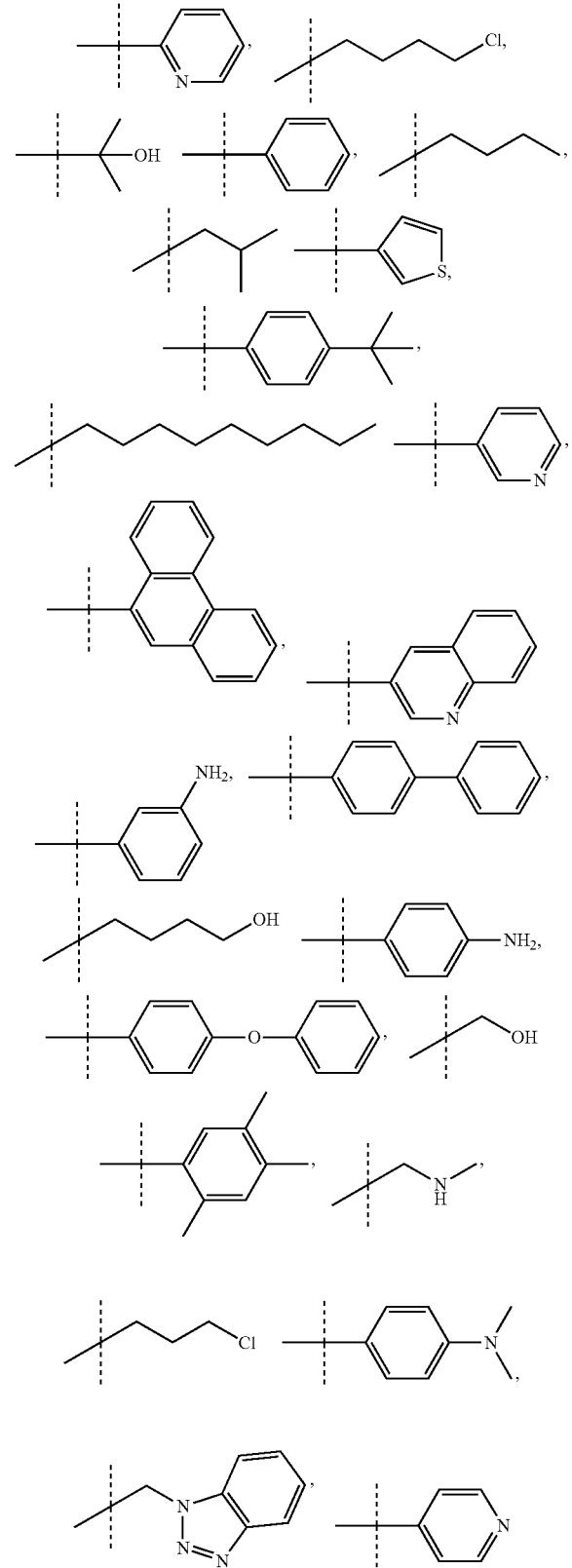

-continued
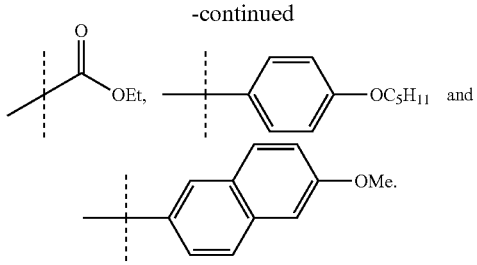

What is claimed is:

1. A compound represented by the formula (I):

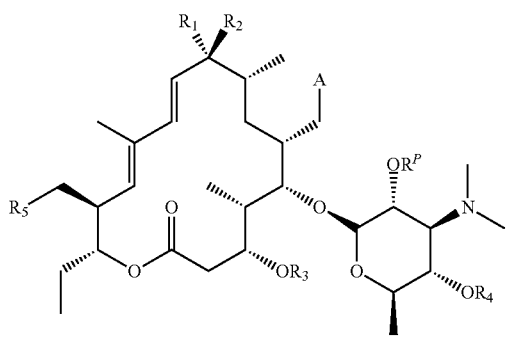

or a pharmaceutically acceptable salt, ester, prodrug or solvate thereof;

wherein, A is selected from the group consisting of:
(1) —CHO or a protected aldehyde;
(2) $CH_2$—X, wherein X is selected from the group consisting of:
a. hydroxy or protected hydroxy;
b. halogen; and
c. —$N_3$
(3) —CN;
(4) —CH=N—NR7R8, wherein R7 and R8 are each independently selected from hydrogen, C1-C6-alkyl, optionally substituted with one or more substituents selected from the group consisting of halogen, aryl, substituted aryl, heterocyclic and substituted heterocyclic, C2-C6-alkenyl, optionally substituted with one or more substituents selected from the group consisting of halogen, aryl, substituted aryl, heterocyclic and substituted heterocyclic, C2-C6-alkynyl, optionally substituted with one or more substituents selected from the group consisting of halogen, aryl, substituted aryl, heterocyclic and substituted heterocyclic or R7 and R8 taken with the nitrogen atom to which they are connected form a 3- to 7-membered ring which may optionally contain a hetero function selected from the group consisting of —O—, —NH—, —N(C1-C6-alkyl)-, —N(aryl)-, —N(heteroaryl)-, —S—, —S(O)— and —S(O)$_2$—;
(5) —CH=N—OR7, wherein R7 is as previously defined;
(6) C3-C14-cycloalkyl;
(7) substituted C3-C14-cycloalkyl;
(8) aryl;
(9) substituted aryl;
(10) heterocyclic;
(11) substituted heterocyclic; and
(12) $CH_2$—R';
R1 and R2
R3 is selected from the group consisting of:
(1) hydrogen;
(2) a hydroxy protecting group;
(3) —C(O)—C1-C12-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(4) C1-C6-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(5) C2-C6-alkenyl, optionally substituted with one or more substituents selected from the group consisting of halogen, aryl, substituted aryl, heterocyclic, substituted heterocyclic, —O—R7 and —NR7R8 where R7 and R8 are as previously defined; and
(6) C2-C6-alkynyl, optionally substituted with one or more substitutents selected from the group consisting of halogen, aryl, substituted aryl, heterocyclic, substituted heterocyclic, —O—R7 and —NR7R8 where R7 and R8 are as previously defined;
R4 is -M-Y, where M is:
(1) absent,
(2) —C(O)—,
(3) —C(O)N(R7)-, where R7 is as previously defined,
(4) —C1-C6-alkyl-N(R7)-, where R7 is as previously defined,
(5) —C2-C6-allcenyl-N(R7)-, where R7 is as previously defined, or
(6) —C2-C6-alkynyl-N(R7)-, where R7 is as previously defined;
and where Y is:
(1) hydrogen,
(2) hydroxy protecting group,
(3) C1-C6-alkyl, optionally substituted with one or more substituents selected from the group consisting of halogen, aryl, substituted aryl, heterocyclic and substituted heterocyclic, —OR7 where R7 is as previously defined,
(4) C2-C6-alkenyl, optionally substituted with one or more substituents selected from the group consisting of halogen, aryl, substituted aryl, heterocyclic and substituted hetreocyclic, —OR7 where R7 is as previously defined,
(5) C2-C6-alkynyl, optionally substituted with one or more substituents selected from the group consisting of halogen, aryl, substituted aryl, heterocyclic and substituted heterocyclic, —OR7 where R7 is as previously defined,
(6) aryl,
(7) substituted aryl,
(8) heterocyclic, or
(9) substituted heterocyclic;
R5 is selected from the group consisting of:
(1) hydrogen;
(2) hydroxy;
(3) protected hydroxy;
(4) halogen;
(5) —O—R7, where R7 is as previously defined;
(6) —$N_3$ or R';
$R^P$ is hydrogen or a hydroxy protecting group;
and each R' is independently [1,4]-epi-[1,2,3]-triazolo R; and where each R is independently selected from the group consisting of:
(1) C1-C9-alkyl, optionally substituted with one or more substituents selected from the group consisting of halogen, aryl, substituted aryl, heterocyclic and substituted heterocyclic, —OR7 where R7 is as previously defined;
(2) C2-C9-alkenyl, optionally substituted with one or more substituents selected from the group consisting of halogen, aryl, substituted aryl, heterocyclic and substituted heterocyclic, —OR7 where R7 is as previously defined;
(3) C2-C9-alkynyl, optionally substituted with one or more substituents selected from the group consisting of halogen, aryl, substituted aryl, heterocyclic and substituted heterocyclic, —OR7 where R7 is as previously defined;
(4) C3-C14-cycloalkyl;
(5) substituted C3-C14-cycloalkyl;
(6) aryl;
(7) substituted aryl;
(8) heterocyclic;
(9) substituted heterocyclic; and
(10) —COOR7, where R7 is as previously defined;
provided that at least one of A and R5 is a group containing R'.
2. The compound of claim 1 wherein;
A is selected from halogen, $CH_2$-$N_3$, hydroxy, CHO, hydroxyC$_1$-6alkyl, haloC$_1$-6alkyl, methyl(3,5-di(C1-C3-alkyl)-piperidino) and $CH_2$—R';
R1 and R2 taken together are oxo
R3 is H;
R4 is H;
R5 is selected from hydroxy, $N_3$, halogen, 6-deoxy-2,3-di-O-methyl-b-d-allo-hexapyranosyloxy and R'; and
each R' is independently [1,4]-epi-[1,2,3]-triazolo-R, where each R is independently selected from the group consisting of:
(1) C1-C9-alkyl, optionally substituted with one or more substituents selected from the group consisting of halogen, aryl, substituted aryl, heterocyclic and substituted heterocyclic, —OR7 where R7 is as previously defined;
(2) C2-C9-alkenyl, optionally substituted with one or more substituents selected from the group consisting of halogen, aryl, substituted aryl, heterocyclic and substituted heterocyclic, —OR7 where R7 is as previously defined;
(3) C2-C9-alkynyl, optionally substituted with one or more substituents selected from the group consisting of halogen, aryl, substituted aryl, heterocyclic and substituted heterocyclic, —OR7 where R7 is as previously defined;
(4) C3-C14-cycloalkyl;
(5) substituted C3-C14-cycloalkyl;
(6) aryl;
(7) substituted aryl;
(8) heterocyclic;
(9) substituted heterocyclic; and
(10) —COOR7, where R7 is as previously defined;
provided that at least one of A and R5 is a group containing R';
or a pharmaceutically acceptable salt, ester, prodrug or solvate thereof.
3. The compound of claim 1 wherein;
A is CH$_2$—R';
R1 and R2 taken together are oxo;
R3 is H;
R4 is H; and
R5 is 6-deoxy-2,3-di-O-methyl-b-d-allo-hexapyranosyloxy.
4. The compound of claim 1 wherein;
A is CHO or methyl(3,5-dimethylpiperidino);
R1 and R2 taken together are oxo;
R3 is H;
R4 is H; and
R5 is R'.
5. The compound of claim 1 wherein;
A is CHO or methyl(3,5-dimethylpiperidino);
R1 and R2 taken together are oxo; and
R3 is H;
R4 is H; and
R5 is 6-deoxy-2,3-di-O-methyl-b-d-allo-hexapyranosyloxy.
6. The compound of claim 1 wherein;
R is selected from the group consisting of

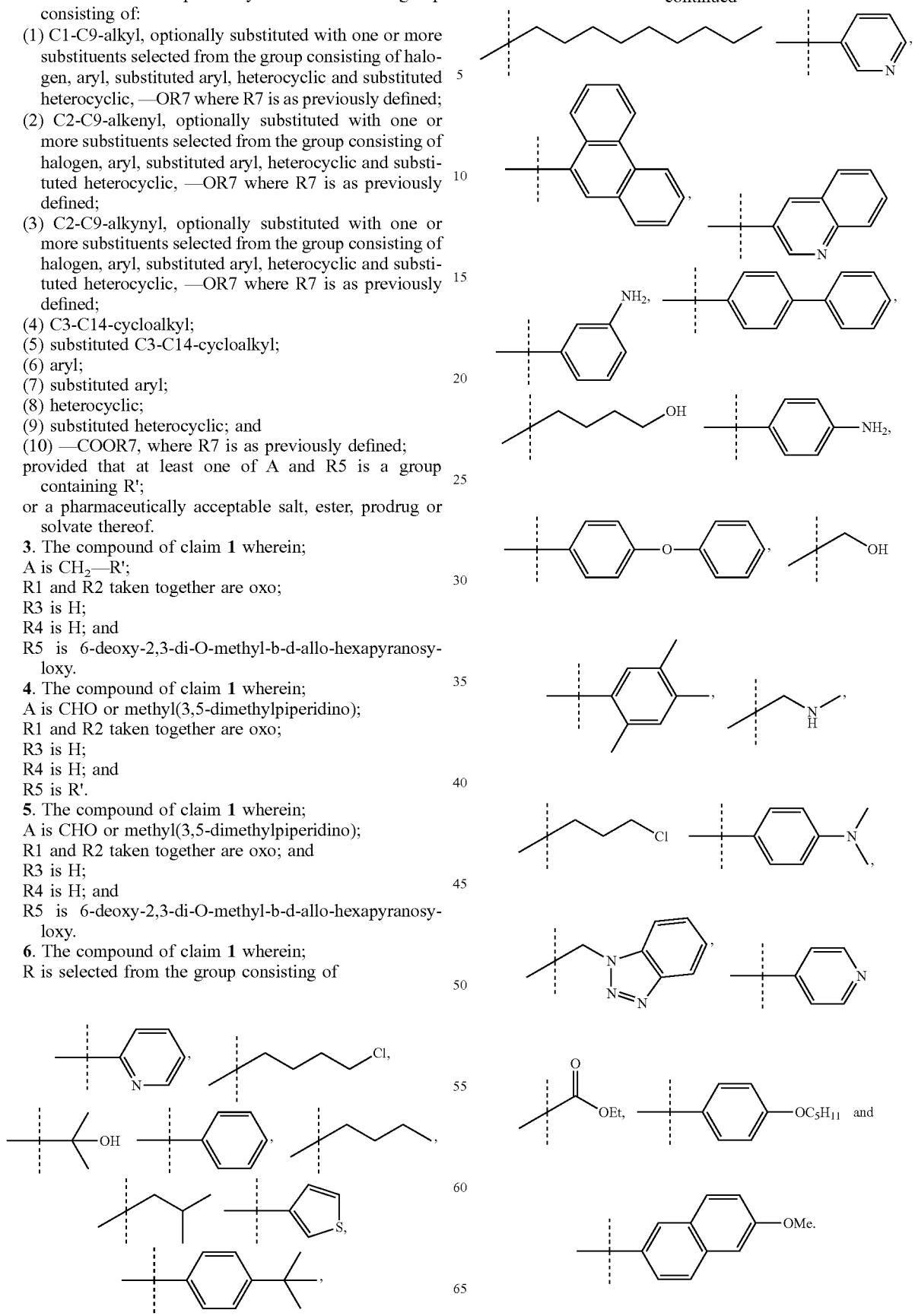

7. A method for preparing a compound of the formula (I):

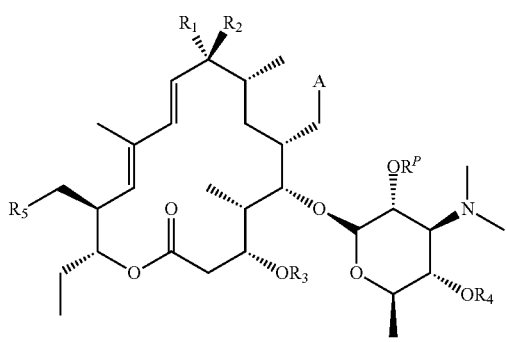
(I)

wherein A is CH$_2$—R' and R1, R2, R3, R4, R5, R' and R$^P$ are as defined in claim 1;
which method comprises following steps:
(i) reacting a compound of the formula (II):

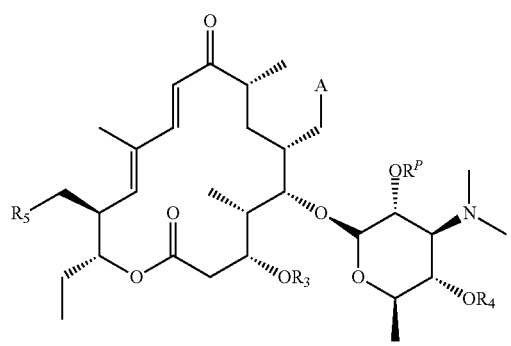
(II)

wherein,
A is CH$_2$-hydroxy; and
the other variable groups are as defined in claim 1, with an azide selected from diphenylphosphoryl azide (DPPA) or sodium azide (NaN$_3$) to form a compound of said formula (II) wherein A is CH$_2$—N$_3$ and the other variable groups are as defined in claim 1; and
(ii) reacting the resulting compound of the formula (II) wherein A is CH$_2$—N$_3$ and the other variable groups are as defined in claim 1 with an R—C≡CH, wherein R is as defined in claim 1 above, in the presence of a copper catalyst to form a compound of the formula (II), wherein A is CH$_2$—R' and R3, R4, R5, R' and R$^P$ are as defined in claim 1.

8. A method for preparing a compound of the formula (I):

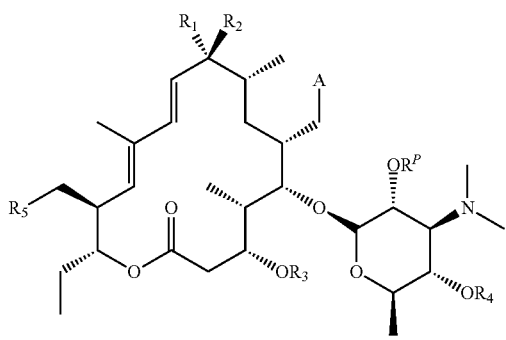
(I)

wherein R5 is R' and A, R1, R2, R3, R4, R' and R$^P$ are as defined in claim 1;
which method comprises following steps:
(i) reacting a compound of the formula (II):

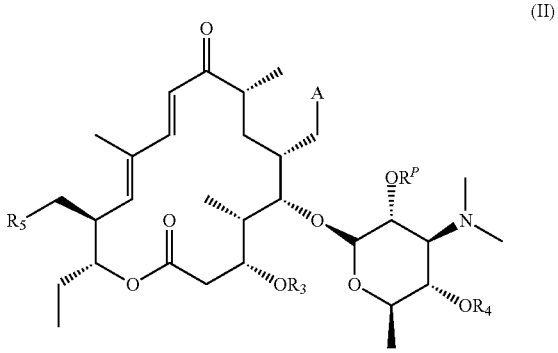
(II)

wherein,
R5 is hydroxy; and
the other variable groups are as defined in claim 1, with an azide selected from diphenylphosphoryl azide (DPPA) or sodium azide (NaN$_3$) to form a compound of said formula (II) wherein R5 is —N$_3$ and the other variable groups are as defined in claim 1; and
(ii) reacting the resulting compound of the formula (II) wherein R5 is —N$_3$ and the other variable groups are as defined in claim 1 with an R—C≡CH, wherein R is as defined in claim 1, in the presence of a copper catalyst to form a compound of the formula (II),
wherein R5 is R' and A, R3, R4, R' and R$^P$ are as defined in claim 1.

9. A pharmaceutical or veterinary composition comprising a compound according to claim 1 and at least one of pharmaceutically acceptable carriers.

10. A method for treating or preventing bacterial infections or disorders associated with bacterial infections in an animal, wherein the method comprises administering to the animal a therapeutically effective amount of the compound according to claim 1.

11. The compound of claim 2 wherein;
R is selected from the group consisting of